US008846090B2

(12) United States Patent
Brögmann et al.

(10) Patent No.: US 8,846,090 B2
(45) Date of Patent: *Sep. 30, 2014

(54) MATRIX FOR SUSTAINED, INVARIANT AND INDEPENDENT RELEASE OF ACTIVE COMPOUNDS

(75) Inventors: Bianca Brögmann, Ulm (DE); Silke Muhlau, Biberach (DE); Christof Spitzley, Eibtal (DE)

(73) Assignee: Euro-Celtique S.A., Luxembourg (LU)

( * ) Notice: Subject to any disclaimer, the term of this patent is extended or adjusted under 35 U.S.C. 154(b) by 0 days.

This patent is subject to a terminal disclaimer.

(21) Appl. No.: 13/348,617

(22) Filed: Jan. 11, 2012

(65) Prior Publication Data

US 2012/0183612 A1 Jul. 19, 2012

Related U.S. Application Data

(63) Continuation of application No. 10/510,673, filed as application No. PCT/EP03/03541 on Apr. 4, 2003, now abandoned.

(30) Foreign Application Priority Data

Apr. 5, 2002 (DE) .................................. 102 15 067
Apr. 5, 2002 (DE) .................................. 102 15 131

(51) Int. Cl.
| | | |
|---|---|---|
| *A61K 9/14* | (2006.01) | |
| *A61K 9/20* | (2006.01) | |
| *A61K 9/22* | (2006.01) | |
| *A61K 31/44* | (2006.01) | |
| *A01N 43/42* | (2006.01) | |
| *A61K 9/16* | (2006.01) | |
| *A61K 9/70* | (2006.01) | |
| *A61K 31/485* | (2006.01) | |

(52) U.S. Cl.
CPC ............. *A61K 31/485* (2013.01); *A61K 9/1652* (2013.01); *A61K 9/2054* (2013.01); *A61K 9/70* (2013.01); *A61K 9/1617* (2013.01); *A61K 9/2077* (2013.01); *A61K 9/2013* (2013.01); *A61K 9/2095* (2013.01); *Y10S 514/81* (2013.01); *Y10S 514/812* (2013.01)
USPC ........... 424/484; 424/464; 424/468; 514/282; 514/810; 514/812

(58) Field of Classification Search
None
See application file for complete search history.

(56) References Cited

U.S. PATENT DOCUMENTS

| | | | |
|---|---|---|---|
| 2,770,569 A | 11/1956 | Fromherz et al. | |
| 3,133,132 A | 5/1964 | Loeb et al. | |
| 3,173,876 A | 3/1965 | Zobrist | |
| 3,173,877 A | 3/1965 | Jackson et al. | |
| 3,276,586 A | 10/1966 | Rosaen | |
| 3,332,950 A | 7/1967 | Blumberg et al. | |
| 3,493,657 A | 2/1970 | Lewenstein et al. | |
| 3,541,005 A | 11/1970 | Strathmann et al. | |
| 3,541,006 A | 11/1970 | Bixler et al. | |
| 3,546,876 A | 12/1970 | Fokker et al. | |
| 3,676,557 A | 7/1972 | Lachman et al. | |
| 3,773,955 A | 11/1973 | Patcher et al. | |
| 3,845,770 A | 11/1974 | Theeuwes et al. | |
| 3,879,555 A | 4/1975 | Pachter et al. | |
| 3,916,889 A | 11/1975 | Russell | |
| 3,916,899 A | 11/1975 | Theeuwes et al. | |
| 3,950,508 A | 4/1976 | Mony et al. | |
| 3,965,256 A | 6/1976 | Leslie | |
| 3,966,940 A | 6/1976 | Pachter et al. | |
| 4,063,064 A | 12/1977 | Saunders et al. | |
| 4,088,864 A | 5/1978 | Theeuwes et al. | |
| 4,126,684 A | 11/1978 | Robson et al. | |
| 4,160,020 A | 7/1979 | Ayer et al. | |
| 4,176,186 A | 11/1979 | Goldberg et al. | |
| 4,200,098 A | 4/1980 | Ayer et al. | |
| 4,237,140 A | 12/1980 | Dudzinski | |
| 4,285,987 A | 8/1981 | Ayer et al. | |
| 4,293,539 A | 10/1981 | Ludwig et al. | |
| 4,366,310 A | 12/1982 | Leslie | |
| 4,401,672 A | 8/1983 | Portoghese et al. | |
| 4,443,428 A | 4/1984 | Oshlack et al. | |
| 4,451,470 A | 5/1984 | Ganti | |
| 4,457,933 A | 7/1984 | Gordon et al. | |
| 4,464,378 A | 8/1984 | Hussain et al. | |
| 4,573,995 A | 3/1986 | Chen et al. | |

(Continued)

FOREIGN PATENT DOCUMENTS

| | | |
|---|---|---|
| AU | 200205559 | 11/2002 |
| CA | 2382648 | 3/2001 |

(Continued)

OTHER PUBLICATIONS

Abernethy et al., Randomised, double blind, placebo controlled crossover trial of sustained release morphine for the management of refractory dyspnoea, BMJ, vol. 327, 6 pages (2003).

(Continued)

*Primary Examiner* — Robert A Wax
*Assistant Examiner* — Caralynne Helm
(74) *Attorney, Agent, or Firm* — Dechert LLP

(57) ABSTRACT

The invention concerns a storage stable pharmaceutical formulation comprising preferably two active compounds in a non-swellable diffusion matrix, whereby the compounds are released from the matrix in a sustained, invariant and, if several compounds are present, independent manner and the matrix is determined with respect to its substantial release characteristics by ethylcellulose and at least one fatty alcohol. The invention also concerns methods for producing such pharmaceutical formulations.

50 Claims, 19 Drawing Sheets

(56) References Cited

U.S. PATENT DOCUMENTS

Figure 1A:
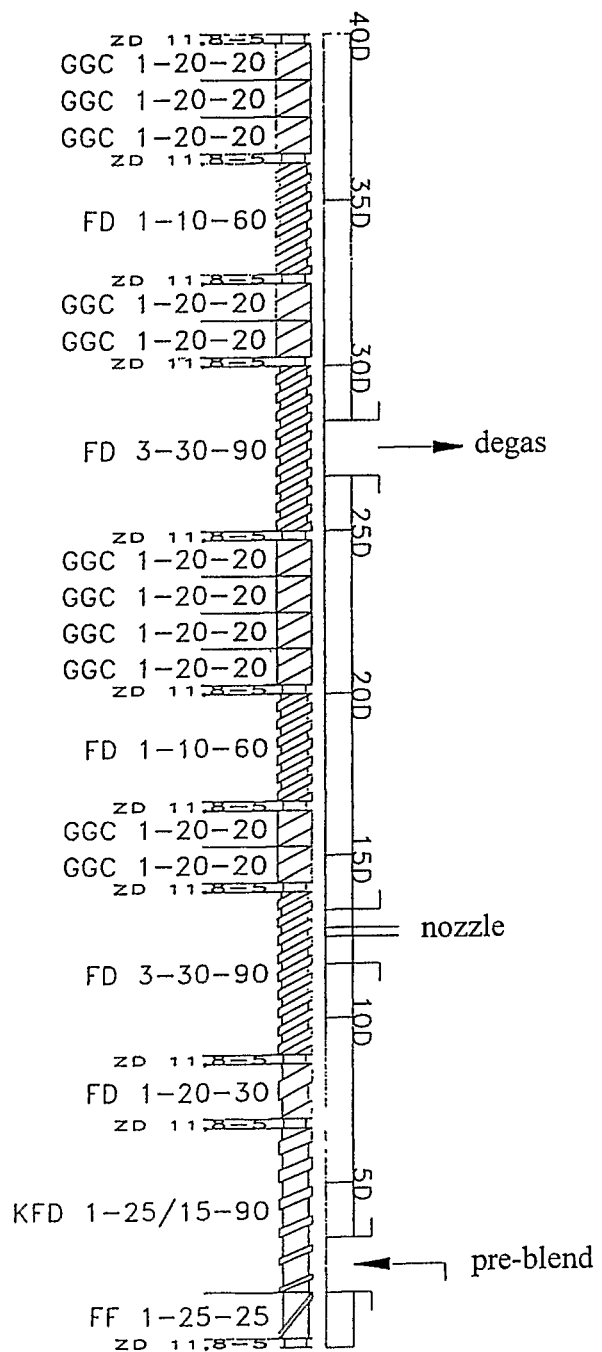

| | | | |
|---|---|---|---|
| 4,582,835 A | 4/1986 | Lewis et al. | |
| 4,608,376 A | 8/1986 | Pasternak | |
| 4,626,539 A * | 12/1986 | Aungst et al. | 514/282 |
| 4,661,492 A | 4/1987 | Lewis et al. | |
| 4,668,685 A | 5/1987 | Shami | |
| 4,719,215 A | 1/1988 | Goldberg | |
| 4,722,928 A | 2/1988 | Boswell et al. | |
| 4,730,048 A | 3/1988 | Portoghese et al. | |
| 4,760,069 A | 7/1988 | Rzeszotarski et al. | |
| 4,769,372 A * | 9/1988 | Kreek | 514/282 |
| 4,785,000 A | 11/1988 | Kreek et al. | |
| 4,803,208 A | 2/1989 | Pasternak | |
| 4,806,341 A | 2/1989 | Chien et al. | |
| 4,806,543 A | 2/1989 | Choi | |
| 4,806,558 A | 2/1989 | Wuest et al. | |
| 4,828,836 A | 5/1989 | Elger et al. | |
| 4,834,965 A | 5/1989 | Martani et al. | |
| 4,834,984 A | 5/1989 | Goldie et al. | |
| 4,834,985 A | 5/1989 | Elger et al. | |
| 4,844,907 A | 7/1989 | Elger et al. | |
| 4,844,909 A | 7/1989 | Goldie et al. | |
| 4,844,910 A | 7/1989 | Leslie et al. | |
| 4,861,598 A | 8/1989 | Oshlack | |
| 4,861,781 A | 8/1989 | Goldberg | |
| 4,867,985 A | 9/1989 | Heafield et al. | |
| 4,873,076 A | 10/1989 | Fishman et al. | |
| 4,882,335 A | 11/1989 | Sinclair | |
| 4,889,860 A | 12/1989 | Rzeszotarski et al. | |
| 4,935,428 A | 6/1990 | Lewis | |
| 4,940,587 A | 7/1990 | Jenkins et al. | |
| 4,957,681 A | 9/1990 | Klimesch et al. | |
| 4,970,075 A | 11/1990 | Oshlack | |
| 4,987,136 A | 1/1991 | Kreek et al. | |
| 4,990,341 A | 2/1991 | Goldie et al. | |
| 5,071,646 A | 12/1991 | Malkowska et al. | |
| 5,075,341 A | 12/1991 | Mendelson et al. | |
| 5,086,058 A | 2/1992 | Sinclair et al. | |
| 5,091,189 A | 2/1992 | Heafield et al. | |
| 5,096,715 A | 3/1992 | Sinclair | |
| 5,102,887 A | 4/1992 | Goldberg | |
| 5,130,311 A | 7/1992 | Guillaumet et al. | |
| 5,149,538 A | 9/1992 | Granger et al. | |
| 5,215,758 A | 6/1993 | Krishnamurthy | |
| 5,225,440 A | 7/1993 | London et al. | |
| 5,236,714 A | 8/1993 | Lee et al. | |
| 5,256,669 A | 10/1993 | Askanazi et al. | |
| 5,266,331 A | 11/1993 | Oshlack et al. | |
| 5,273,760 A | 12/1993 | Oshlack et al. | |
| 5,286,493 A | 2/1994 | Oshlack et al. | |
| 5,316,759 A | 5/1994 | Rose et al. | |
| 5,317,022 A | 5/1994 | Borsodi et al. | |
| 5,321,012 A | 6/1994 | Mayer et al. | |
| 5,324,351 A | 6/1994 | Oshlack et al. | |
| 5,336,691 A | 8/1994 | Raffa et al. | |
| 5,352,680 A | 10/1994 | Portoghese et al. | |
| 5,352,683 A | 10/1994 | Mayer et al. | |
| 5,356,467 A | 10/1994 | Oshlack et al. | |
| 5,356,900 A | 10/1994 | Bihari et al. | |
| 5,376,662 A | 12/1994 | Ockert | |
| 5,409,944 A | 4/1995 | Black et al. | |
| 5,411,745 A | 5/1995 | Oshlack et al. | |
| 5,426,112 A | 6/1995 | Zagon et al. | |
| 5,436,265 A | 7/1995 | Black et al. | |
| 5,457,208 A | 10/1995 | Portoghese et al. | |
| 5,460,826 A | 10/1995 | Merrill et al. | |
| 5,472,712 A | 12/1995 | Oshlack et al. | |
| 5,472,943 A | 12/1995 | Crain et al. | |
| 5,474,995 A | 12/1995 | Ducharme et al. | |
| 5,478,577 A | 12/1995 | Sackler et al. | |
| 5,486,362 A | 1/1996 | Kitchell et al. | |
| 5,500,227 A | 3/1996 | Oshlack et al. | |
| 5,502,058 A | 3/1996 | Mayer et al. | |
| 5,508,042 A | 4/1996 | Oshlack et al. | |
| 5,508,043 A | 4/1996 | Krishnamurthy | |
| 5,510,368 A | 4/1996 | Lau et al. | |
| 5,512,578 A | 4/1996 | Crain et al. | |
| 5,514,680 A | 5/1996 | Weber et al. | |
| 5,521,213 A | 5/1996 | Prasit et al. | |
| 5,534,492 A | 7/1996 | Aston et al. | |
| 5,536,752 A | 7/1996 | Ducharme et al. | |
| 5,549,912 A | 8/1996 | Oshlack et al. | |
| 5,550,142 A | 8/1996 | Ducharme et al. | |
| 5,552,422 A | 9/1996 | Gauthier et al. | |
| 5,556,838 A | 9/1996 | Mayer et al. | |
| 5,574,052 A | 11/1996 | Rose et al. | |
| 5,578,725 A | 11/1996 | Portoghese et al. | |
| 5,580,578 A | 12/1996 | Oshlack et al. | |
| 5,580,876 A | 12/1996 | Crain et al. | |
| 5,585,348 A | 12/1996 | Crain et al. | |
| 5,591,452 A | 1/1997 | Miller et al. | |
| 5,593,994 A | 1/1997 | Batt et al. | |
| 5,601,845 A | 2/1997 | Buxton et al. | |
| 5,604,253 A | 2/1997 | Lau et al. | |
| 5,604,260 A | 2/1997 | Guay et al. | |
| 5,616,601 A | 4/1997 | Khanna et al. | |
| 5,622,722 A | 4/1997 | Knott et al. | |
| 5,624,932 A | 4/1997 | Qin et al. | |
| 5,633,259 A | 5/1997 | Qin et al. | |
| 5,639,476 A | 6/1997 | Oshlack et al. | |
| 5,639,780 A | 6/1997 | Lau et al. | |
| 5,656,295 A | 8/1997 | Oshlack et al. | |
| 5,670,172 A | 9/1997 | Buxton et al. | |
| 5,672,360 A | 9/1997 | Sackler et al. | |
| 5,681,585 A * | 10/1997 | Oshlack et al. | 424/494 |
| 5,692,500 A | 12/1997 | Gaston-Johansson | |
| 5,763,452 A | 6/1998 | Miller et al. | |
| 5,767,125 A | 6/1998 | Crain et al. | |
| 5,780,479 A | 7/1998 | Kim | |
| 5,811,126 A | 9/1998 | Krishnamurthy | |
| 5,834,477 A | 11/1998 | Mioduszewski | |
| 5,843,480 A | 12/1998 | Miller et al. | |
| 5,849,240 A | 12/1998 | Miller et al. | |
| 5,858,017 A | 1/1999 | Demopulos et al. | |
| 5,860,950 A | 1/1999 | Demopulos et al. | |
| 5,866,154 A | 2/1999 | Bahal et al. | |
| 5,866,164 A | 2/1999 | Kucznski et al. | |
| 5,869,097 A | 2/1999 | Wong et al. | |
| 5,879,705 A | 3/1999 | Heafield et al. | |
| 5,880,132 A | 3/1999 | Hill | |
| 5,891,471 A | 4/1999 | Miller et al. | |
| 5,908,848 A | 6/1999 | Miller et al. | |
| 5,942,241 A | 8/1999 | Chasin et al. | |
| 5,958,452 A * | 9/1999 | Oshlack et al. | 424/457 |
| 5,958,459 A | 9/1999 | Chasin et al. | |
| 5,965,161 A | 10/1999 | Oshlack et al. | |
| 5,965,163 A | 10/1999 | Miller et al. | |
| 5,968,547 A | 10/1999 | Reder et al. | |
| 5,968,551 A | 10/1999 | Oshlack et al. | |
| 5,972,954 A | 10/1999 | Foss | |
| 5,998,434 A | 12/1999 | Mitch et al. | |
| 6,024,982 A | 2/2000 | Oshlack et al. | |
| 6,068,855 A | 5/2000 | Leslie et al. | |
| 6,077,532 A | 6/2000 | Malkowska et al. | |
| 6,077,533 A | 6/2000 | Oshlack et al. | |
| 6,096,756 A | 8/2000 | Crain et al. | |
| 6,103,258 A | 8/2000 | Simon | |
| 6,103,261 A | 8/2000 | Chasin et al. | |
| 6,114,326 A | 9/2000 | Schueler | |
| 6,143,322 A | 11/2000 | Sackler et al. | |
| 6,143,328 A | 11/2000 | Heafield et al. | |
| 6,162,467 A | 12/2000 | Miller et al. | |
| 6,194,382 B1 | 2/2001 | Crain et al. | |
| 6,207,142 B1 | 3/2001 | Odds et al. | |
| 6,210,714 B1 | 4/2001 | Oshlack et al. | |
| 6,228,863 B1 | 5/2001 | Palermo et al. | |
| 6,254,887 B1 | 7/2001 | Miller et al. | |
| 6,258,042 B1 | 7/2001 | Factor et al. | |
| 6,261,599 B1 | 7/2001 | Oshlack et al. | |
| 6,277,384 B1 * | 8/2001 | Kaiko et al. | 424/400 |
| 6,294,195 B1 | 9/2001 | Oshlack et al. | |
| 6,306,438 B1 | 10/2001 | Oshlack et al. | |
| 6,310,072 B1 | 10/2001 | Smith et al. | |
| 6,326,027 B1 | 12/2001 | Miller et al. | |
| 6,335,033 B2 | 1/2002 | Oshlack et al. | |

(56) References Cited

U.S. PATENT DOCUMENTS

| | | |
|---|---|---|
| 6,362,194 B1 | 3/2002 | Crain et al. |
| 6,375,957 B1 | 4/2002 | Kaiko et al. |
| 6,387,404 B2 | 5/2002 | Oshlack et al. |
| 6,395,705 B2 | 5/2002 | Crain et al. |
| 6,399,096 B1 | 6/2002 | Miller et al. |
| 6,419,959 B1 | 7/2002 | Walter et al. |
| 6,475,494 B2 | 11/2002 | Kaiko et al. |
| 6,579,536 B1 | 6/2003 | Hirsch et al. |
| 6,596,900 B2 | 7/2003 | Blakemore et al. |
| 6,602,868 B2 | 8/2003 | McBrinn et al. |
| 6,627,635 B2 | 9/2003 | Palermo et al. |
| 6,696,066 B2 | 2/2004 | Kaiko et al. |
| 6,696,088 B2 | 2/2004 | Oshlack et al. |
| 6,706,281 B2 | 3/2004 | Oshlack et al. |
| 6,716,449 B2 | 4/2004 | Oshlack et al. |
| 6,743,442 B2 | 6/2004 | Oshlack et al. |
| 6,765,010 B2 | 7/2004 | Crain et al. |
| 7,172,767 B2 | 2/2007 | Kaiko et al. |
| 7,332,182 B2 | 2/2008 | Sackler |
| 7,419,686 B2 | 9/2008 | Kaiko et al. |
| 7,749,542 B2 | 7/2010 | Kaiko et al. |
| 8,105,631 B2 | 1/2012 | Kaiko et al. |
| 2001/0006967 A1 | 7/2001 | Crain et al. |
| 2001/0018413 A1 | 8/2001 | Crain et al. |
| 2001/0053777 A1 | 12/2001 | Brecht |
| 2002/0006964 A1 | 1/2002 | Young et al. |
| 2002/0010127 A1 | 1/2002 | Oshlack et al. |
| 2002/0031552 A1 | 3/2002 | McTeigue et al. |
| 2003/0004177 A1 | 1/2003 | Kao et al. |
| 2003/0044458 A1 | 3/2003 | Wright, IV et al. |
| 2003/0065002 A1* | 4/2003 | Caruso et al. .......... 514/282 |
| 2003/0069263 A1 | 4/2003 | Breder et al. |
| 2003/0073714 A1 | 4/2003 | Breder et al. |
| 2003/0092759 A1 | 5/2003 | Abuzzahab, Sr. |
| 2003/0118641 A1 | 6/2003 | Maloney et al. |
| 2003/0178031 A1 | 9/2003 | DuPen et al. |
| 2003/0191147 A1 | 10/2003 | Sherman et al. |
| 2003/0229111 A1 | 12/2003 | Oshlack et al. |
| 2004/0052731 A1 | 3/2004 | Hirsh et al. |
| 2004/0092542 A1 | 5/2004 | Oshlack et al. |
| 2004/0186121 A1 | 9/2004 | Oshlack et al. |
| 2005/0063909 A1 | 3/2005 | Wright et al. |
| 2005/0095291 A1 | 5/2005 | Oshlack et al. |
| 2005/0163856 A1 | 7/2005 | Maloney et al. |
| 2005/0181046 A1 | 8/2005 | Oshlack et al. |
| 2005/0245483 A1 | 11/2005 | Brogmann et al. |
| 2005/0245556 A1 | 11/2005 | Brogmann et al. |
| 2005/0272776 A1 | 12/2005 | Buehler |
| 2006/0039970 A1 | 2/2006 | Oshlack et al. |
| 2006/0182801 A1 | 8/2006 | Breder et al. |
| 2007/0122348 A1 | 5/2007 | Kaiko et al. |
| 2007/0185146 A1 | 8/2007 | Fleischer et al. |
| 2008/0145429 A1 | 6/2008 | Leyendecker et al. |

FOREIGN PATENT DOCUMENTS

| | | |
|---|---|---|
| CA | 2478515 | 10/2003 |
| CA | 2478523 | 10/2003 |
| CA | 2372025 | 9/2007 |
| DE | 2138593 | 3/1972 |
| DE | 2222039 | 11/1972 |
| DE | 4325465 | 2/1995 |
| DE | 29719704 | 1/1998 |
| DE | 19651551 | 6/1998 |
| DE | 19857766 | 12/1999 |
| DE | 19859636 | 6/2000 |
| DE | 19918325 | 10/2000 |
| DE | 19938823 | 2/2001 |
| EP | 0193355 | 9/1986 |
| EP | 0205282 | 12/1986 |
| EP | 0319243 | 6/1989 |
| EP | 0352361 | 1/1990 |
| EP | 0527638 | 2/1993 |
| EP | 0576643 | 6/1993 |
| EP | 624366 | 11/1994 |
| EP | 0631781 | 1/1995 |
| EP | 0647448 | 4/1995 |
| EP | 0699436 | 3/1996 |
| EP | 0880352 | 2/1998 |
| EP | 0913152 | 5/1999 |
| EP | 1201233 | 5/2002 |
| EP | 1348429 | 10/2003 |
| EP | 1364649 | 11/2003 |
| EP | 1604666 | 12/2005 |
| EP | 1041987 B1 | 4/2006 |
| EP | 1695700 | 8/2006 |
| EP | 1813276 | 8/2007 |
| GB | 1353815 | 5/1974 |
| GB | 1390772 | 4/1975 |
| JP | H10-251149 | 9/1998 |
| NZ | 260408 | 5/1996 |
| NZ | 264953 | 11/1996 |
| NZ | 260883 | 6/1997 |
| NZ | 294897 | 10/1998 |
| NZ | 544181 | 12/2008 |
| RU | 98102450 | 7/1996 |
| RU | 2222260 | 1/2004 |
| WO | WO 83/03197 | 9/1983 |
| WO | WO 87/01282 | 3/1987 |
| WO | WO 90/04965 | 5/1990 |
| WO | WO 93/10765 | 6/1993 |
| WO | WO 94/06426 | 3/1994 |
| WO | WO 95/03804 | 2/1995 |
| WO | WO 96/02251 | 2/1996 |
| WO | WO 96/14058 | 5/1996 |
| WO | WO 96/14059 | 5/1996 |
| WO | WO 97/33566 | 9/1997 |
| WO | WO 97/45091 | 12/1997 |
| WO | WO 98/25613 | 6/1998 |
| WO | WO 98/35679 | 8/1998 |
| WO | WO 99/01111 | 1/1999 |
| WO | WO 99/05960 | 2/1999 |
| WO | WO 99/22737 | 5/1999 |
| WO | WO 99/32119 | 7/1999 |
| WO | WO 99/32120 | 7/1999 |
| WO | WO 00/01377 | 1/2000 |
| WO | WO 00/25821 | 5/2000 |
| WO | WO 00/38649 | 7/2000 |
| WO | WO 00/41683 | 7/2000 |
| WO | WO 00/51592 | 9/2000 |
| WO | WO 00/67739 | 11/2000 |
| WO | WO 01/32180 | 5/2001 |
| WO | WO 01/37785 | 5/2001 |
| WO | WO 01/52851 | 7/2001 |
| WO | WO 01/58447 | 8/2001 |
| WO | WO 01/58451 | 8/2001 |
| WO | WO 01/68080 | 9/2001 |
| WO | WO 01/85150 | 11/2001 |
| WO | WO 01/85257 | 11/2001 |
| WO | WO 01/93852 | 12/2001 |
| WO | WO 02/087512 | 11/2002 |
| WO | WO 02/092059 | 11/2002 |
| WO | WO 02/092060 | 11/2002 |
| WO | WO 03/003541 | 1/2003 |
| WO | WO 03/004009 | 1/2003 |
| WO | WO 03/007802 | 1/2003 |
| WO | WO 03/013476 | 2/2003 |
| WO | WO 03/013479 | 2/2003 |
| WO | WO 03/013538 | 2/2003 |
| WO | WO 03/020124 | 3/2003 |
| WO | WO 03/024429 | 3/2003 |
| WO | WO 03/024430 | 3/2003 |
| WO | WO 03/026676 | 4/2003 |
| WO | WO 03/073937 | 9/2003 |
| WO | WO 03/084504 | 10/2003 |
| WO | WO 03/084520 | 10/2003 |
| WO | WO 2004/026262 | 4/2004 |
| WO | WO 2004/064807 | 8/2004 |
| WO | WO 2004/091623 | 10/2004 |
| WO | WO 2005/000310 | 1/2005 |
| WO | WO 2005/025621 | 3/2005 |
| WO | WO 2005/079760 | 9/2005 |
| WO | WO 2005/120506 | 12/2005 |

(56) References Cited

FOREIGN PATENT DOCUMENTS

| WO | WO 2005/120507 | 12/2005 |
|---|---|---|
| WO | WO 2006/024881 | 3/2006 |
| WO | WO 2006/079550 | 8/2006 |
| WO | WO 2006/089970 | 8/2006 |
| WO | WO 2006/089973 | 8/2006 |
| WO | WO 2007/047935 | 4/2007 |
| WO | WO 2007/085637 | 8/2007 |
| WO | WO 2007/088489 | 8/2007 |
| WO | WO 2007/111945 | 10/2007 |
| WO | WO 2007/123865 | 11/2007 |
| WO | WO 2008/025790 | 3/2008 |
| WO | WO 2008/030567 | 3/2008 |
| WO | WO 2009/040394 | 4/2009 |
| WO | WO 2010/003963 | 1/2010 |
| WO | WO 2010/103039 | 9/2010 |
| WO | WO 2012/020097 | 2/2012 |

OTHER PUBLICATIONS

Amati et al., "In vitro effects of naloxone on T-lymphocyte-dependent antibacterial activity in hepatitis C virus (HCV) infected patients and in inflammatory bowel disease (IBD) patient," Immunopharmacology and Immonotoxicology, vol. 23, No. 1 (2001), pp. 1-11 (2001).

Beauford et al., "Effects of Nebulized Morphine Sulfate on the Exercise Tolerance Ventilatory Limited COPD Patient," Chest, vol. 104, No. 1, pp. 175-178 (1993).

Benziger et al., "Differential effects of food on the bioavailability of controlled release oxycodone tablets and it oxycodone solution" J Pharm Sciences, vol. 85, No. 4, pp. 407-410 (1996).

Berkow, R. (ed.) Merck Manual of Medical Information, pp. 528-530 (1997).

Caldwell et al., "Treatment of Osteoarthritis Pain with Controlled Release Oxycodone or Fixed Combination Oxycodone Plus Acetaminophen Added to Nonsteroidal Antiinflammatory Drugs: A Double Blind, Randomized, Multicenter, Placebo Controlled Trial," J Rheumatol. vol. 26, No. 4, pp. 862-869 (1999).

Chen et al., "Oral naloxone reverses opioid-associated constipation," Foreign Medical Sciences: Anesthesiology and Resuscitation, vol. 21, No. 5, p. 319 (2000).

Cherry et al., "Opioids in Pain Therapy," The Frankfurt Consensus, STK—Special Issue 2001 Article 2 (3 pages) (in German, w/ English translation).

Citron et al., "Long-term administration of controlled release oxycodone tablets for the treatment of cancer pain," Cancer Investigation, vol. 16, No. 8, pp. 562-571 (1998).

Clark et al., "Symptom indexes to assess outcomes of treatment for early prostate cancer" Medical Care (2001) 39(10) 1118-1130.

Cohen Statistical Power Analysis for the Behavioral Sciences (2nd ed.) Hillsdale, NJ: Erlbaum (1988).

Crain et al. "Antagonists of excitatory opioid receptor functions enhance morphine's analgesic potency and attenuate opioid tolerance/dependence liability," Pain, vol. 84 pp. 121-131 (2000).

Delbarre et al., Naloxone effects on blood pressure, analgesia and dieresis in spontaneous hypertensive and normotensive rats; Neuroscience Letters, vol. 30; pp. 167-172 (1982).

Deyo et al. "Reproducibility and responsiveness of health status measures. Statistics and strategies for evaluation" Cont. Clin. Trials (1991) 12:142S-158S.

Dictionary of Modern Computer Terms, S.-P.: BHV-Petersburg, p. 215 (2004).

Drossman et al. "Rome II: The Functional Gastrointestinal Disorders," 2nd ed. (2000) McLean, VA: Degon Associates.

Ebell et al., "The management of pain in cancer patients," Supportive Measures in Oncology, Jehn et al., eds., 1994, vol. 3 (in German, w/ English translation).

Eissenberg et al. "Buprenophine's physical dependence potential: Antagonist-precipitated withdrawal in humans," J. Pharmacol. Exp. Therapeut. vol. 276, No. 2, p. 449 (1996).

Mundipharma's Opposition to Endo's Australian Patent Application No. AU2002305559, filed Oct. 1, 2008.

Excerpt from Industrial Pharmacy, "Classification of drug delivery systems," 1996 (English translation).

Forth et al., General and Special Pharmacology and Toxicology, 7th rev. ed., 1996, pp. 207-217 (in German w/English Translation).

Goliber (Benchtop Evaluations of Tampering with Pharmaceutical Dosage Forms, Opioid Abuse Resistance Conference, Oct. 2005—Accessed from http://www.thci.org/opioid/oct05docs/TAB%205.8%20Gober.%20Benchtop%20Evaluations%20of%-20Tampering%20with%20Pharmaceutical%20Disage%20Forms.pdf on Nov. 17, 2010.

Grimm, "Extension of the International Conference on Harmonization Tripartite Guideline for Stability Testing of New Drug Substances and Products to Countries of Climatic Zones III and IV," Drug Development and Industrial Pharmacy, vol. 24, No. 4, pp. 312-324 (1998).

Guyatt et al., "Interpreting treatment effects in randomized trials," Br. Med. Jnl, (1998) 316(7132): 690-693.

Hays et al. "Assessing reliability and validity of measurement in clinical trials" in Staquet et al. (eds.) Quality of Life in Clinical Trials: Methods and Practice (1998) Oxford: Oxford University Press.

Hening et al., "Dyskinesias while awake and periodic movements in sleep in restless legs syndrome: Treatment with opioids," Neurology, vol. 36, pp. 1363-1366 (1986).

Hughes et al., "Buprenorphine for pain relief in a patient with drug abuse," The American Journal of Drug and Alcohol Abuse, vol. 17, No. 4, pp. 451-455 (1991).

Hussain M.A. "Improved buccal delivery of opioid analgesics and antagonists with bitterless prodrugs." Pharm. Res. 1988, 5(9):615-618.

Inoue, "On the Treatment of Restless Legs Syndrome," Progress in RLS Research, vol. 24, No. 3, pp. 892-897 (2004).

Israel Patent Appln. No. 192973: office Action dated Sep. 14, 2010, with report letter dated Oct. 24, 2010 as translation (8 pages).

Kanof et al., "Clinical characteristics of naloxone-precipitated withdrawal in human opioid-dependent subjects," J. Pharmacol. Exp. Therapeut., vol. 260, No. 1, pp. 355-363 (1992).

Kazis et al. "Effects sizes for interpreting changes in health status," Med. Care 27(3 Suppl.):S178-S189 (1989).

Kurz et al., "Opioid-Induced Bowel Dysfunction: Pathophysiology and Potential New Therapies," Drugs, vol. 63, No. 7, pp. 649-671 (2003), abstract.

Leehey et al., Naloxone increases water and electrolyte excretion after water loading in patients with cirrhosis and ascites, J of lab and clin med; vol. 118, No. 5, pp. 484-491 (1991).

Leidy et al., "Recommendations for evaluating the validity of quality of life claims for labeling and promotion," Value in Health 2(2): 113-127 (1999).

Levy M.H., Eur J Pain.vol. 5, Suppl. A, pp. 113-116 (2001), abstract.

Liu et al., "Low dose oral naloxone reverses opioid-induced constipation and analgesia"; Journal of Pain and Symptom Management, vol. 23, No. 1, pp. 48-53 (2002).

Meissner et al., "A randomized controlled trial with prolonged-release oral oxycodone and naloxone to prevent and reverse opioid-induced constipation," Eur. J. Pain, vol. 13, pp. 56-64 (2009).

Meissner et al., "Oral naloxone reverses opioid-associated constipation", Pain, vol. 84, pp. 105-109 (2000).

Mundipharma Clinical Study Results for Controlled Release of Oxycodone/Naloxone Formulations, Phase II Study (undated).

Nadstawek et al., "Patient assessment of a novel therapeutic approach for the treatment of severe, chronic pain," Int. J. Clin. Pract., vol. 62, No. 8, pp. 1159-1167 (2008).

Neuenschwander et al., Palliative Medicine At A Glance, 1999 (whole book).

Norman et al., "Interpretation of changes in health-related quality of life: The remarkable universality of half a standard deviation." Med. Care 41:582-592 (2003).

Nunnally et al. Psychometric Theory (3rd Edition) NY: McGraw-Hill (1994).

Oppermann M., "Neue Arzneimittel zur Behandlung der Opioid-induzierten Obstipation: der Mechanismus-basierte A nsatz von

(56) References Cited

OTHER PUBLICATIONS

Methylnaltrexon, Naloxon and Alvimopan," Fortbildungstelegramm Pharmazie; May 1, 2009; pp. 117-131.
Oxygesic® Product Information, 1997-2001 (in German, w/ English translation).
Paille et al., "An open six-month study of the safety of Transipeg for treating constipation in community medicine," J. Clin. Res., vol. 2, pp. 65-76 (1999).
PCT Application PCT/EP2005/006155: International Search Report dated Aug. 25, 2005 (2 pages).
PCT/EP2009/058630: Notification of Transmittal of the International Search Report and the Written Opinion of the International Searching Authority, or the Declaration (with International Search Report, and Written Opinion) dated Oct. 9, 2009.
Philippe et al., "Mu opioid receptor expression is increased in inflammatory bowel diseases: implications for homeostatic intestinal inflammation". GUT, vol. 55, No. 6, pp. 815-823 (2006).
Poole et al., "The Effect of Sustained-Release Morphine on Breathlessness and Quality of Life in Severe Chronic Obstructive Pulmonary Disease," Am J Respir Crit Care Med, vol. 157, pp. 1877-1880 (1998).
Portenoy et al., "Breakthrough pain: characteristics and impact in patients with cancer pain," PAIN, pp. 129-134 (1999).
Portenoy et al., "Breakthrough pain: definition, prevalence and characteristics," PAIN, vol. 41, pp. 273-281 (1990).
Reents et al., "Naloxone and Naltrexone* Application in COPD," Chest, vol. 93, No. 1, pp. 217-219 (1988).
Revicki et al., "Recommendation on health-related quality of life research to support labeling and promotional claims in the United States" QOL Research 9(8):887-900(2000).
Rosow et al., Reversal of opioid-induced bladder dysfunction by intravenous naloxone and methylnaltrexone, Clin Pharm & Ther. vol. 82, No. 1, pp. 48-53 (2007).
Rote Liste 2004, Jan. 1, 2004; Frankfurt/Main, vol. 2004, pp. 05001-05033.
Sandner F., "Hope for patients with chronic pain: naloxone and oxycodone fixed combination offers analgesia and prevention of constipation also during sleep," J of Pham and Therapy, vol. 16; No. 6; pp. 179-180 (2007).
Schenck et al., "Severe, childhood-onset, idiopathic, life-long insomnia responding selectively to opiate therapy: case report with 19 year follow-up," Sleep Med., vol. 2, No. 6, pp. 531-536 (2001).
Schenck et al., Letter to the Editor, Sleep Med., vol. 4, No. 3, p. 251 (2003).
Smith et al., "Low-dose naltrexone as a treatment for active Crohn's disease," AGA Abstracts, S1397, XP009095749, p. A-218 (2006).
Smith et al., "Low-dose naltrexone therapy improves active Crohn's disease," The American Journal of Gastroenterology, vol. 102, No. 4 pp. 820-828 (2007).
Trzepacz et al., "Response to Opioids in Three Patients with Restless Legs Syndrome," Am. J. Psychiatry, vol. 141, pp. 993-999 (1984).
U.S. Appl. No. 10/510,674: Final Office Action dated Jun. 12, 2009, (15 pages).
U.S. Appl. No. 10/510,674: Final Office Action dated Sep. 15, 2010, (14 pages).
U.S. Appl. No. 10/510,674: Non-Final Office Action dated Jan. 5, 2010, (17 pages).
U.S. Appl. No. 10/510,674: Non-Final Office Action dated Jul. 18, 2008 (11 pages).
U.S. Appl. No. 11/570,197: Final Office Action dated Sep. 21, 2010 (18 pages).
U.S. Appl. No. 11/570,197: Non-Final Office Action dated Jun. 4, 2010, including PTO Form 892 (15 pages).
U.S. Appl. No. 11/570,222: Non-Final Office Action dated Oct. 13, 2010 (10 pages).
U.S. Appl. No. 11/574,778: Non-Final Office Action dated Dec. 9, 2010, including PTO Form 892 (13 pages).
U.S. Appl. No. 11/884,288: Non-Final Office Action dated May 12, 2010, including PTO Form 892 (9 pages).
U.S. Appl. No. 12/162,390: Final Office Action dated Dec. 27, 2010, including PTO Form 892 (13 pages).
Valoron® Product Information, 1997-2001 (in German, w/ English translation).
Vondrackova et al. " Analgesic efficacy and safety of oxycodone in combination with naloxone as prolonged release tablets in patients with moderate to severe chronic pain," Journal of Pain, vol. 9, No. 12 pp. 1144-1154 (2008).
Walters et al., "Successful Treatment of the Idiopathic Restless Legs Syndrome in a Randomized Double-Blind Trial of Oxycodone Versus Placebo," Sleep, vol. 16, No. 4, pp. 327-332 (1993).
Wilkinson "The Dynamics of Drug Absorption, Distribution, and Elimination," Goodman and Gilman's The Pharmacological Basis of Therapeutics, Chapter 1, Pharmacokinetics, copyright page and pp. 3-29 (2001).
Wyrwich et al. "Further evidence supporting an SEM-based criterion for identifying meaningful intra-individual changes in health-related quality of life" J.Clin. Epidemiol. 52:861-873 (1991).
Zech et al., "Validation of World Health Organization Guidelines for Cancer Pain Relief: a 10-year Prospective Study," Pain, Oct. 1995:63(1):65-76.
Zeppetella et al., "Opioids for cancer breakthrough pain: A pilot study reporting patient assessment of time to meaningful pain relief," J of Pain and Symptom Management, vol. 25, No. 5, pp. 563-567 (2008).
Zhou et al. "A clinical analysis of 18 cases of naloxone treating pruritis due to cholestia, hebei," Modern Journal of Integrated Chinese and Western Medicine, vol. 8, No. 1, p. 43 (1999) (English translation).
European Patent No. EP1492506: Opposition dated Sep. 30, 2009 by Hexal AG (English translation).
EP Application No. EP10180364.1: Office Communication and European Search Report, dated Dec. 10, 2010.
EP Application No. EP10180425.0: Office Communication and European Search Report, dated Dec. 10, 2010.
Abdulla et al., "Axotomy reduces the effect of analgesic opioids yet increases the effect of nociceptin on dorsal root ganglion neurons"; J of Neuro Sci (1998) vol. 18, pp. 9685-9694.
Alvarez-Fuentes et al. "Effectiveness of Repeated Administration of a New Oral Naltrexone Controlled-Release System in Morphine Analgesia"; J. Pharm Pharmacol (2001), 53:1201-1205.
Alvarez-Fuentes, et al., "Preclinical Study of an Oral Controlled Release Naltrexone Complex in Mice"; J. Pharm Pharmacol (2000), 52:659-663.
Amass et al., "Efficacy of daily and alternate-day dosing regimens with the combibation buprenorphine-Naloxone tablet"; Drug and Alcohol Dependence (2000) vol. 58, pp. 143-152.
Archer Sydney; "Historical Perspective on the Chemistry and Development of Naltrexone"; Naltrexone Research Monograph28 (1980) p. 3-9.
Barton et al., "Intranasal Administration of Naloxone by Paramedics";Prehospital Emergency Care (2002) vol. 6, No. 1, pp. 54-58.
Bashaw et al., "Relative bioavailability of controlled-release oral morphine sulfate during naltrexone blockade"; Inter J of Clin Pharm and Thea (1995) vol. 33, No. 9, 524-529.
Baum et al., "The Impact of the Addition of Naloxone on the Use and Abuse of Pentazocine"; Public Health Reports (1987) vol. 102, No. 4 p. 426-429.
Benfey "Function of Myocardial—Adrenoceptors" ; Life Sciences (1982) vol. 31, pp. 101-112.
Berkow, R. (ed.) The Merck Manual of Diagnosis and Therapy (1997), extract (English Translation from Russian).
Bigelow et al., "Abuse Liability and Assessment of Buprenorphine-Naloxone Combinations"; Dept of Psychiatry and Behavioral Sciences, The Johns Hopkins University School of Medicine, pp. 145-149, (1987).
Blachly Paul, H., M.D., "Naloxone in Opiate Addiction"; Current Psychiatric Therapies (1976) pp. 209-213.
Bloom et al., "Clinical Studies with Naloxone/Methadone in a Ratio of 1:20"; 5th National Conference on Methadone Treatment (1973) vol. 2, p. 1342-1349.

(56) References Cited

OTHER PUBLICATIONS

Brennscheidt et al., "Pharmacokinetics of Nortilidine and Naloxone after Administration of Tilidine/Naloxone Solution or Tilidine/Naloxone Sustained Release Tablets"; Arzeim-Forsch/Drug Res. (2000) vol. 50, pp. 1015-1022.

Briscoe et al., "Methoclocinnamox: Time Course of Changes in Alfetnanil-Reinforced Rhesus Monkeys"; Psychopharmacology (2000) 148:393-399.

Bromm et al., "A Sensitive Method to Evaluate Effects of Analgesics in Man"; Meth and Find Exptl Clin Pharmacol 5 (8) (1983) p. 545-551 (abstract).

Budd, Keith, "Clinical Use of Opioid Antagonists"; Bailliere's Clinical Anesthesiology (1987) vol. 1, No. 4, pp. 993-1011.

Bullingham et al., "Clinical Pharmacokinetics of Narcotic Agonist-Antagonist Drugs"; Clinical Pharm (1983) 8: 332-343.

Bunzow et al., "Molecular cloning and tissue distribution of a putative member of the rat opioid receptor gene family that is not a mu, delta or kappa opioid receptor type." FEBS Lett. Jun. 27, 1994;347(2-3):284-8.

Calimlim, et al. "Effect of Naloxone on the Analgesic Activity of Methadone in a 1:10 Oral Combination"; Clin Pharmacol and There (1974) vol. 15; No. 6 pp. 556-564.

Cappel et al., "Enhancement of Naloxone Induced Analgesia by Pretreatment with Morphine" Pharma. Bioch. & Behav. (1989), 34:425-427.

Caruso et al., "Methadone and Naloxone in Combination (Naldone®) for the Treatment of Heroin Addicts"; Bristol Laboratories, pp. 1336-1341 (1973).

Chambers Dictionary of Science and Technology, Ed. P.M.B. Walker, Chambers, 1999, p. 803.

Cherny Nathan I., "Opioid Analgesics"; Drugs May 1996:51 (5) pp. 713-737.

Chen et al., "Challenges and New Technologies of Oral Controlled Release," Oral Controlled Release Formulation Design and Drug Delivery: Theory to Practice (2010) pp. 257-277.

Chiang et al., "Kinetics of a Naltrexone Sustained-Release Preparation"; Clin Pharmacy Thera (1984) vol. 36 No. 5, pp. 704-708.

Chiang et al. "Clinical Evaluation of a Naltrexone Sustained-Release Preparation"; Drug and Alcohol Dependence (1985) 16, pp. 1-8.

Chih-Cheng Chien et al., "Sigma Antagonists Potentiate Opioid Analgesia in Rats", Neuroscience Letters 190 (1995), 137-139.

Choi et al., "Opioid Antagonists: A Review of Their Role in Palliative care, Focusing on Use in Opioid-Related Constipation," J. of Pain and Symptom Management, vol. 24(1): 71-90.

Ciccocioppo et al., "Effect of Nociceptin/orphanin FQ on the Rewarding Properties of Morphine"; Eur. J Pharmacol (2000) vol. 404, pp. 153-159.

Clemens et al., "Combined oral prolonged-release oxycodone and naloxone in opioid-induced bowel dysfunction: review of efficacy and safety data in the treatment of patients experiencing chronic pain," Expert Opinion on Pharmacotherapy, 11(2):297-310 (2010).

Comer et al., "Depot Naltrexone: Long-lasting Antagonism of the Effects of Heroin un Humans"; Psychopharmacology (2002) 159, pp. 351-360.

Complaint for Declaratory Judgment filed in the United States District Court for the Western District Court of Virginia on Nov. 17, 2008, Civil Action No. 1:08CV00050.

Crabtree et al., "Review of Naltrexone, a long-acting Opiate Antagonist"; Clinical Pharmacy, vol. 3 (1984) pp. 273-280.

Crain et al., "Acute thermal hyperalgesia elicited by low-dose morphine in normal mice is blocked by ultra-low-dose naltrexone, unmasking potent opioid analgesia"; Brain Research (2001) vol. 888, pp. 75-82.

Crain et al., "Antagonists of Excitatory Opioid Receptor Functions Enhance Morphine's Analgesic Potency and Attenuate Opioid Tolerance/dependence liability"; Dept. Of Neuroscience, Albert Einstein College of Medicine Pain 84 (2000) pp. 121-131.

Crain et al., "Ultra-Low Concentrations of Naloxone Selectively Antagonize Excitory Effects of Morphine on Sensory Neurons, Thereby Increasing Its Antinociceptive Potency and Attenuating Tolerance/Dependence During Chronic Cotreatment," Proc. Natl. Acad. Sci. USA (1995) 92:10540-10544.

Culpepper-Morgan et al., "Treatment of opioid-induced constipation with oral naloxone: A pilot study." Clinical Trials and Therapeutics, (1992) vol. 52(1): 90-95.

Davies, S., "Rising to the pain challenge," Drug News Perspect, 19(10):653-8 (2006).

Di Giannuario et al., "Orphanin FQ reduces morphine-induced dopamine release in the nucleus accumbens: a microdialysis study in rats"; Neurosci. Lett (1999) vol. 272 pp. 183-186.

Fink et al., "Naloxone in Heroin Dependence"; Clin Pharm and Thera. vol. 9, No. 5;pp. 568-577, (1968).

Fishman et al., "Disposition of Naloxone-7,8-3H in Normal & Narcotic Dependent Men"; J. Pharm. And Exper. Thera (1973)vol. 10 No. 2;pp. 575-580.

Foss et al., "Dose related Antagonism of the Emetic Effect of Morphine by Methylnaltrexone in Dogs",J. Clin Pharmacol (1993), 33:747-751.

Foss J.F., et al. Abstract, "Prevention of Apomorphine- or Cisplatin-induced emesis in the dog by combination of Methylnaltrexone and Morphine",Cancer Chemother Pharmacol (1998); 42(4):287-91.

Fraser Albert D., et al., "Clinical Toxicology of Drugs Used in the Treatment of Opiate Dependency"; Clinical Toxicology I (1990) vol. 10, No. 2; pp. 375-386.

Freye et al., 'Effects of Tramadol and Tilidine/Naloxone on Oral-Caecal Transit & Pupillary light Reflex'; Arzneim-Forsch/Drug Res. 50(I)(2000)pp. 24-30.

Fudala et al., "Human Pharmacology and Abuse Potential of Nalmefene"; Clin Pharm and Thera (1991) vol. 49, 3, pp. 300-306.

Fudala et al., "Effects of Buprenorphine and Naloxone in Morphine-Stabilized Opioid Addicts"; Drug and Alcohol Dependence 50 (1998) pp. 1-8.

Gal et al., "Prolonged Blockade of Opioid Effect with Oral Nalmefene"; Clin Pharm and Thera (1986) pp. 537-542.

Gan et al., "Opioid-Sparing Effects of a Low-Dose Infusion of Naloxone in Patient-Administered Morphine Sulfate," Anesthesiology (1997), 87(5):1075-1080.

Gerra et al., "Clonidine and Opiate Receptor Antagonists in the Treatment of Heroin Addiction"; J. Substance Abuse Treatment (1995) vol. 12, 1, pp. 35-41.

Ghodse et al., "Opioid analgesics and Narcotic Antagonists"; Side Effects of Drugs (2000) Annual 23, chpt 8 pp. 96-113.

Glatt William, M.D. FACP, "A New Method for Detoxifying Opioid-Dependent Patients"; J. Substance Abuse Treatment (1999) vol. 17, No. 3,pp. 193-197.

Gold et al. "Rapid Opioid Detoxification During General Anesthesia"; Anesthesiology (1999) vol. 91, No. 6, pp. 1639-1647.

Gonzalez et al., "Naltrexone: A Review of its Pharmacodynamic and Pharmacokinetic Properties and Therapeutic Efficacy in the Management of Opioid Dependence," Drugs (1988), 35:192-213.

Goodman and Gilman's The Pharmacological Basis of Therapeutics (Tenth Edition (2001), McGraw Hill.

Goodridge et al., "Factors associated with opioid dispensation for patients with COPD and lung cancer in the last year of life: A retrospective analysis," Int. J. of COPD, 2010, 5:99-105.

Greenwald et al., "Comparative Clinical Pharmacology of Short-Acting Opioids in Drug Abusers"; J. Pharm and Exper Thera (1996) vol. 277, No. 3, pp. 1228-1236.

Gupta et al., "Morphine Combined with Doxapram or Naloxone"; Anesthesia (1974) vol. 29, pp. 33-39.

Guyatt et al. "Measuring change over time: assessing the usefulness of evaluative instruments" J. Chron Dis. (1987) 40(2):171-178.

Hagen, et al. "Efficacy, Safety, and Steady-State Pharmacokinetics of Once-A-Day Controlled-Release Morphine (MS Contin XL) in Cancer Pain," Journal of Pain and Symptom Management (2005) vol. 29, No. 1, pp. 80-90.

Han et al., "Muccoadhesive buccal disks for novel nalbuphine prodrug controlled delivery; effect of formulation variable on drug release and mucoadhesive performance"; International J. Pharm (1999) vol. 177, pp. 201-209.

Handal et al., "Naloxone"; Annals of Emergency Medicine (1983) vol. 12:7, pp. 438-445.

(56) References Cited

OTHER PUBLICATIONS

Hanson Analgesic, Antipyretic and Anti-Inflammatory Drugs in Remington's Science and Practice of Pharmacy (1995), 2:1207.
Harris et al., "Buprenorphine and Naloxone co-administration in opiate dependent patients stabilized on sublingual buprenorphine"; Drug and Alcohol Dependence (2000) vol. 61, pp. 85-94.
Hawkes et al., "Effect of enteric-release formulation of naloxone on intestinal transit in volunteers taking codeine"; Aliment Pharm Ther (2001) vol. 15, pp. 625-630.
Hiroshi K., et al., "Pharmacology," Hirokawa Bookstore, 1992, p. 70-72.
Hogger et al., "Comparison of tilidine/naloxone, tramadol and bromfenac in experimental pain: a double-blind randomized crossover study in healthy human volunteers"; International J. Clin Pharm and Thera (1999) vol. 37, No. 8,pp. 377-385.
Holmes et al., "Inhibiting Spinal Dynorphin A Component Enhances Intrathecal Morphine Antinociception in Mice", Anesth. Analg. (1993), 77:1166-73.
Holzer et al., "Opioid-induced bowel dysfunction in cancer-related pain: causes, consequences and a novel approach for its management," Journal of Opioid Management, 5(3): 145-151 (2009).
Hopp et al., "Pain 2: Oral prolonged-release (PR) oxycodone/naloxone combination reduces opiod-induced bowel dysfunction (OIBD) in chronic pain patients [abstract 40]," Presented at the 5th Research Forum of the European Association for Palliative Care, Palliat. Med., 22(4):441 (2008).
Hopp et al., "Analgesic efficacy of oxycodone in combination with naloxone as prolonged release (PR) tab lets in patients with moderate to severe chronic pain [abstract PT 226]," Presented at the 12th World Congress on Pain, International Association for the Study of Pain (IASP), Glasgow, Scotland, UK, MIS 4789879, Aug. 17-22, 2008.
Howes et al., "The Pharmacology of TR5109, a new Narcotic Agonist/Antagonist Analgesic"; NIDA Research (1979) pp. 99-105.
Hussain et al., "Buccal and oral bioavailability of naloxone and naltrexone in rats";(1987) vol. 36, pp. 127-130.
Jasinski et al., "The human pharmacology and abuse potential of N-allylnoroxymorphone naloxone"; J. Pharm and Exper Thera (1967) vol. 157, No. 2, pp. 420-426.
Jasinski D.R., "Assessment of the Abuse Potentiality of Morphine-like Drugs (Methods Used in Man)"; Drug Addiction (1977) pp. 197-258.
Johnson et al., "Buprenorphine and Naloxone for Heroin Dependence"; Substance Use Disorders (2000) pp. 519-526.
Jones et al., "Nalmefene:blockade of intravenous morphine challenge effects in opioid abuse in humans"; Drug and Alcohol Dependence (2000) vol. 60, pp. 29-37.
Judson et al., "The Naloxone Test for Opiate Dependence," Clin. Pharmacol. Ther., vol. 27, No. 4, pp. 492-501, (1980).
Kanof et al., "Levels of Opioid Physical Dependence in Heroin Addicts," Drug and Alcohol Dependence, 27 (1991) 253-262.
Kapoor, S., "Emerging New Therapeutic Options for the Management of Opioid Induced Constipation," J. of Pain and Palliative Case Pharmacotherapy, 24(1):98-99 (2010).
King et al., "Naltrexone Biotransformation and Incidence of Subjective Side Effects: A Preliminary Study"; Alcoholism: Clin and Exper Res (1997) vol. 21, No. 5, pp. 906-909.
Kogan et al., "Estimation of the Systemic Availability and Other Pharmacokinetic Parameters of Naltrexone in Man after Acute and Chronic Oral Administration"; Res. Comm. In Chem. Path. And Pharm (1977) vol. 18, No. 1, pp. 29-34.
Kosten et al., "Opioid antagonist challenges in buprenorphine maintained patients"; Drug and Alcohol Dependence (1990) vol. 25, OO. 73-78.
Kosten Thomas R., M.D.,"Buprenorphine for Benzodiazepine-Abusing Heroin Addicts"; Amer J of Psychiatry (1994) vol. 1, p. 151.
Kurland et al., "Naloxone and the Narcotic Abuser: A Cont oiled Study of Partial Blockade"; Inter. J. of the Addictions (1974) vol. 9, No. 5, pp. 663-672.

Krylov, Drug Register of Russia, Encyclopedia of Drugs, (2001) entries for "Nalbuphine," "Naloxone," and "Naltrexone" (English Translation).
Lapierre "Acetaminophen Boosts Liver Toxicity Alone, as Combination Therapy-Jama" Health News Daily, vol. 18 Issue 128 dated Jul. 6, 2006.
Latasch et al. [Treatment of morphine-induced constipation with oral naloxone]. Anaesthesist. Mar. 1997;46(3):191-4. (German with English Abstract) (448EP opposition).
Lee et al., "Nalbuphine Coadministered with Morphine Prevents Tolerance and Dependence"; Anesth Analg (1997) vol. 84, pp. 810-815.
Leeling et al., "Disposition and metabolism of codorphone in the rat, dog, and man"; Drug Metabolism and Disposition (1982) vol. 10, No. 6, pp. 649-653.
Lehman et al.,"Influence of Naloxone on the Postoperative Analgesic and Respiratory effects of Buprenorphine"; Eur. J. Clin Pharm (1988) vol. 34, pp. 343-352.
Levine et al., "Potentiation of Pentazocine Analgesia by Low-dose Naloxone"; J Clin Invest (1988) vol. 82, pp. 1574-1577.
Loimer et al., "Combined Naloxone/Methadone Preparations for Opiate Substitution Therapy"; J. of Substance Abuse Treatment (1991) vol. 8, pp. 157-160.
Lorcet, Physicians' Desk Reference 48th ed., 1994; pp. 2388-2390.
Lortab, Physicians' Desk Reference 48th ed., 1994; pp. 2498-2500.
Lowenstein et al., "Combined prolonged release oxycodone and naloxone improves bowel function in patients receiving opioids for moderate-to-severe non-malignant chronic pain: a randomized controlled trial," Expert Opinion on Pharmacotherapy, 10(4):531-543 (2009).
Martin et al. "Bioavailability Investigation of a New Tilidine/Naloxone Liquid Formulation Compared to a Reference Formulation";Arzneim-Forsch./Drug Res. (1999) vol. 49, pp. 599-607.
Martin et al., "Demonstration of Tolerance to and Physical Dependence on N-allynormorphine (Nalorphine)";J. of Pharm and Exper Thera (1965) vol. 150, No. 3. pp. 437-442.
Medzon, R, "Naltrexone and Nalmefene," Clinical Toxicology Review, vol. 19, No. 3, Dec. 1996.
Mendelson et al., "Buprenophine and naloxone Interactions in Methadone Maintenance Patients"; Society of Biological Psychiatry (1997) vol. 41, pp. 1095-1101.
Mendelson et al., "Buprenorphine and naloxone combinations: the effects of three dose ratios in morphine stabilized, opiate-dependent volunteers"; Psychopharmacology (1999) vol. 141, pp. 37-46.
Mendelson J., et al, "Buprenorphine and Naloxone Interactions in Opiate Dependent Volunteers," Clin. Phar. Ther. (1996), 60:105-114.
Miaskowski et al., "Inhibition of Spinal Opioid Analgesia by Supraspinal Administration of Selective Opioid Antagonists", Brain Research (1992), 596:41-45).
Mikus, G., "Combining Opioid Agonists and Antagonists as a Solution for Opioid-induced Constipation," European Gastroenterology and Hepatology Review, 4(2):71-74 (2008).
Mims, Jan. 2005, pp. 120-125.
Mollereau et al., "ORL 1, a novel member of the opioid receptor family: Cloning, functional expression and localization"; FEBS letters 341 (1994), pp. 33-38.
Muller-Lissner et al., "Oral Prolonged release (PR) oxycodone/naloxone combination reduced opioid-induced bowel dysfunction (OIBD) in patients with severe chronic pain (abstract 189)," Presented at the 2nd International Congress on Neuropathic Pain, Berlin, Germany, Published in Eur. J. Pain, 1 I (S1):S82, Jun. 7-10, 2007.
Mueller-Lissner, "Fixed Combination of Oxycodone with Naloxone: a New Way to Prevent and Treat Opioid-Induced Constipation." Adv. Ther. (2010) 27(9):581-590.
Mundipharma Clinical Studies Report A2-3759, "Validation of Bowel Function Index," Jun. 15, 2005 (Rev. Jul. 12, 2005).
Mundipharma Clinical Studies Report OXN 2401, "Optimization of Naloxone-Oxycodone Ration in Pain Patients." Jun. 3, 2005.
Nadstawek et al., "Patient assessment of the efficacy and tolerability of coadministered prolonged release oral oxycodone and naloxone in severe chronic pain (abstract SAT0375)," Presented at the 8th Annual

(56) References Cited

OTHER PUBLICATIONS

European League Against Rheumatism (EULAR 2007), Barcelona, Spain, Published in Ann. Rheum. Dis., 66(Suppl. 2):543, Jun. 13-16, 2007.
Nichols et al., "Improved bowel function with a combination of oxycodone and naloxone (OXN) as prolonged-release (PR) tablets in patients with moderate to severe chronic pain (abstract PT225)," Presented at the 12th World Congress on Pain, International Association for the Study of Pain (IASP), Glasgow, Scotland, UK, Aug. 17-22, 2008.
Nolte, T., "Prolonged-release oxycodone/naloxone is effective and safe in clinical use (abstract 275)," Encore presentation at the 5th Research Forum of the European Association for Palliative Care, Published in Palliative Medicine, 22(4):484-5 (2008).
Nolte, T., "Prolonged-release oxycodone/naloxone is effective and safe in cancer pain (abstract 66)," Encore presentation at the 12th World Congress on Pain, International Association for the Study of Pain (IASP), Glasgow, Scotland, UK, Aug. 17-22, 2008.
Nolte, T., "Prolonged-release oxycodone/naloxone is effective and safe in clinical use (abstract PO325)," Presented at the 28th German Congress on Cancer, Published in Onkologie, Berlin, Germany, 31(Suppl. 1):165-6, Feb. 20-23, 2008.
Nutt et al., "Methadone-naloxone mixture for use in methadone maintenance programs"; Clin Pharm and Ther. vol. 15, No. 2., pp. 156-166 (1974).
Pamuk et al., "Revalidation of description of constipation in terms of recall bias and visual scale analog questionnaire," Journal of Gastroenterology and Hepatology (2003), 18, 1417-1422.
Paronis et al., "Increased Analgesic Potency of Mu Agonists after Continuous Naloxone Infusion in Rats"; J for Pharm Exper Thera (1991), 259 (2), pp. 582-589.
Parwartikar et al., "Naloxone-Methadone Combination for the Treatment of Opiate Dependence"; Missouri Institute of Psychiatry, pp. 1350-1354, (1973).
Parwatikar et al., "Methadone-naloxone in combination for the Treatment of Heroin Addicts"; Clin. Pharm and Thera, vol. 14, No. 6, pp. 941-948, (1973).
Peachey et al., "Assessment of Opioid Dependence with Naloxone," British Journal of Addiction (1988) 83(2), 193-201.
Physician's Desk Reference (2001) see "Revia," pp. 1146-1149.
Physician's Desk Reference (2001) see "Oxycontin," pp. 2697-2701.
Physician's Desk Reference 48th ed.; 1994; "Talwin," 2120-2121, Montvale, NJ.
Pitts et al., "Antinociceptive and Response Rate-Altering Effects of Kappa Opioid Agonists, Spiradoline, Enadoline and U69,593, Alone and in Combination with Opioid Antagonists in Squirrel Monkeys"; J of Pharm and Exper Thera (1994) vol. 271, No. 3, pp. 1501-1508.
Press Release "International Patent Application to Be Published on Abuse-Resistant Pain Reliever Being Developed by Perdue Pharma"; Aug. 8, 2001.
Preston et al., "Abuse liability and studies of opioid agonist-antagonists in humans"; Drug and Alcohol Dependence (1991) vol. 28, pp. 49-82.
Preston et al., "Buprenorphine and Naloxone alone and in combination in Opioid-dependant Humans"; Psychopharmacology (1988), vol. 94, pp. 484-490.
Preston et al., "Differential Naltrexone Antagonism of Hydromorphone and Pentazocine Effects in Human Volunteers"; J of Pharm and Ezper Thera (1993) vol. 264, No. 2 pp. 813-823.
Preston et al., "Effects of Sublingually given naloxone in Opioid-dependant human volunteers"; Drug and Alcohol Dependence (1990) vol. 25, pp. 27-34.
Rapaka et al., "Discovery of Novel Opioid Medications"; NIDA Research Monograph 147 (1995) p. 55-83.
Reimer et al., "Meeting the challenges of opioid-induced constipation in chronic pain management—a novel approach," Pharmacology, 83:10-17 (2009).
Rentz et al., "Validation of the Bowel Function Index to detect clinically meaningful changes in opioid-induced constipation," Journal of Medical Economics (JME), 12(0):371-383 (2009).
Resnick et al., "Naloxone Precipitated Withdrawal: A Method for Rapid Induction Onto Naltrexone," Clinical Pharmacology and Therapeutics, vol. 21, No. 4, pp. 409-413; received for publication Nov. 16, 1976.
Richter et al., "Clinical Investigation on the Development of Dependence during Oral Therapy with Tramadol"; Arzniem-Forsch/Drug Res. 35 (No. II)(1985)pp. 1742-1744.
Rosen et al., "A Pilot Study of Dextromethorphan in Naloxone-Precipitated Opiate Withdrawal"; European J. of Pharm. (1996) vol. 307, pp. 251-257.
Rosen et al., "The effect of Lamotrigine on Naloxone-precipitated Opiate withdrawal"; Drug and Alcohol Dependence (1998) vol. 52, pp. 173-176.
Sandner-Kiesling et al., "Long-term efficacy and safety of combined prolonged-release oxycodone and naloxone in the management of non-cancer chronic pain," International Journal of Clinical Practice, 64(6):763-774 (2010).
Schuh et al., "Buprenorphine, Morphine and Naloxone Effects during Ascending Morphine Maintenance in Humans"; J. Pharm and Exper Thera (1996) vol. 278, 2, pp. 836-846.
Schuh et al., "Onset, Magnitude and Duration of Opioid Blockade Produced by Buprenorphine and Naltrexone in Humans"; Psychopharmacology (1999) vol. 145, pp. 162-174.
Schutter et al., "Innovative pain therapy with a fixed combination of prolonged-release oxycodone/naloxone: a large observational study under conditions of daily practice," Current Medical Research and Opinion, 26(6):1377-1387 (2010).
Schmidt, W.K. "Alvimopan (ADL 8-2698) Is a Novel Peripheral Opioid Antagonist," The American Journal of Surgery, 182 (Suppl. to Nov. 2001) 27S-38S (2001).
Shen et al., "Ultra-Low Doses of Naltrexone or Etorphine Increase Morphine's Antinocieceptive Potencey and Attenuate Tolerance/Dependence in Mice," Brain Research (1997), 757:176-190.
Shin Yakuzaigaku Soron (3rd revised edition), 1987, p. 148-151.
Simpson et al., "Fixed-ratio combination oxycodone/naloxone compared with oxycodone alone for the relief of opiod induced constipation in moderate-to-severe non-cancer pain," Current Medical Research and Opinion (CMRO), 24(12):3503-3512 (2008).
Smith et al., "Single and multiple-dose pharmacokinetic evaluation of oxycodone and naloxone in an opioid agonist/antagonist prolonged-release combination in healthy adult volunteers," Clinical Therapeutics, 30(11):2051-2068 (2008).
Smith et al., "Prolonged-release oxycodone/naloxone tablets: Dose-proportional pharmacokinetics (abstract PW 256)," Presented at the 12th World Congress on Pain, International Association for the Study of Pain (IASP), Glasgow, Scotland, UK (MIS 4790606), Aug. 17-22, 2008.
Stevens et al., Nonspecific Excitatory Effects of Morphine: Reverse-Order Precipitated Withdrawal and Dose-Dose Interactions: Psychopharmacology (1981) vol. 75, pp. 210-211.
Stine et al., "Reduction of Opiate Withdrawal-like Symptoms by Cocaine Abuse during Methadone and Buprenorphine Maintenance"; Am. J. Drug and Alcohol Abuse (1994) vol. 20, 4, pp. 445-458.
Stine et al., "Use of Drug Combinations in Treatment of Opioid Withdrawal"; J. Clinical Psych. (1992) vol. 12, No. 3, pp. 203-209.
Stoller et al., "Effects of buprenorphine/naloxone in opioid-dependent humans" Psychopharmacology.(2001) vol. 154, pp. 230-242.
Strain et al., "Acute Effects of Buprenorphine, hydromorphone and naloxone in methadone-maintained volunteers"; J. Pharm and Exper Thera (1992) vol. 261, No. 3, pp. 985-993.
Strain et al., "Effects of buprenorphine versus buprenorphine/naloxone tablets in non-dependent opiod abusers"; Psychopharmacology (2000) vol. 148, pp. 374-383.
Strain et al., "Opioid antagonist effects of dezocine in opioid-dependent humans"; Clin Pharm and Thera (1996) vol. 60, No. 2, pp. 206-217.
Strain et al., "Precipitated Withdrawal by Pentazocine in Methadone-Maintained Volunteers"; J. Pharm and Exper Thera (1993) vol. 267, No. 2, pp. 624-634.
Sunshine et al., "Analgesic Efficacy of Pentazocine Versus a Pentazocine-Naloxone Combination Following Oral Administration," Clin. J. Pain (1988), 4:35-40.

(56) References Cited

OTHER PUBLICATIONS

Suzuki et al., "Morphine conditioned place preference after chronic treatment with naloxone in the rat"; Research Communications in Substance Abuse (1991) vol. 12., No. 3., pp. 119-131.
Sykes "Oral naloxone in opioid-associated constipation," Lancet (1991) vol. 337 p. 1475.
Sykes "An investigation of the ability of oral naloxone to correct opioid-related constipation in patients with advanced cancer," Palliative Medicine (1996), 10:134-144.
Tai et al., "Naltrexone: An Antagonist Therapy for Heroin Addiction"; NIDA (1997) 5 pages.
U.S. Appl. No. 10/510,673: Final Office Action dated Jan. 11, 2011, (21 pages).
U.S. Appl. No. 10/510,673: Non-Final Office Action dated Apr. 15, 2008, including PTO Form 892 (13 pages).
U.S. Appl. No. 10/510,673: Non-Final Office Action dated Apr. 27, 2010, including PTO Form 892 (17 pages).
U.S. Appl. No. 10/510,673: Non-Final Office Action dated Jun. 2, 2009, (15pages).
Umbricht et al., "Naltrexone shortened opioid detoxification with buprenorphine"; Drug and Alcohol Dependence (1999) vol. 56 pp. 181-190.
Vaccarino et al., "Endogenous Opiates: 1999"; Peptides 21 (2000) pp. 1975-2034.
Vaccarino et al.,"Analgesia Produced by Normal Doses of Opioid Antagonists Alone and in Combination with Morphine", Pain (1989), 36:103-109.
Vicodin, Physicians' Desk Reference 48th ed., 1994; pp. 1143-1145.
Walsh et al., "Effects of Naltrexone on Response to Intravenous Cocain, Hydromorphone and their Combination in Humans," (1996).
Wang et al., "Crossover and Parallel Study of Oral Analgesics," J. Clin. Pharmacol (1981), 21:162-168.
Wang et al., "Inverse Agonists and neutral antagonists at mu opioid receptor (MOR): possible role of basal receptor signaling in narcotic dependence"; J. Neurochemistry (2001) vol. 77, pp. 1590-1600.
Wang et al., "Rating the Presence and Severity of Opiate Dependence," Clinical Pharmacology and Therapeutics, vol. 16, No. 4, pp. 653-657; received for publication Jan. 21, 1974.
Wang et al., "cDNA cloning of an orphan opiate receptor gene family member and its splice variant"; FEBS letters 348 (1994) pp. 75-79.
Watkins et al. "Aminotransferase Elevations in Healty Adults Receiving 4 Grams of Acetaminophen Daily" Jama, Jul. 5, 2006 vol. 296 No. 1.
Way et al., "Responsivity to Naloxone during Morphine Dependence"; Annals New York Academy of Sciences, pp. 252-261, (1976).
Weinberg et al., "Sublingual absorption of selected opioid analgesics"; Clin Pharm Thera (1988) vol. 44, No. 3, pp. 335-342.
Weinhold et al., "Buprenorphine Alone and in Combination with Naltrexone in Non-Dependent Humans," Drug and Alcohol Dependence (1992), 30:263-274.
Wells et al., "In vivo Pharmacological Characterization of SoRI 9409, a Nonpeptidic Opioid—Agonist/—Antagonist that Produces Limited Antinociceptive Tolerance and Attenuates M orphione Physical Dependence"; J. Pharm and Exper Thera (2001) vol. 297, No. 2, pp. 597-605.
Wiesen et al., "The Safety and Value of Naloxone as a Therapeutic Aid," Drug and Alcohol Dependence, 2 (1977) pp. 123-130.
Wikler et al., "N-Allylnormorphine: Effects of single dose and Precipitation of Acute "Abstinence Syndromes" during addiction to morphine, methadone or heroin in man (post addicts)"; N-Allylnormorphine During Narcotic Addiction (1953) pp. 8-20.
Wilmington, Del., PR Newswire; New Data Published Describing Favorable Safety Profile of REVIA (Naltrexone Hydrochloride Tablets) When Used to Treat Alcohol Dependence,' Dec. 1997.
Wodak Alex, "Drug Treatment for Opioid Dependence"; Australian Prescriber (2001) vol. 24, No. 1, pp. 4-6.
Woodward et al., "Prolonged-release oxycodone/naloxone tablets: Pharmacokinetics in the elderly (abstract)," Present ed at the 12th World Congress on Pain, International Association for the Study of Pain (IASP), Glasgow, Scotland, UK, Abstract PW 255, (MIS 4789067), Aug. 17-22, 2008.
Wright et al., "Acute physical dependence in Humans; repeated naloxone-precipitated withdrawal after a single-dose of methadone"; Drug and Alcohol Dependence (1991) vol. 27, pp. 139-148.
Yoburn et al., "Opioid Antagonist-induced Receptor Upregulation: Effects of Concurrent Agonist Administration"; Brain Research Bulletin (1994), vol. 33, pp. 237-240.
Yoburn et al., "Supersensitivity to Opioid Analgesics Following Chronic Opioid Antagonist Treatment: Relationship to Receptor Sensitivity"; Pharmacology Bio Beh (1995) vol. 51 No. 2, pp. 535-539.
Yuan et al., "Efficacy of Orally Administered Methylnaltrexone in Decreasing Subjective Effects After Intravenous Morphine", Drug and Alcohol Dependence (1998); 52:161-165.
Yuan et al., "The Safety and Efficacy of Oral Methylnaltrexone in Preventing Morphine-induced Delay in Oral-Cecal Transit Time", Clinical Trials and Therapeutics (1997), 61:467-475.
Zaks et al., "Naloxone Treatment of Opiate Dependence"; JAMA (1971) vol. 215, No. 13, pp. 2108-2110.
Zhang et al., "Down-Regulation of -Opioid Receptors in Rat and Monkey Dorsal Root Ganglion Neurons and Spinal Cord After Peripheral Axotomy"; Neuroscience (1998) vol. 82., pp. 223-240.
Zhu et al., "Naltrexone-precipitated morphine withdrawal in infant rat is attenuated by acute administration if NOS inhibitors but not NMDA receptor antagonists"; Psychopharmacology (2000) vol. 150, pp. 325-336.
European Patent No. EP1492506: May 10, 2010 Patentee reply to Notice of Opposition.
European Patent No. EP1492506: May 26, 2011 Summons to attend oral proceedings.
European Patent No. EP1492506: Sep. 5, 2011 written submissions of Hexal AG.
European Patent No. EP1492506: Sep. 9, 2011 written submissions of patentee.
European Patent No. EP1492506: Dec. 16, 2011 Minutes of Oral Proceedings and Decision of the Opposition Division.
European Patent No. EP1492506: Apr. 16, 2012 grounds of appeal of Hexal AG.
European Patent No. EP1492506: Apr. 25, 2012 grounds of appeal of patentee.
EP Application No. 03720424.5: Official Action dated Jun. 6, 2012.
EP Application No. 10176720.0: Official Action dated Jun. 11, 2012.
EP Application No. EP05020579.8: Communication forwarding the European Search Report dated Feb. 7, 2006.
EP Application No. EP05020579.8: Sep. 20, 2006 Response.
EP Application No. EP05020579.8: Jun. 6, 2012 Official Action.
EP Application No. EP05020580.6: Communication forwarding the European Search Report dated Feb. 8, 2006.
EP Application No. EP05020580.6: Sep. 20, 2006 Response.
EP Application No. EP05020580.6: Jun. 8, 2012 Official Action.
EP Application No. EP10160827.1: Official Action dated Jan. 11, 2011.
EP Application No. EP10176078.3: Communication forwarding the European Search Report dated Mar. 8, 2011.
EP Application No. EP10176078.3: Jan. 26, 2012 Request for Further Processing.
EP Application No. EP10176078.3: Jun. 11, 2012 Official Action.
EP Application No. EP10180494.6: Communication forwarding the European Search Report dated Mar. 9, 2011.
EP Application No. EP10180494.6: Oct. 18, 2011 Response.
EP Application No. EP10180494.6: Jun. 13, 2012 Communication pursuant to Article 94(3) EPC.
EP Application No. EP10180495.3: Communication forwarding the European Search Report dated Feb. 25, 2011.
EP Application No. EP10180495.3: Oct. 13, 2011 Response.
EP Application No. EP10180495.3: Jun. 14, 2012 Official Action.
EP Application No. EP10180496.1: Communication forwarding the European Search Report dated Mar. 9, 2011.
EP Application No. EP10180496.1: Oct. 27, 2011 Response.
EP Application No. EP10180496.1: Jun. 13, 2012 Official Action.
EP Application No. EP10180498.7: Communication forwarding the European Search Report dated Mar. 9, 2011.

(56) References Cited

OTHER PUBLICATIONS

EP Application No. EP10180498.7: Oct. 27, 2011 Response.
EP Application No. EP10180498.7: Jun. 13, 2012 Official Action.
EP Application No. EP11177513.6: European Search report and Search opinion dated Feb. 2, 2012.
EP Application No. EP11177516.9: European Search report and Search opinion dated Feb. 2, 2012.
EP Application No. EP11177518.5: European Search report and Search opinion dated Feb. 2, 2012.
EP Application No. EP11177520.1: European Search report and Search opinion dated Feb. 2, 2012.
AR Application No. P20030101201: Official Action dated Jul. 13, 2012 (English Translation).
IL Application No. 200621: Official Action dated Apr. 29, 2012 (English Translation).
JP Application No. 2009-61144: Official Action dated Feb. 14, 2012 (English Translation).
JP Application No. 2010-088165: Official Action dated Oct. 2, 2012 (English Translation).
PCT Application PCT/EP2003/003541: International Preliminary Examination Report dated Jul. 6, 2004.
EP Application No. EP06111805.5: Jul. 10, 2008 Response to Office Communication dated Feb. 19, 2008, p. 1-155.
Kreek et al., "Drug Interactions with Methadone," *Ann. N.Y. Acad. Sci.*, 281, 350-371 (1976).
Package Insert for OxyContin®, Purdue Pharma L.P. (Mar. 18, 2004) p. 1-31.
Pappagallo, M., "Incidence, prevalence, and management of opioid bowel dysfunction," Am. J. Surg. (2001) 182 suppl. 11S-18S.
Sykes, N P., "Using Oral Naloxone in Management of Opioid Bowel Dysfunction," in Handbook of Opioid Bowel Syndrome, Chapter 9, (Yuan, C.-S. ed.,The Haworth Medical Press 2005), p. 175-195.

\* cited by examiner

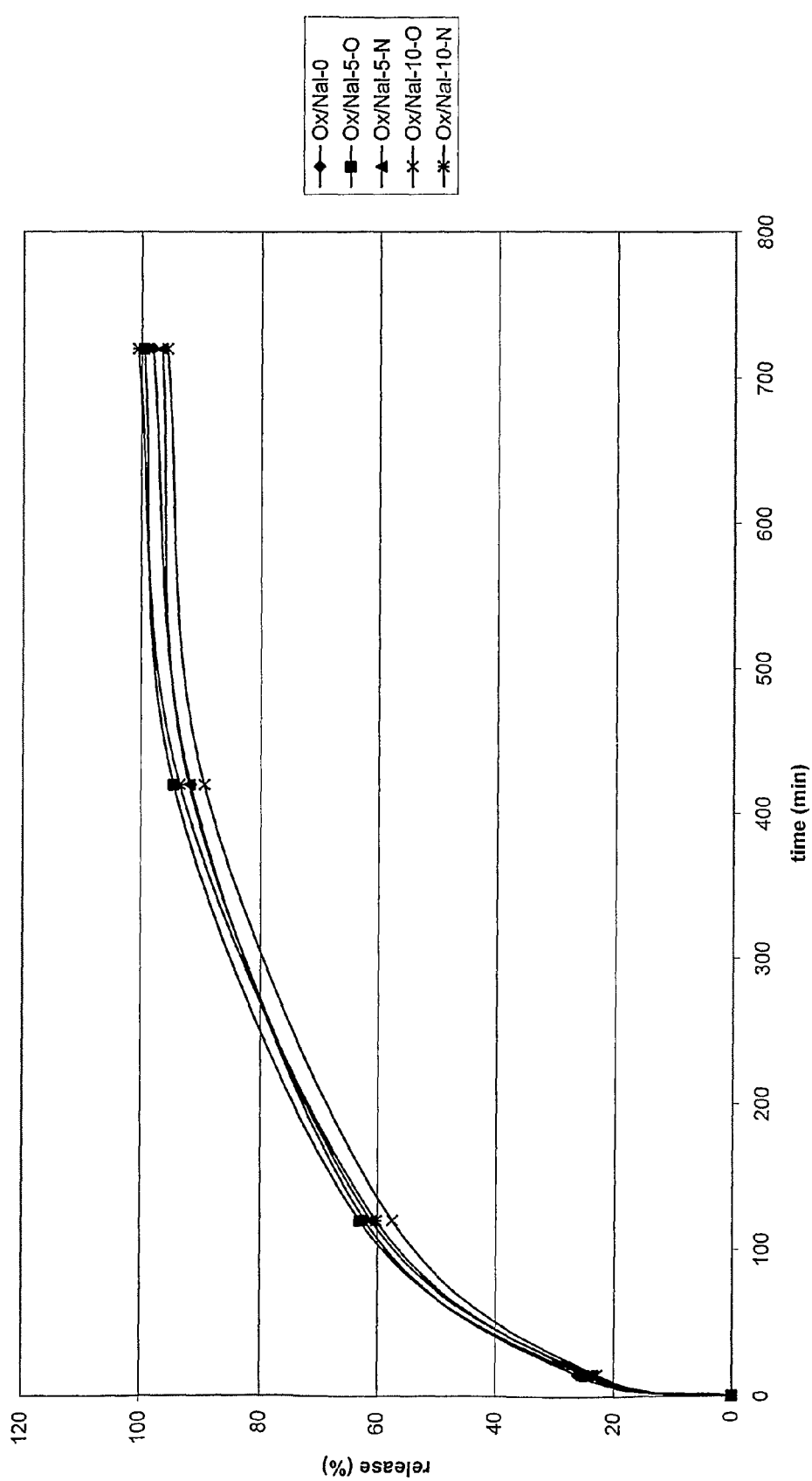

Figure 5A: Surface of a Ox/Nal-10 tablet at 25x magnification. The voltage was 10 kV. The bar length corresponds to 2 mm.
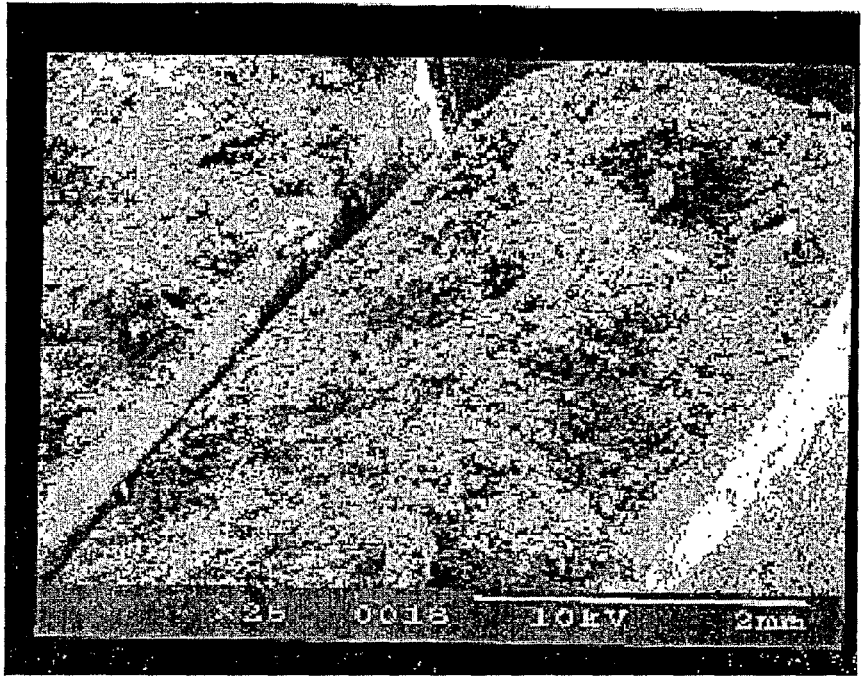
Figure 5B: Surface of a Ox/Nal-10 tablet at 200x magnification. The voltage was 10 kV. The bar length corresponds to 200 µm.
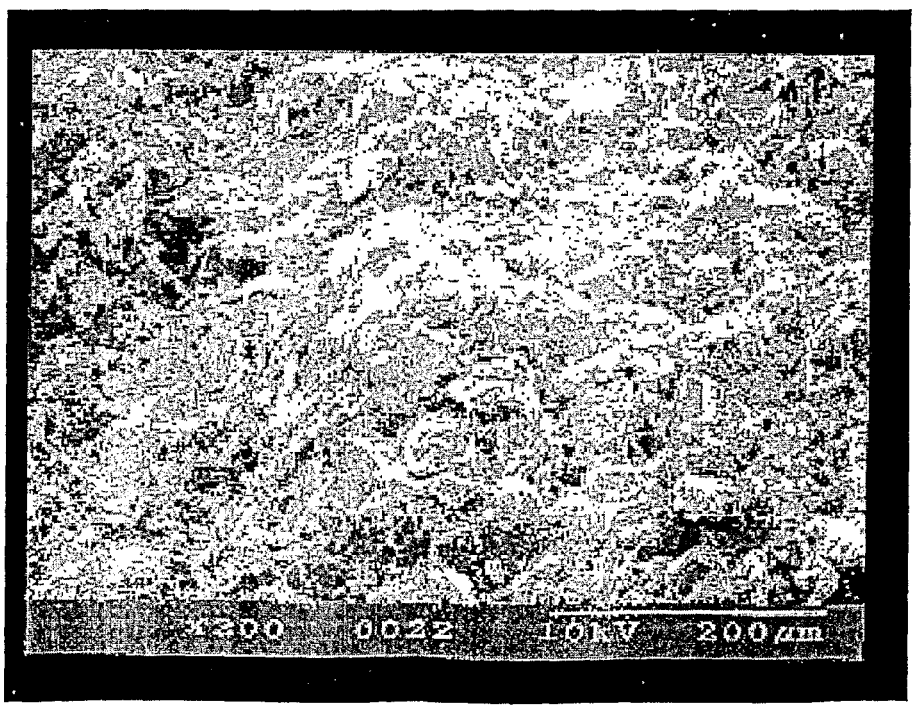

Figure 6A: Surface of a Oxy/Nal-Extr tablet at 40x magnification. The voltage was 10 kV. The bar length corresponds to 700 μm.
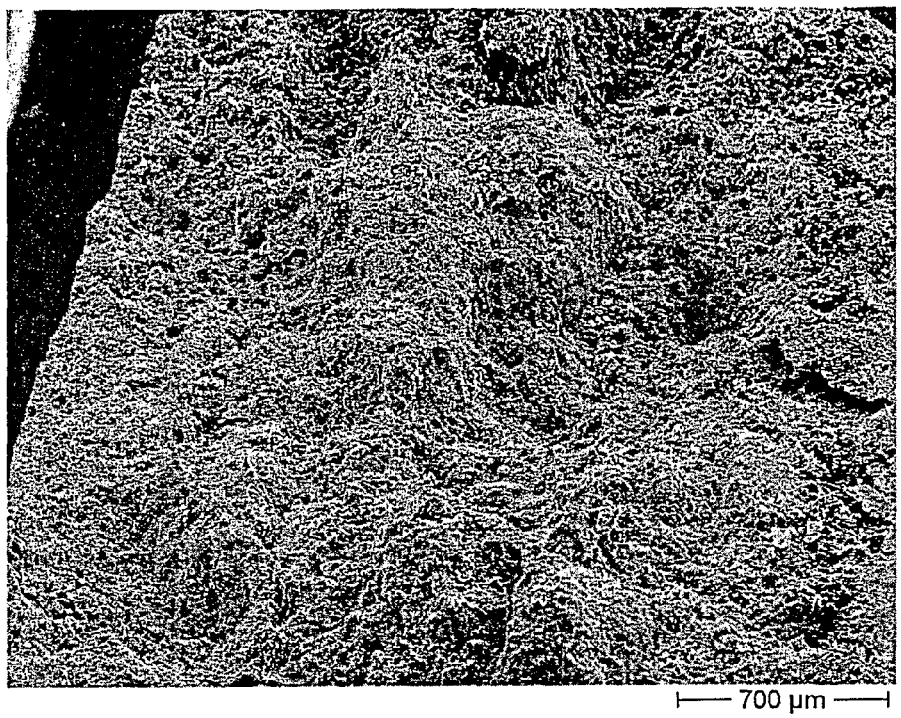
Figure 6B: Surface of a Oxy/Nal-Extr tablet at 200x magnification. The voltage was 10 kV. The bar length corresponds to 300 μm.
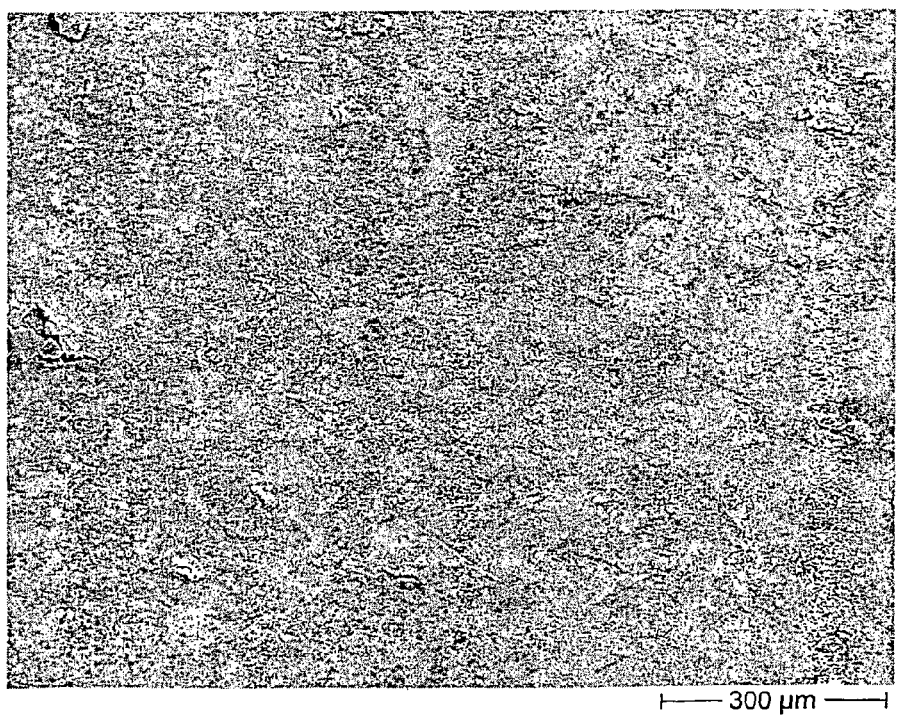

Figure 7A: Surafce of a Valoron® N tablet at 25x magnification. The voltage was 10 kV. The bar length corresponds to 2 mm.
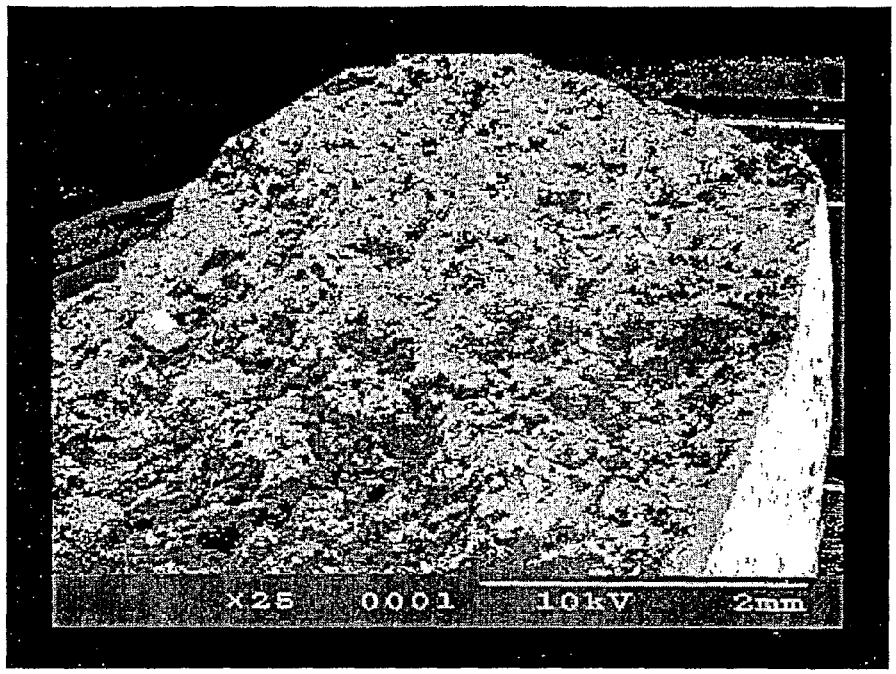
Figure 7B: Surface of a Valoron® N tablet at 100x magnification with crystal(Tilidine, down left). The voltage was 10 kV. The bar length corresponds to 500 μm.
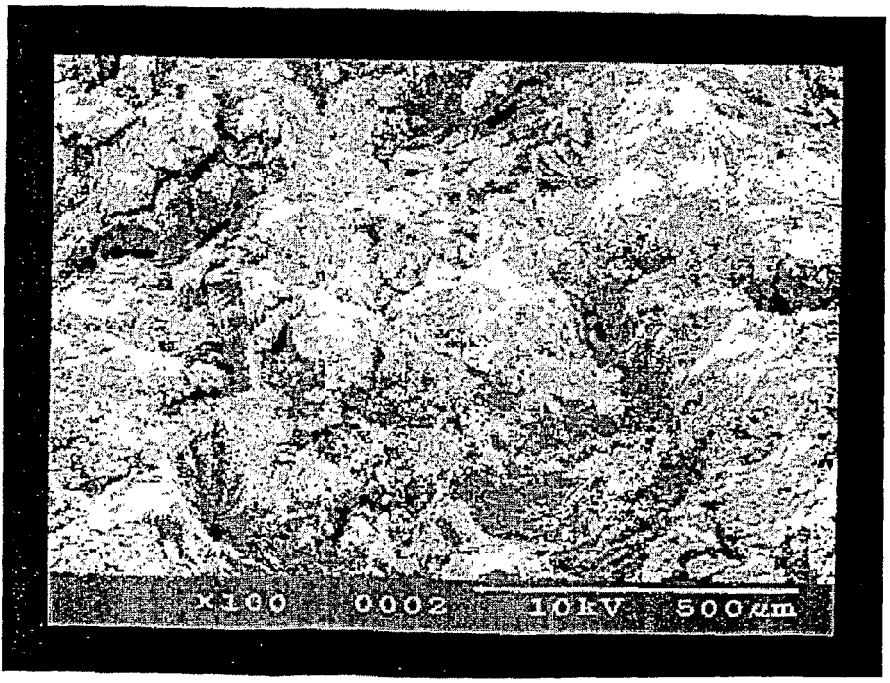

Figure 10A: Surface of a NaI-5-Eud tablet at 25x magnification- The voltage was 10 kV. The bar length corresponds to 2mm.
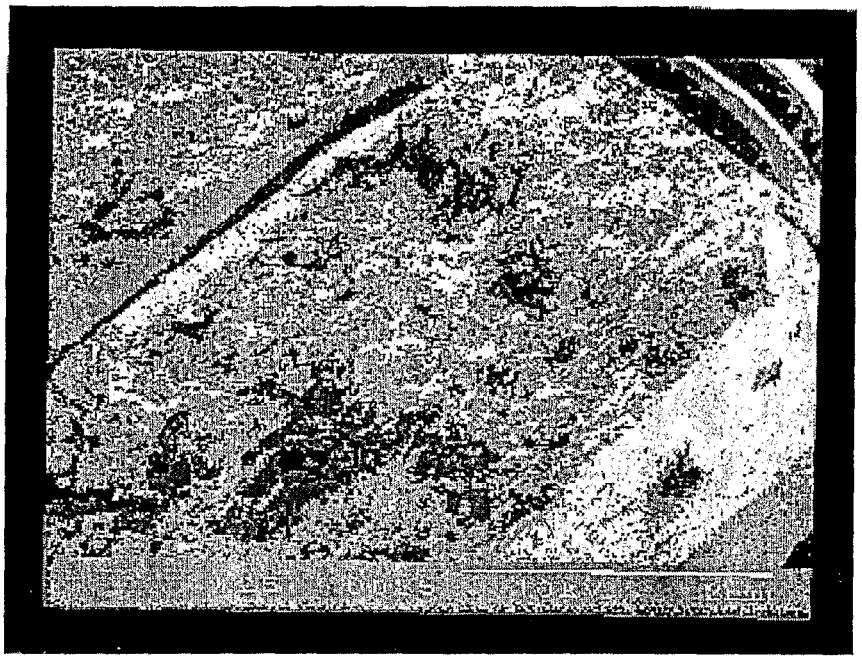
Figure 10B: Surface of a NaI-5-Eud tablet at 200x magnification. The voltage was 10 kV. The bar length corresponds to 200μm.
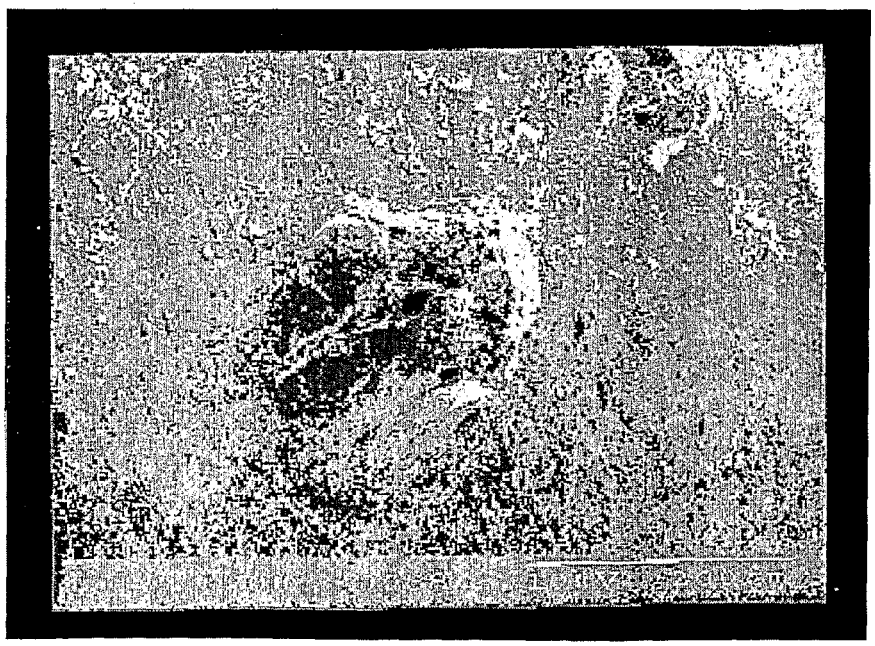

Figure 11A: Surface of a Nal-Extr tablet 25x magnification. The voltage was 10 kV. The bar length corresponds to 2mm.
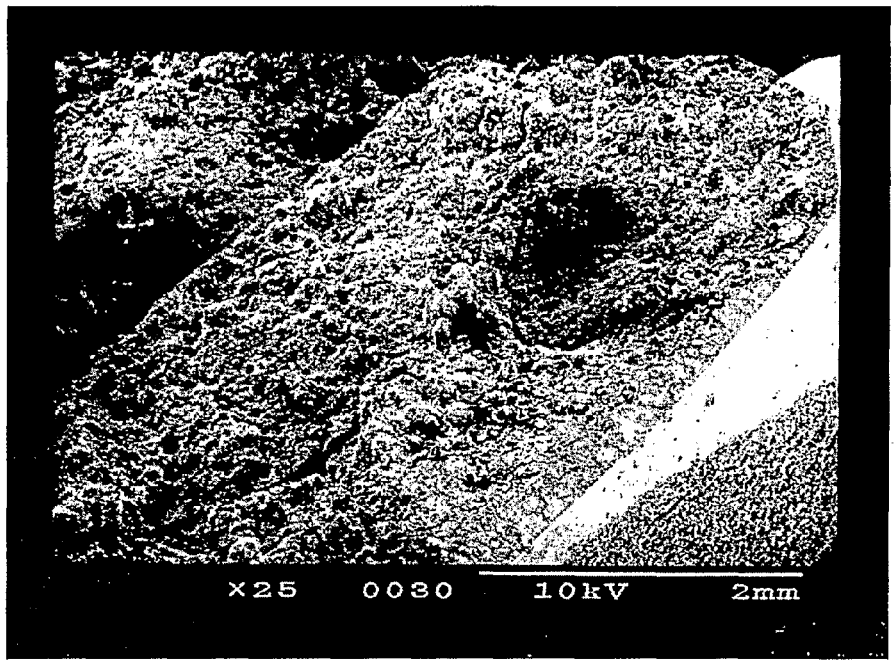
Figure 11B: Surface of a Nal-Extr tablet at 200x magnification. The voltage was 10 kV. The bar length corresponds to 200 µm.
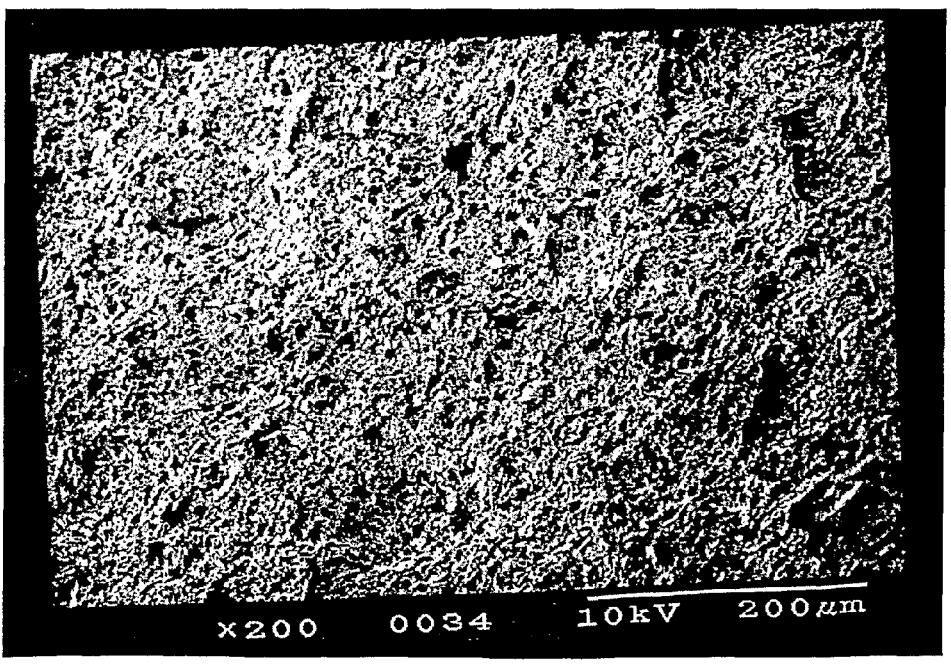

Figure 12A: Surface of Nal-10-Sure granulates at 30x magnification. The voltage was 10 kV. The bar length corresponds to 1mm.
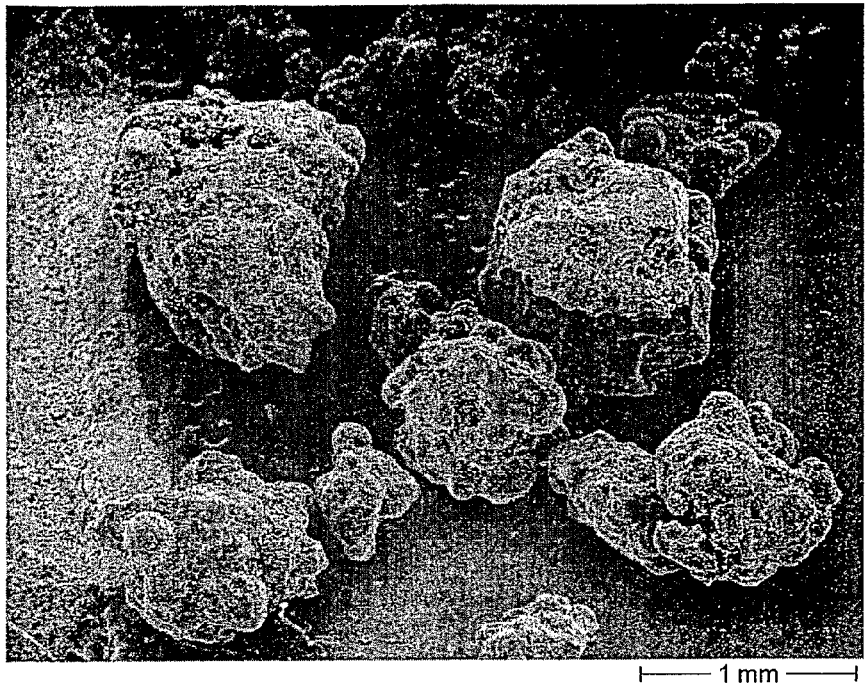
Figure 12B: Surface of Nal-10-Sure granulates at 200x magnification. The voltage was 10 kV. The bar length corresponds to 100 μm.
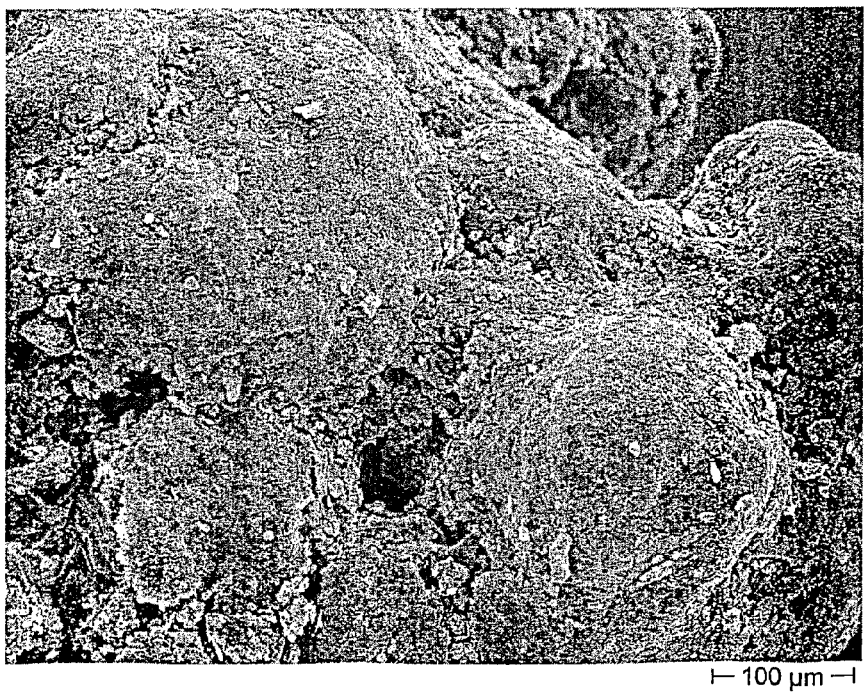

Figure 13A: Surface of NaI-Extr granulates at 30x magnification. The voltage was 10 kV. The bar length corresponds to 1 mm.
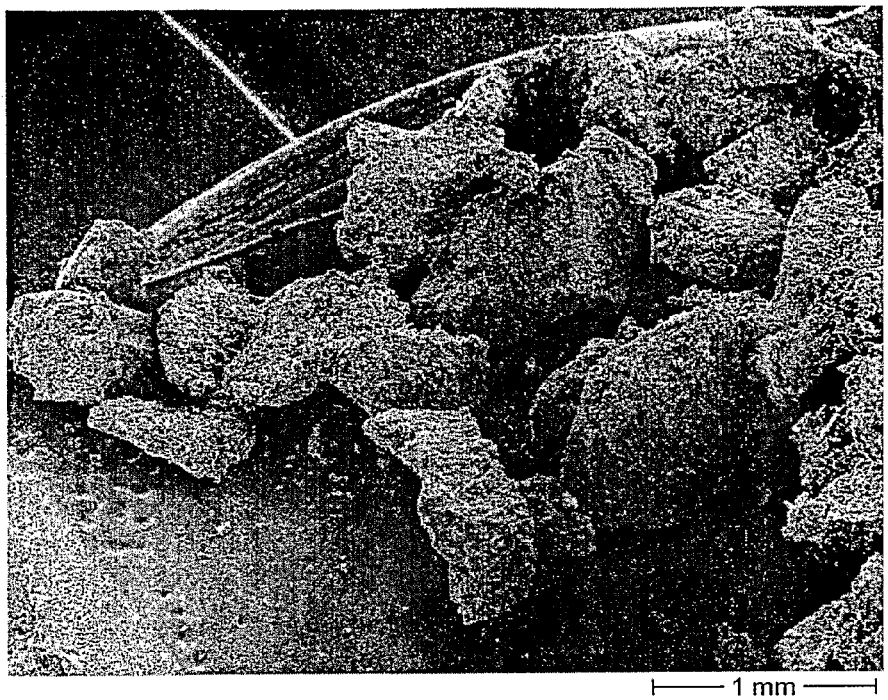
Figure 13B: Surface of NaI-Extr granulates at 200x magnification. The voltage was 10 kV. The bar length corresponds to 100 μm.

MATRIX FOR SUSTAINED, INVARIANT AND INDEPENDENT RELEASE OF ACTIVE COMPOUNDS

1. CROSS REFERENCE TO RELATED APPLICATIONS

This application is a continuation of application Ser. No. 10/510,673, now abandoned, which is a national stage entry of International Application No. PCT/EP03/03541, filed Apr. 4, 2003, which claims priority under 35 U.S.C. §§119(a)-(d) and 365(b) of German Patent Application Nos. 102 15 067.2 and 102 15 131.8, filed Apr. 5, 2002, the contents of all of which are incorporated herein by reference.

2. BRIEF DESCRIPTION OF THE DRAWINGS

Figure 1B:
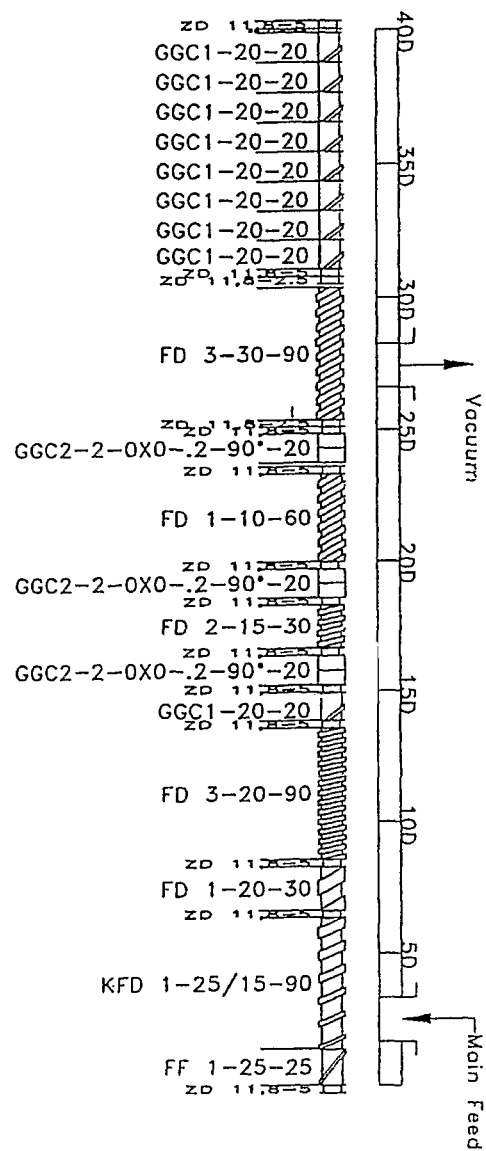

FIGS. 1A-1B: FIG. 1A provides the screw geometry of the extruder of Example 2. FIG. 1B provides the screw geometry of the extruder of Example 8.

FIG. 2: provides the release profile of the oxycodone/naloxone tablets from Example 1.

Figure 3A:
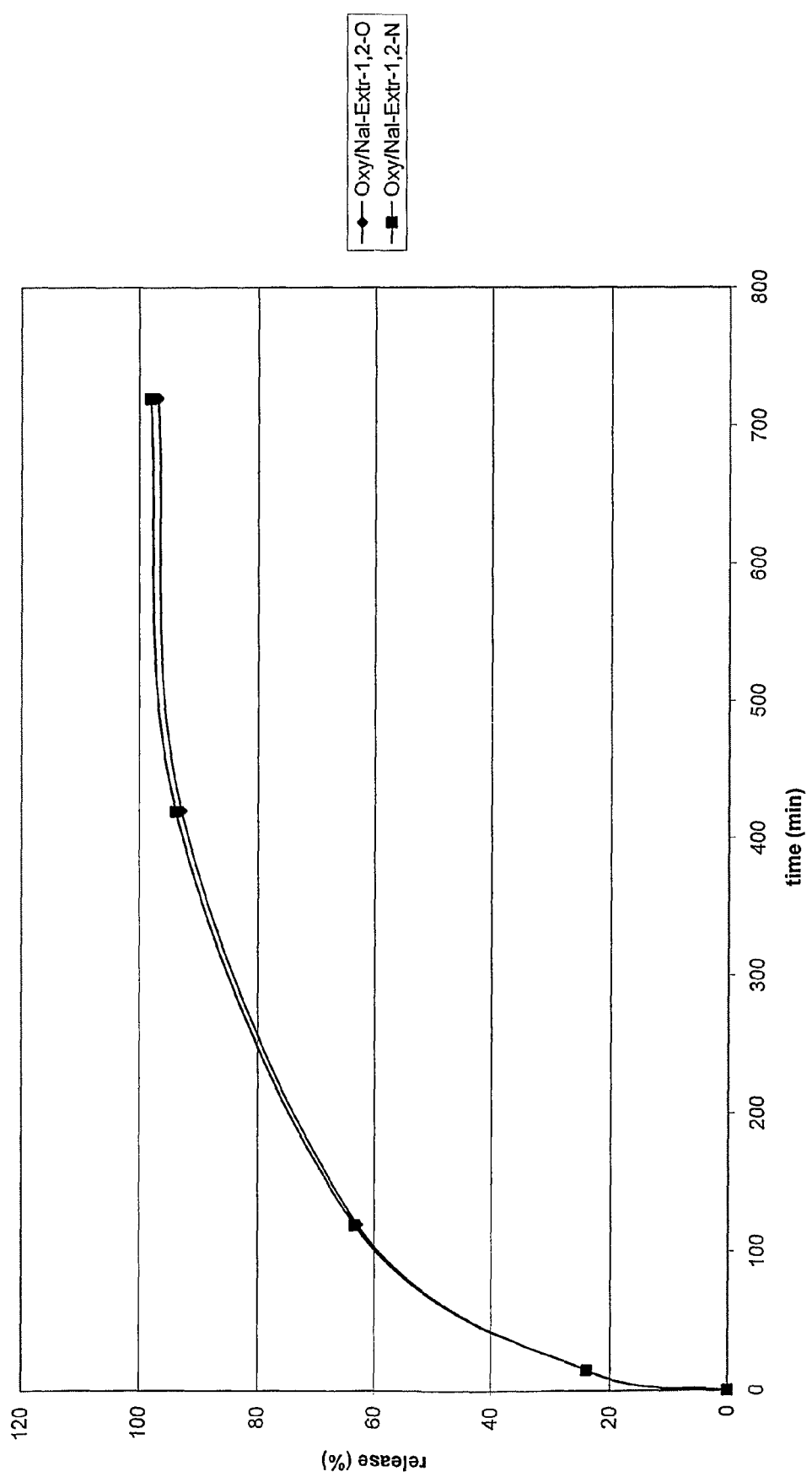
Figure 3B:
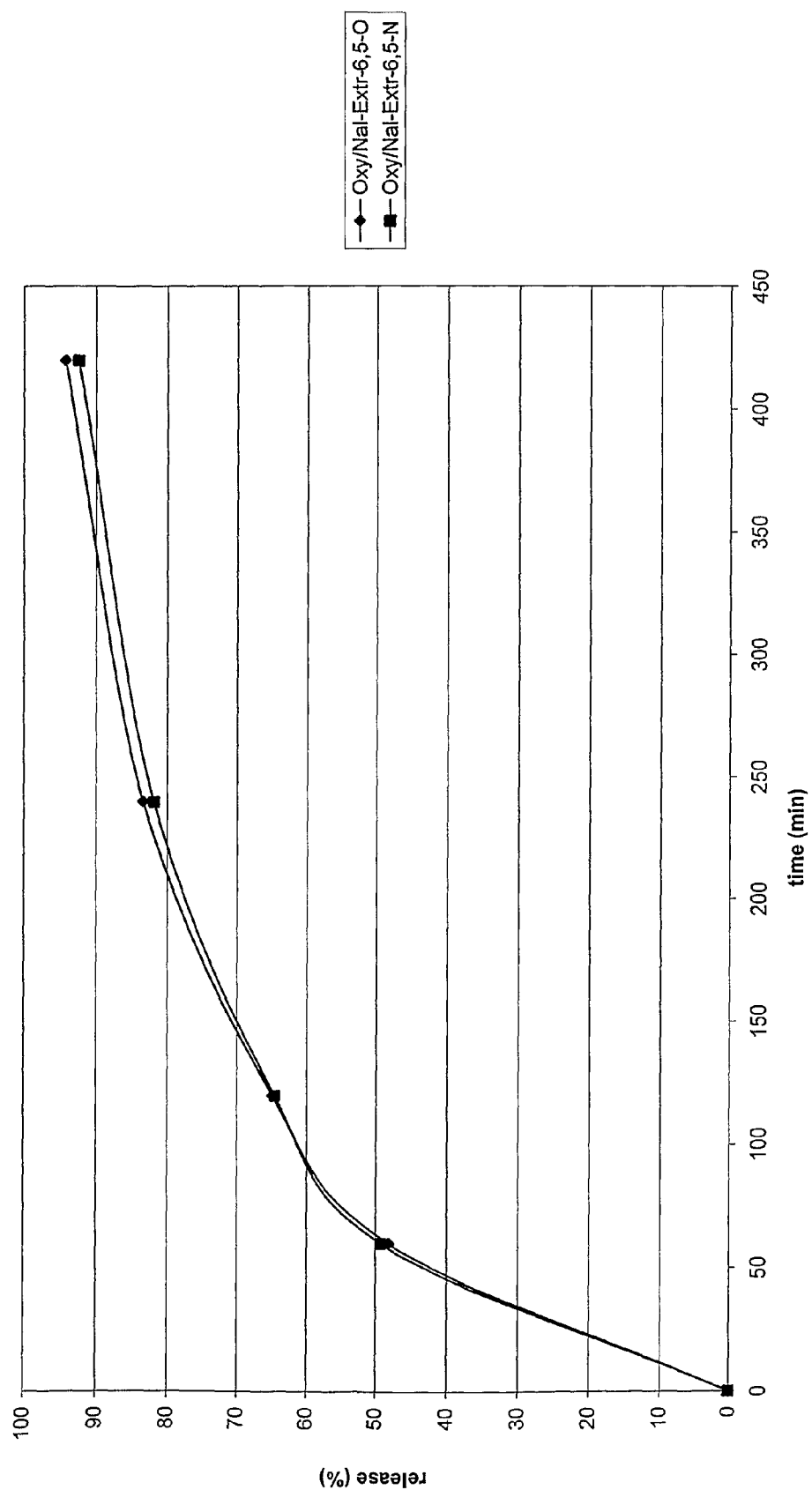

FIGS. 3A-3B: FIG. 3A provides the release profile of the oxycodone/naloxone tablets from Example 2 at pH 1.2. FIG. 3B provides the release profile of the oxycodone/naloxone tablets from Example 2 at pH 6.5.

Figure 4A:
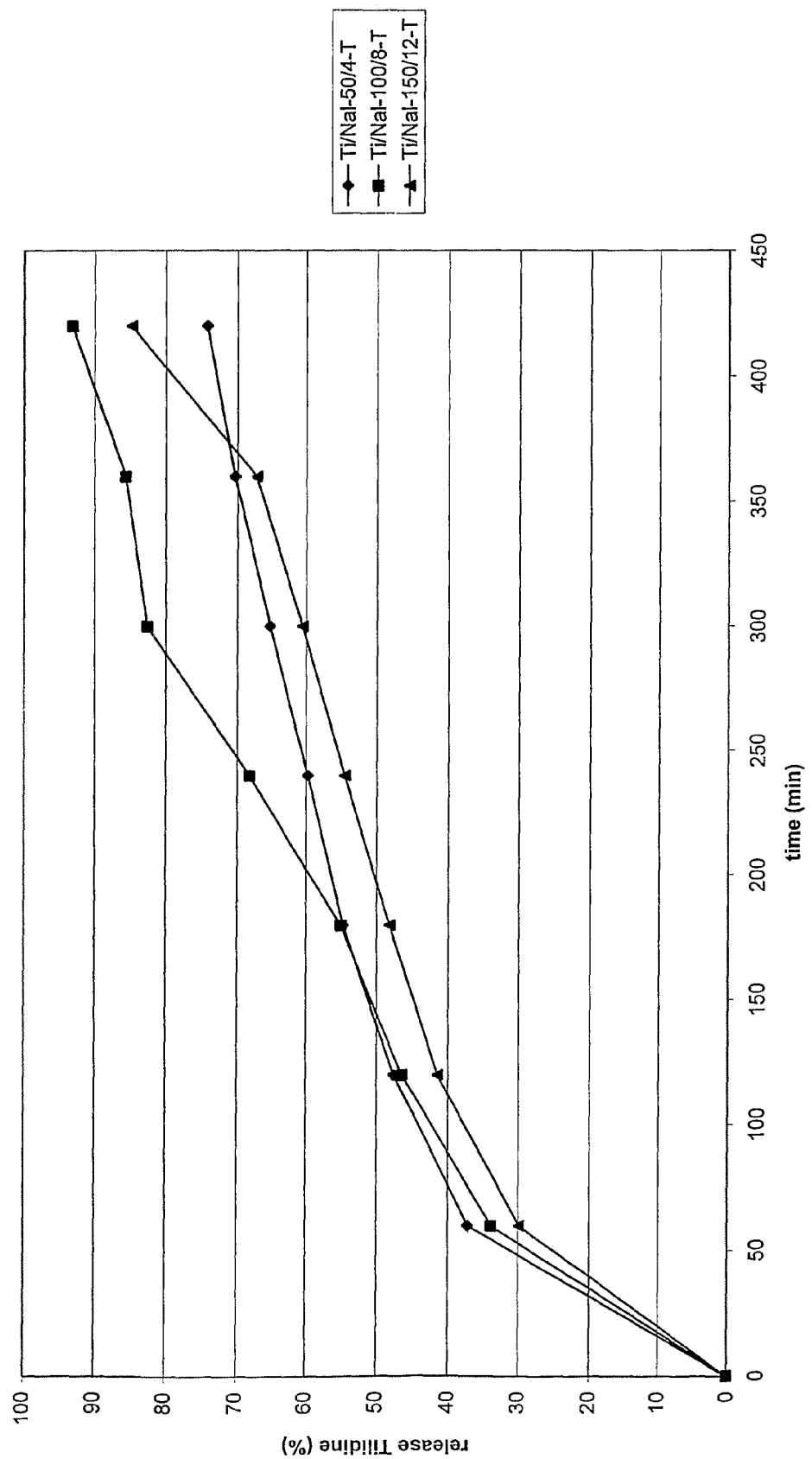
Figure 4B:
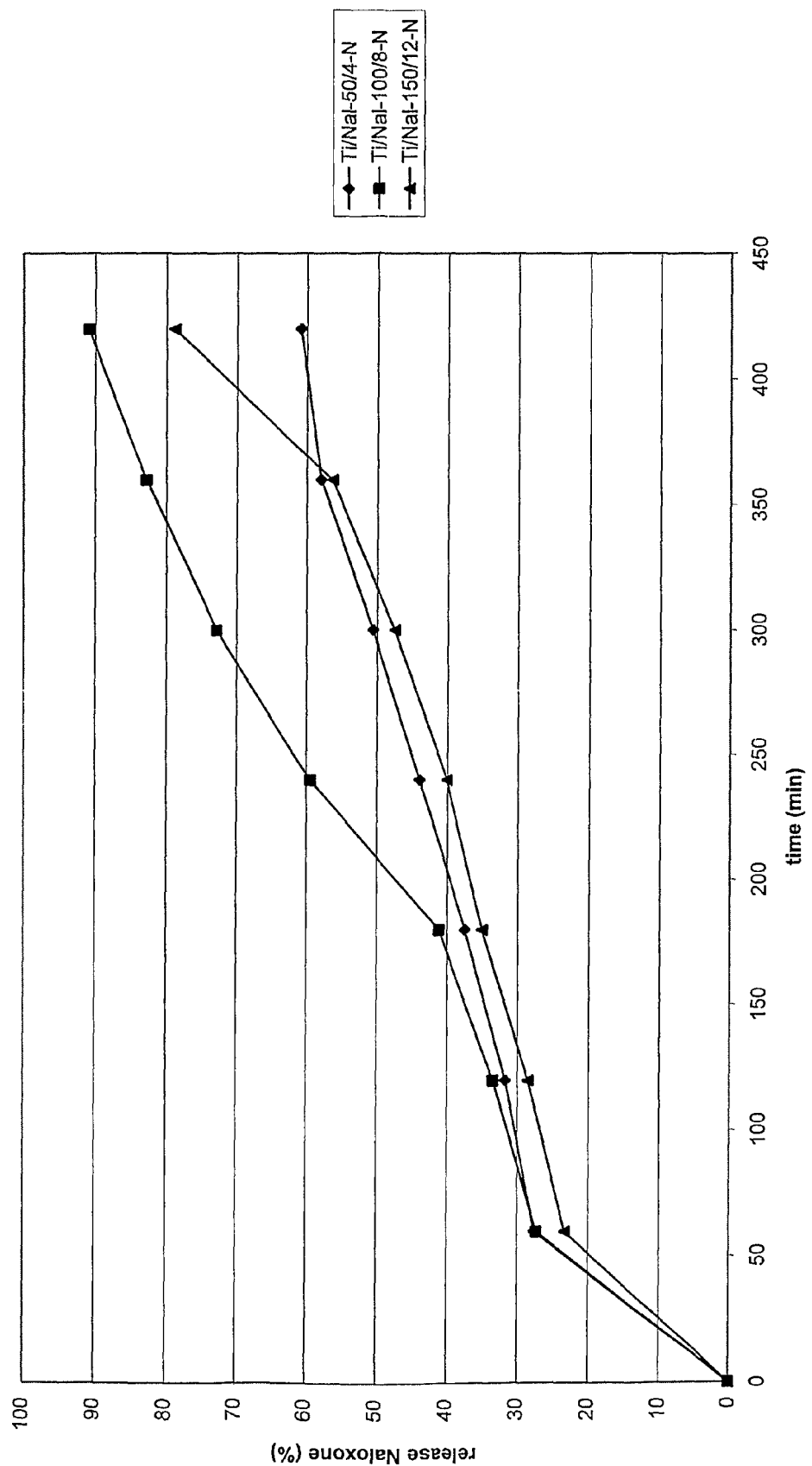

FIGS. 4A-4B: FIG. 4A provides the release profile of tilidine from Valoron® tablets with 50 mg tilidine and 4 mg naloxone (Ti/Nal-50/4), 100 mg tilidine and 8 mg naloxone (Ti/Nal-100/8), and 150 mg tilidine and 12 mg naloxone (Ti/Nal-150/12). FIG. 4B provides the release profile of naloxone from Valoron® tablets with 50 mg tilidine and 4 mg naloxone (Ti/Nal-50/4), 100 mg tilidine and 8 mg naloxone (Ti/Nal-100/8), and 150 mg tilidine and 12 mg naloxone (Ti/Nal-150/12).

FIGS. 5A-5B: FIG. 5A provides the surface of an Ox/Nal-10 tablet at 25× magnification. The voltage was 10 kV. The bar length corresponds to 2 mm. FIG. 5B provides the surface of an Ox/Nal-10 tablet at 200× magnification. The voltage was 10 kV. The bar length corresponds to 200 μm.

FIGS. 6A-6B: FIG. 6A provides the surface of an Oxy/Nal-Extr tablet at 40× magnification. The voltage was 10 kV. The bar length corresponds to 700 μm. FIG. 6B provides the surface of an Oxy/Nal-Extr tablet at 200× magnification. The voltage was 10 kV. The bar length corresponds to 300 μm.

FIGS. 7A-7B: FIG. 7A provides the surface of a Valoron® N tablet at 25× magnification. The voltage was 10 kV. The bar length corresponds to 2 mm. FIG. 7B provides the surface of a Valoron® N tablet at 100× magnification with crystal (Tilidine, down left). The voltage was 10 kV. The bar length corresponds to 500 μm.

Figure 8A:
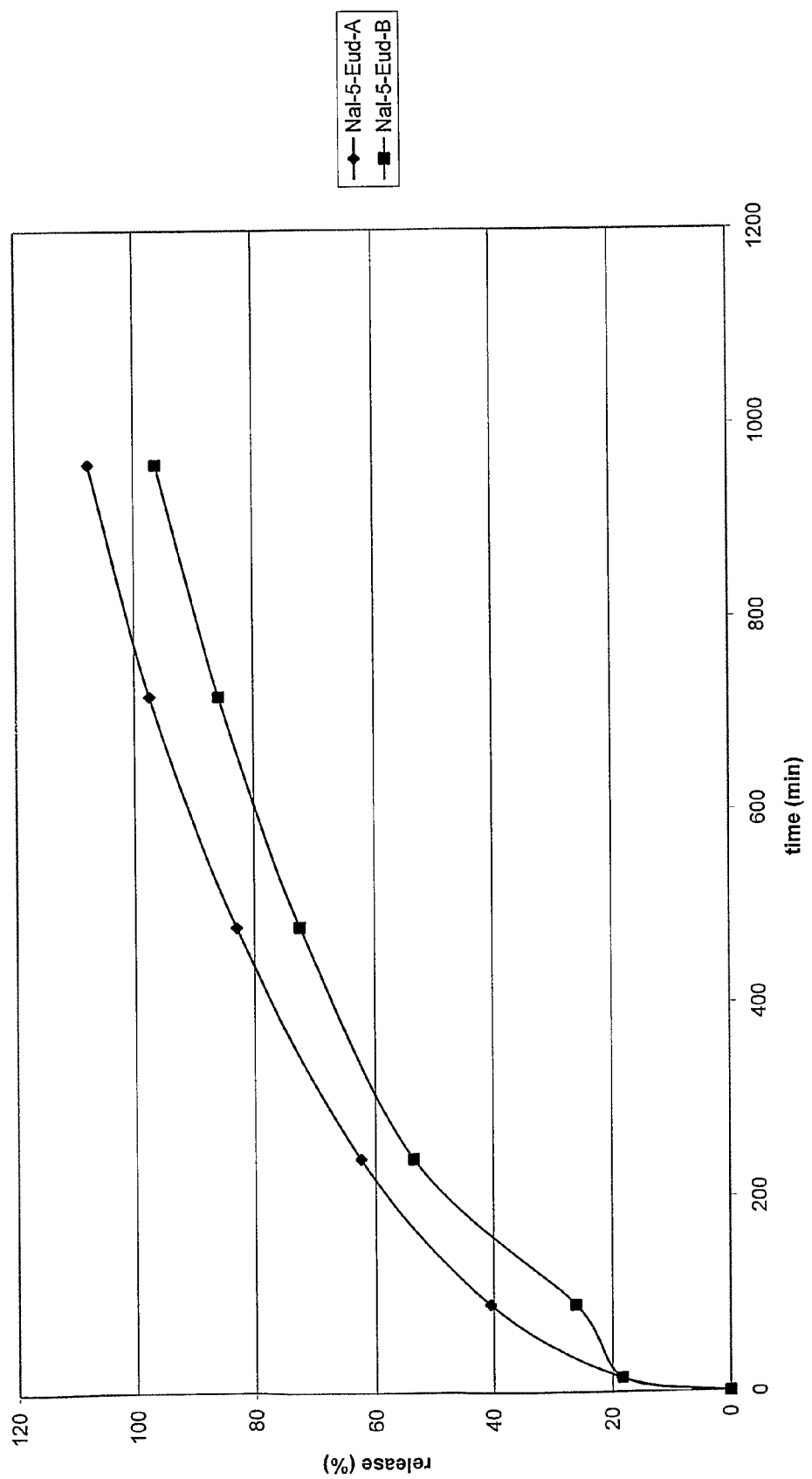
Figure 8B:
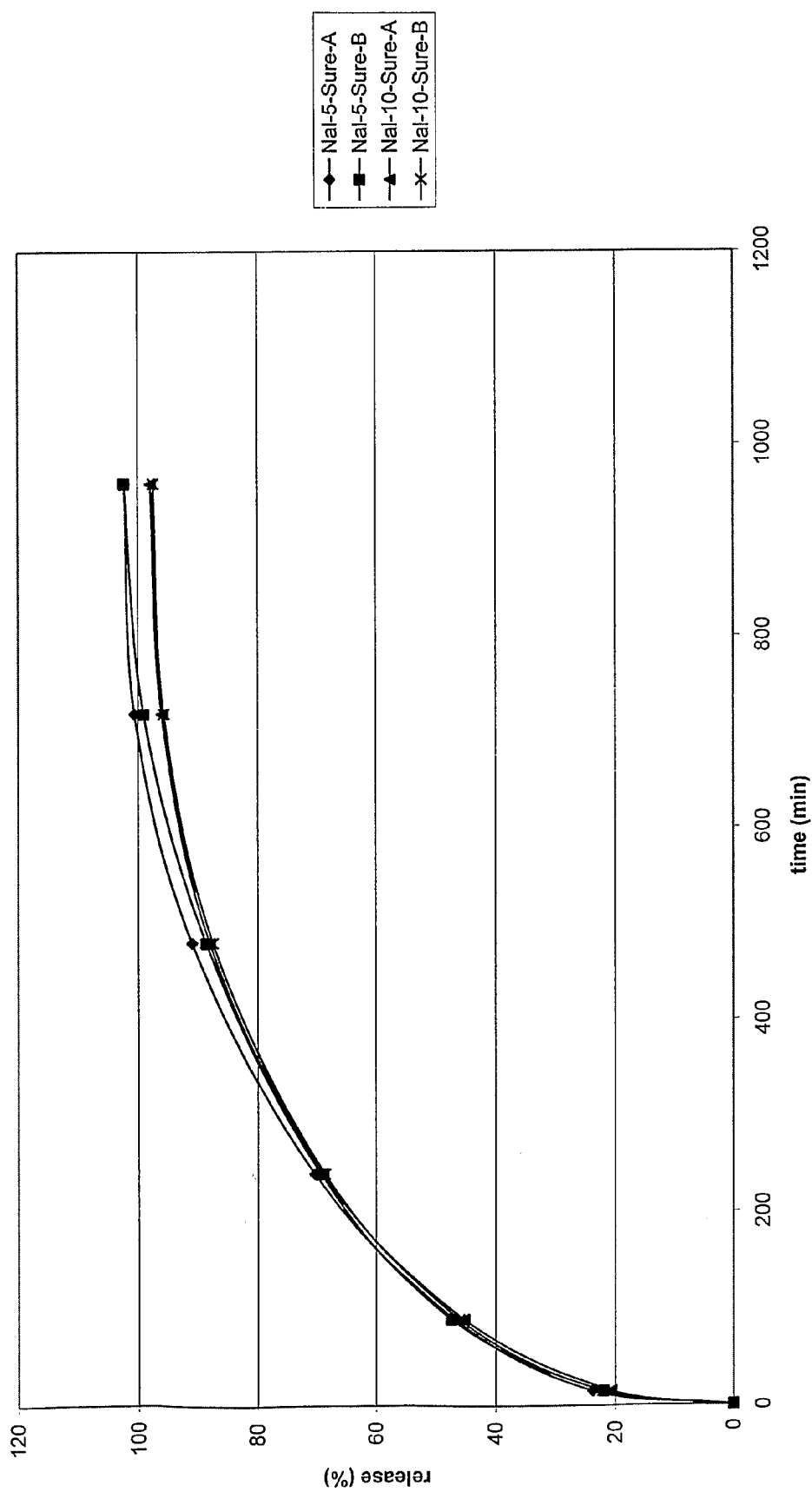

FIGS. 8A-8B: FIG. 8A provides the release profile of the naloxone-Eudragit® tablets from Example 7. FIG. 8B provides the release profile of the naloxone-Surelease® tablets of Example 7.

Figure 9:
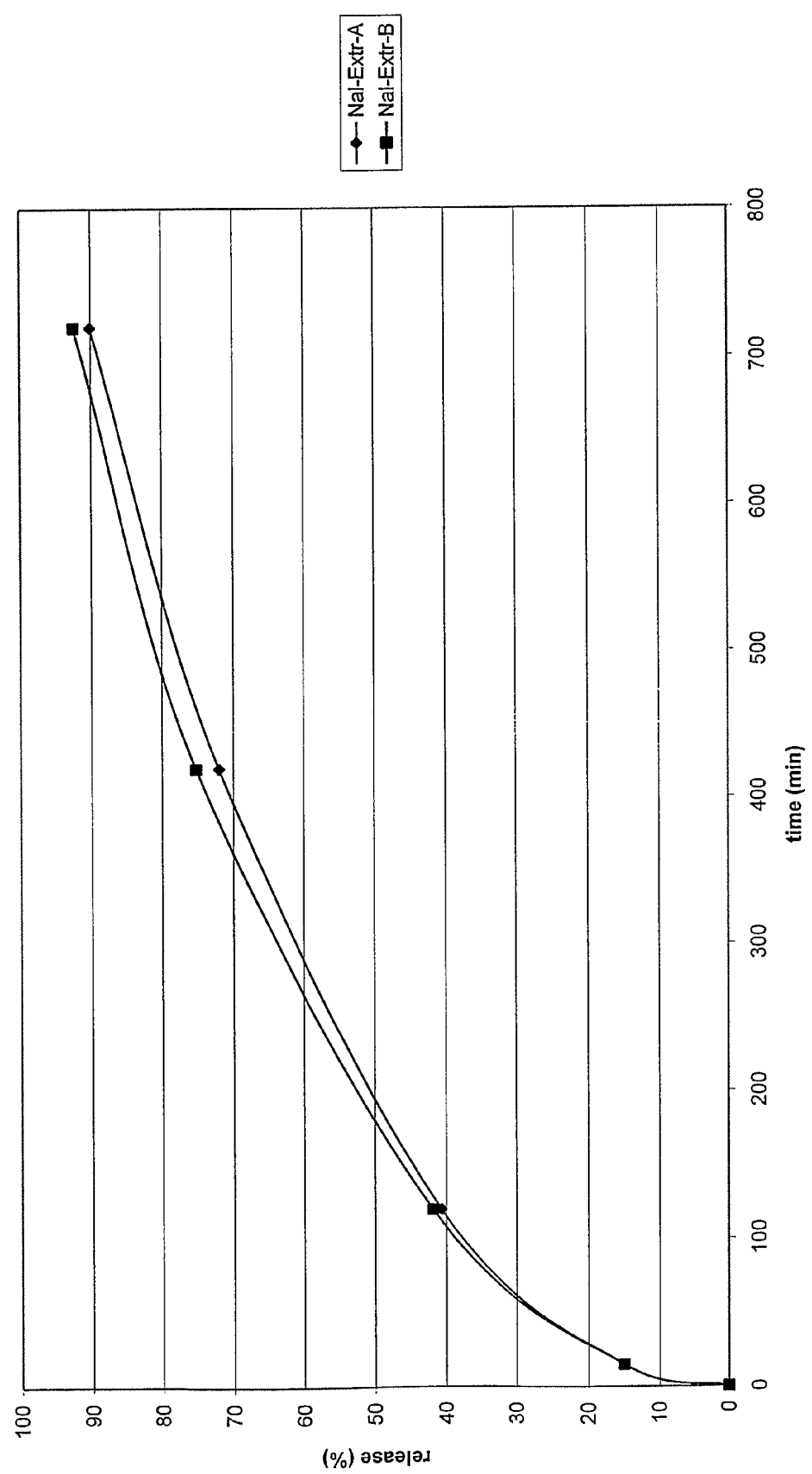

FIG. 9: provides the release profile of the naloxone tablets from Example 8.

FIGS. 10A-10B: FIG. 10A provides the surface of a Nal-5-Eud tablet at 25× magnification. The voltage was 10 kV. The bar length corresponds to 2 mm. FIG. 10B provides the surface of a Nal-5-Eud tablet at 200× magnification. The voltage was 10 kV. The bar length corresponds to 200 μm.

FIGS. 11A-11B: FIG. 11A provides the surface of a Nal-Extr tablet at 25× magnification. The voltage was 10 kV. The bar length corresponds to 2 mm. FIG. 11B provides the surface of a Nal-Extr tablet at 200× magnification. The voltage was 10 kV. The bar length corresponds to 200 μm.

FIGS. 12A-12B: FIG. 12A provides the surface of Nal-10-Sure granules at 30× magnification. The voltage was 10 kV. The bar length corresponds to 1 mm. FIG. 12B provides the surface of a Nal-10-Sure granules at 200× magnification. The voltage was 10 kV. The bar length corresponds to 100 μm.

FIGS. 13A-13B: FIG. 13A provides the surface of Nal-Extr granules at 30× magnification. The voltage was 10 kV. The bar length corresponds to 1 mm. FIG. 13B provides the surface of a Nal-Extr granules at 200× magnification. The voltage was 10 kV. The bar length corresponds to 100 μm.

Figure 14A:
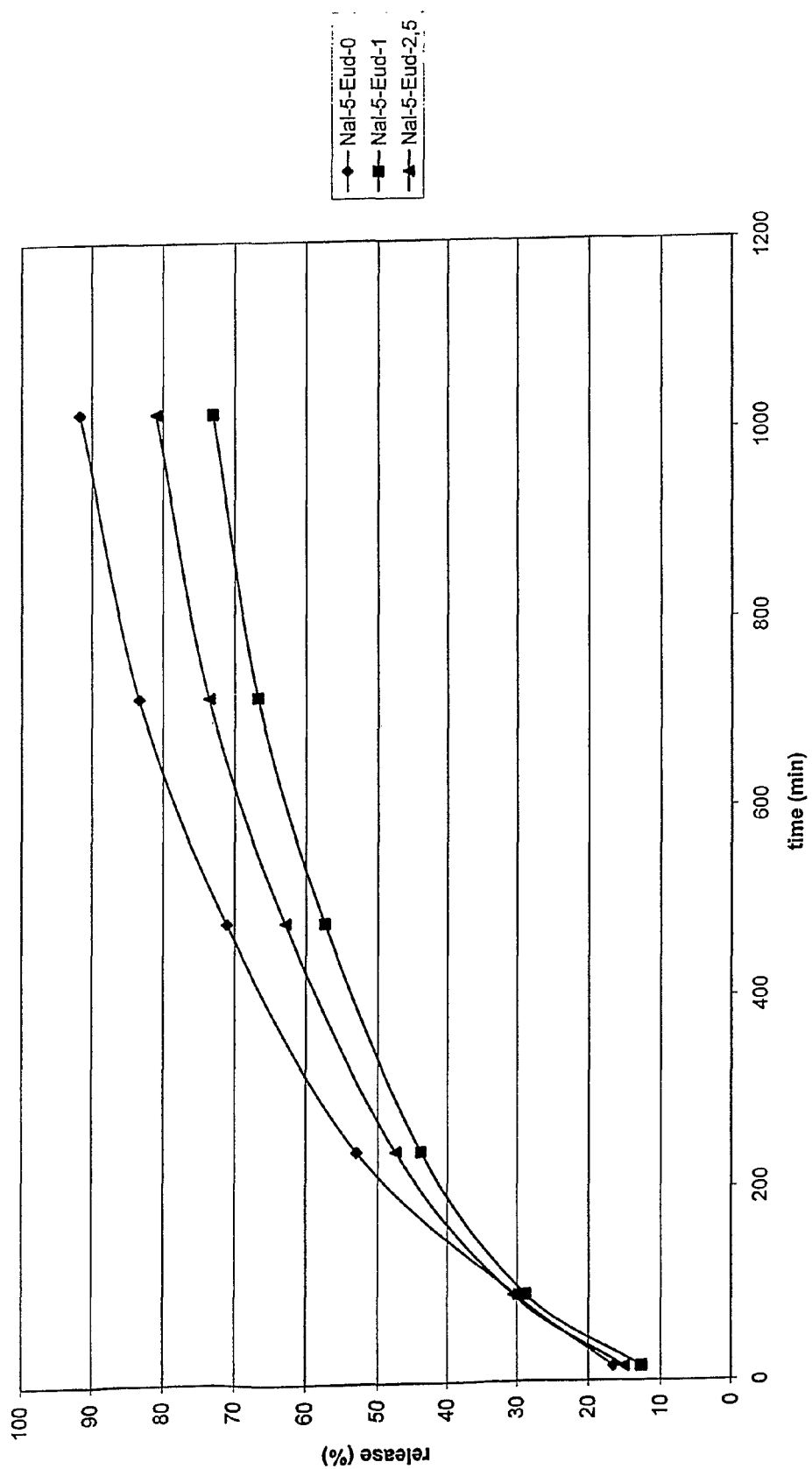
Figure 14B:
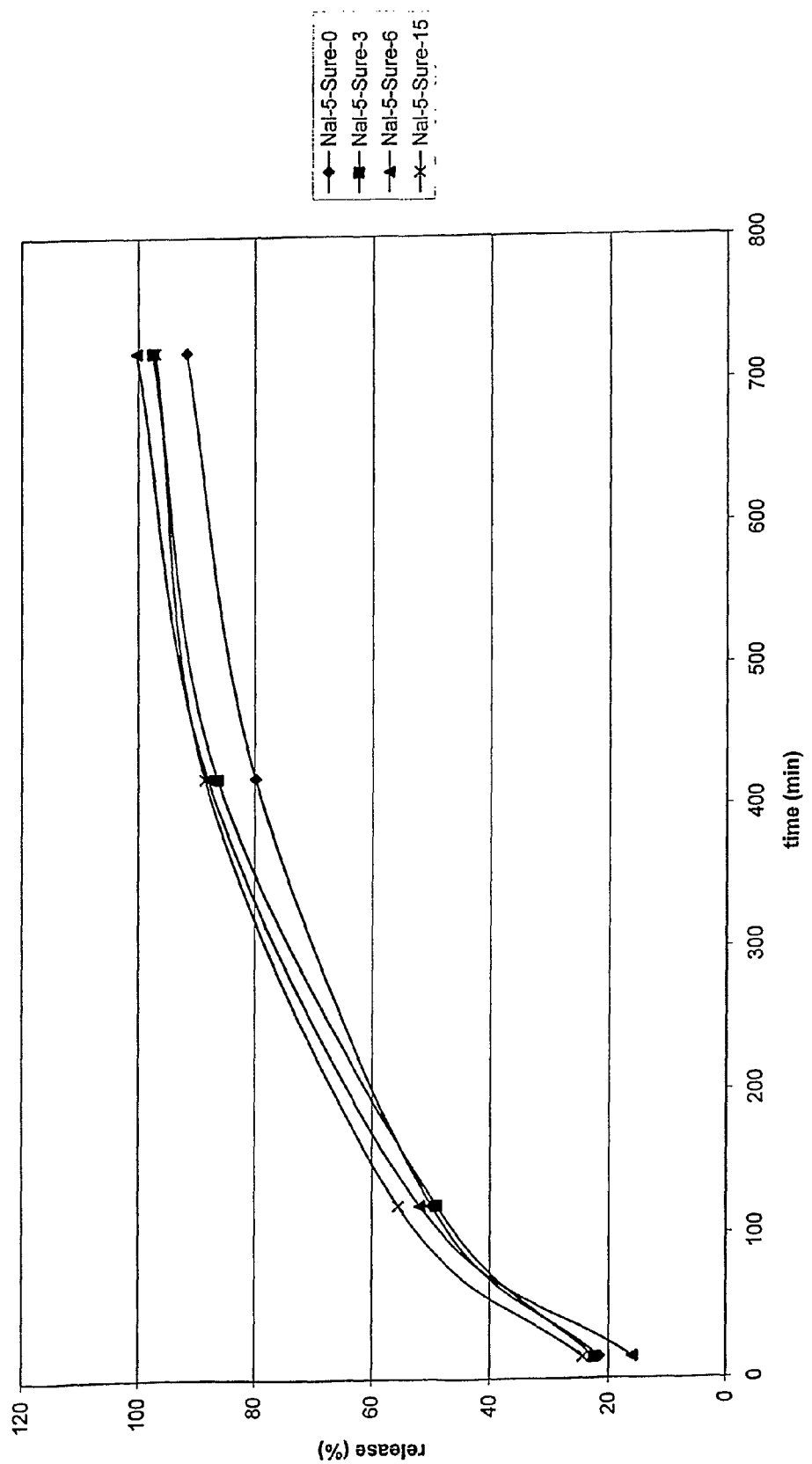

FIGS. 14A-14B: FIG. 14A provides the release profile of stored naloxone-Eudragit® tablets. FIG. 14B provides the release profile of stored naloxone-Surelease® tablets.

3. DETAILED DESCRIPTION OF THE INVENTION

The invention concerns a storage stable pharmaceutical formulation comprising at least one pharmaceutically active compound in a substantially non-swellable diffusion matrix, wherein the compound is released from the matrix in a sustained and invariant, and where several compounds are present, an independent manner. With respect to its essential release characteristics the matrix is formed by amounts of ethylcellulose and at least one fatty alcohol.

The invention also concerns a method for producing storage stable pharmaceutical formulations comprising at least one pharmaceutically active compound in a non-swellable diffusion matrix, wherein the at least one compound is released from the matrix in a sustained and invariant manner and, where several compounds are present, also an independent manner.

Sustained release formulations of pharmaceutical preparations take a central role in the development of improved therapies. It is the intent of all sustained release preparations to provide a longer period of pharmacological response after the administration of the drug than is ordinarily experienced after the administration of rapid release dosage forms. Sustained release pharmaceutical preparations comprising relatively large amounts of the pharmaceutically active compound and that release the compounds in a controlled, regulated manner over a longer period of time (typically 2-16 hours), ensure that the frequency with which the medicine has to be taken by the patient is reduced and that higher compliance by the patients is achieved.

The longer release duration and the concomitant prolonged effect of the active compounds, as is ensured by sustained release pharmaceutical preparations, provides moreover for many therapeutic benefits that are not achieved with corresponding short-acting, immediate release preparations. By using sustained release pharmaceutical preparations, therapy may be continued e.g. overnight without the necessity to interrupt the patient's sleep. This plays a role, for instance, in the treatment of epilepsy patients, where the occurrence of nocturnal attacks may thus be prevented. In the same way, patients suffering from chronic pain are allowed undisturbed sleep.

From the medical-pharmacological point of view, one advantage of sustained release formulations is the very uniform active compound concentration in the blood, leading to a long-lasting effect and reduced side effects. The reduction of side effects plays a decisive role during, e.g. the use of opioids for pain therapy. Opioid-induced side-effects comprise among others the danger of an addiction developing. As the addictive potential of an active compound is not defined by the compound itself, but rather by the way it is administered and the pharmaco-dynamic resulting therefrom (e.g. by the rate at which the brain encounters an active compound), the sustained release of an opioid analgesic can reduce the addictive potential of these active compounds (Nolte, T.: STK-Zeitschrift für angewandte Schmerztherapie, 2001, Vol. 2).

Since sustained release formulations allow for a uniformly high active compound concentration in the blood, the bio-availability of the active compound is increased. A multitude of factors contribute to the bio-availability of an active compound. Such factors include the active compound concentration in the respective physiological fluid (e.g. in the blood), the absorbability of the active compound across membranes (e.g. for the re-absorption in the gastro-intestinal system) and the availability of the active compound at the desired tissue site.

In order to be absorbed, for instance by the intestinal system, an active compound must be in solution. The time required for a given proportion of an active compound present in a unit dosage of a pharmaceutical preparation in order to be dissolved in the respective physiological fluid, is designated as the dissolution time, also as the release time, or release rate. The dissolution time of an active compound is determined as the proportion of the active compound released from a unit dosage form over a specified time based on a test method conducted under standardized conditions. The physiological fluid in which the dissolution time of the active compound is determined may be, e.g. the fluid of the gastro-intestinal system. The state of the art recognises may satisfactory test procedures for measuring dissolution time for pharmaceutical compositions (and correspondingly, for the release rates of the active compounds), and these test procedures are described in official compendia worldwide.

Among the various factors affecting dissolution time of pharmaceutical compositions, and thereby the release rates of active compounds, are the surface area of the pharmaceutical composition accessible to the dissolution solvent medium, the pH of the dissolution solvent medium, the solubility of the active compound in the dissolution solvent medium and the saturation concentration of dissolved materials in the dissolution solvent medium.

Despite the diverse factors that influence the dissolution of the active compound in the dissolution medium as well as the absorption of the active compound, a strong correlation has been established between the in vitro dissolution time determined for a pharmaceutical preparation and the in vivo bio-availability of the active compound. This correlation is so well established that the dissolution time (release rate of the active compound) is considered to be a generally accepted criterion for the bio-availability of the active compound of a pharmaceutical preparation. In view of this correlation, it becomes clear that the release rate as determined for the active compound of a pharmaceutical formulation is one of the important fundamental characteristics that has to be considered when evaluating sustained release formulations.

Different approaches are known from the prior art that allow the formulation of sustained release pharmaceutical preparations. These approaches have in common that the active compound is combined with additives to shape bodies, such as tablets or dragées, with the additives forming a release or dissolution barrier for the active compound. Depending on the nature of the release barriers, different sustained release methods can be distinguished. There are, e.g. osmotic systems, systems by which retardation is achieved through coatings, or systems in which the active compounds are embedded in waxes, polymethacrylates, gel-formers or silicic acids. There are moreover the so-called matrix forms, which are of fundamental importance when formulating sustained release pharmaceutical preparations. Matrix means a shaped body comprising the active compound bound to additives which are as inert as possible. Depending on the type of matrix, one can differentiate between e.g. swellable or non-swellable matrices. Moreover matrices differ depending on whether the active compound is released by pure diffusion or by erosion of the matrix (U. Schöffling, Arzneiformenlehre, 1998, $3^{rd}$ edition, Deutscher Apotheker-Verlag, Stuttgart).

The additives used for the preparation of sustained release pharmaceutical preparations frequently lead to problems concerning the stability of the pharmaceutical preparation after prolonged storage times. For e.g. waxes, it has been shown that they are subject to changes, so that extensive precautionary steps have to be taken even at the time of production, in order to prevent changes during the storage time. If film coatings consisting of polymers produced from aqueous dispersions are used for retardation, these pharmaceutical preparations also frequently display problems with storage stability.

There are prior art sustained release pharmaceutical preparations having so-called controlled release of the pharmaceutically active compound, i.e. the release of the active compound is not only prolonged, but moreover can be adjusted to a predetermined release rate. Depending on which polymers (hydroxyalkylcelluloses, polymethacrylates or e.g. alkylcelluloses) are used for the production of e.g. matrix-based sustained release pharmaceutical preparations with controlled release, the release behaviour of the respective pharmaceutically active compounds may differ, the release behaviour of the active compound frequently being difficult to predict.

Generally, it should be ensured that pharmaceutical preparations of a given pharmaceutical formulation release the respective compound always with reproducible equal release rates or release profiles, even if the formulation comprises different absolute amounts of the active compounds. However, due to the stability problems, which are caused by the components responsible for the sustained release, this is not guaranteed.

There is a large number of sustained release pharmaceutical preparations for different therapeutic applications that frequently contain only one active compound. The medicament Oxygesic®, which is used in pain therapy, contains e.g. oxycodone as the only analgetically active compound. The medicament Kapanol®, which is also used in pain therapy, comprises morphine sulfate as analgetically active compound.

As the long term application opioid analgesics such as oxycodone may go along with the development of side effects such as breath depression and obstipation, co-treatment of patients with opioid antagonists that specifically counteract the opioid-induced side effects may be necessary. If patients seeking pain release are treated with preparations comprising an opioid analgesic, simultaneous treatment with preparations comprising antagonists such as naltrexone or naloxone may be desirable in order to counteract the aforementioned side effects. If the opioid-containing preparation is a sustained release preparation, the antagonist-preparation should also provide for a sustained release as otherwise development of side effects may not effectively be repressed. However, sustained release formulations of e.g. naloxone alone are not available on the market.

In the treatment of different symptoms it is therefore a common strategy to counteract the side-effects provoked by an active compound by simultaneous administration of another compound that selectively reduces these side-effects. If e.g. opioid analgesics are used in pain therapy, side-effects such as obstipation and breath depression may occur in addition to the danger of the development of dependency and addiction as already mentioned. Various attempts have therefore been made to eliminate, or at least significantly reduce, the addictive and habit-forming potential of opioid analgesics as well as their other side-effects, by the simultaneous administration of antagonists which counteract the opioid analgesic.

In view of the significant advantages that such combination preparations have and due to the aforementioned general advantages of sustained release pharmaceutical preparations, there is a great need for sustained release formulations of such combination preparations. Sustained release formulations of combination preparations should combine in an ideal manner the positive, synergistic effects of the different active compounds with the long-lasting release and the correspondingly increased period of effectiveness.

One example of such a combination preparation which releases several compounds in a sustained manner is Valoron® from Gödecke, which comprises tilidine as an analgetically active compound and naloxone as antagonist.

However, one problem that frequently occurs with combination preparations is that active compounds of different chemical structures and physical characteristics have to be combined in one matrix. Such a combination usually leads to different release profiles for both compounds. The release of both compounds with the same release profiles can, however, be highly desirable from a medical point of view. Moreover, it may be preferable that both compounds are released from the same matrix, since in this way e.g. tablets may be produced which can be split. Such tablets are suitable for individual dosing and the production process of the corresponding preparations can be significantly simplified. Another aspect is that with several compounds of different structures being present, the compounds may differ with respect to their stability in the matrix over a longer storage period. Additionally, the change of amount of one compound may change the release profile of other compounds in an unpredictable manner in such combination preparations, resulting in significant expenditure in the production of preparations having different amounts of the active compounds, since one cannot infer from the release behaviour of one preparation the release behaviour of another one.

Generally, medicaments have to be formulated in a such a way that the active compounds are stable as long as possible under standard storage conditions. Medicaments also have to be formulation in such a way that the intended release profiles of the active compounds do not change during long-term storage.

It should also be ensured that the release profile of one active compound of a given sustained release formulation does not change depending on the amount of the active compound. This applies to the case where a single compound or also several compounds are present in the pharmaceutical preparation.

Additionally (also in the case of active compound combinations), the release profile of each single compound should be selectable as required. The measures to be taken in order to achieve this should not prevent, or even hamper the release profiles of additional active compounds, e.g. in the case of combinations of different active compounds, being chosen as required. Consequently, there should be no mutual dependency of the release profiles.

For a variety of therapeutic applications there is a great need for combination preparations. Particularly for pain therapy combination preparations are required that consist of opioid analgesics and corresponding antagonists, where the respective pharmaceutical preparations release both compounds in a sustained manner and also possess the aforementioned characteristics. Matrix formulations that ensure a sustained release of active compounds in general and of opioid analgesics and their antagonists in particular and that possess the aforementioned characteristics are not known from prior art.

German patent application DE 43 25 465 A1 concerns the treatment of side-effects during pain therapy by a preparation consisting of an opioid agonist and an antagonist. The characterizing feature of this disclosure is that the antagonist must not be released in a sustained manner while the agonist should be released in a sustained manner.

International patent application WO 99/32120 is also concerned with a preparation consisting of an opioid analgesic and an antagonist. According to this disclosure, both compounds should be released in a sustained manner. Storage stability and the mutual dependency of the release profiles of compounds is, however, not subject matter of this application.

The aforementioned pain-relief medicament Valoron® is a tilidine/naloxone-combination. According to the manufacturer's data it is a formulation from which both active compounds are released in a sustained manner. The matrix used comprises a relevant part of water-swellable material (hydroxypropylmethylcellulose (HPMC)) and has therefore to be considered as a swellable (and possibly partially erosive) diffusion matrix. The disadvantage of this known formulation is that tilidine and naloxone, given identical mass ratios but different absolute amounts, display different release profiles, if the release is measured for certain pH values. The release rates of the agonist and the antagonist are not independent of each other, which is probably due to the sustained release formulation used. Accordingly, it is necessary for the physician to carry out extensive titration experiments for each individual patient if he wants to increase the dosage, even though he does not change the mass ratio of tilidine:naloxone, since he cannot assume that the release profiles of both components will remain constant. The range of therapeutically usable amounts of the analgesic available to the physician is therefore limited.

One objective of the present invention is to provide formulations for a pharmaceutical preparation that ensure that the active compounds of the preparations are released in a sustained manner, that are stable over a long storage period, and where the release of one compound does not change even when different amounts of the active compound are used. A further objective of the invention is to provide formulations for pharmaceutical preparations that display the above-mentioned characteristics and that show no mutual dependency of the release profiles of the active compounds.

Another objective of the present invention is to provide methods for producing pharmaceutical formulations comprising at least one pharmaceutically active compound and from which the compounds are released in a sustained, reproducibly invariant and, where several compounds are present, independent manner. Such formulations should remain stable even after longer storage periods.

A particular objective of the present invention is to provide formulations for pharmaceutical preparations that comprise the opioid antagonist naloxone, wherein the active compound is stable over a long storage time and is released from the preparation in a sustained and reproducibly invariant manner. Formulations that achieve this, are not known from prior art.

An additional objective of the present invention is to provide formulations for pharmaceutical preparations for pain therapy comprising at least one opioid analgesic and at least one antagonist counteracting the opioid analgesic, wherein the formulation is stable over a long storage period and wherein the active compounds are released from the preparation independently of each other in a sustained and reproducibly invariant manner.

The features of the independent claims serve to attain these and further objectives which can be noted from the following description of the invention. Preferred embodiments of the invention are defined in the dependent claims.

According to the invention the objectives are solved by providing a pharmaceutical formulation comprising at least one pharmaceutically active compound in a substantially non-swellable diffusion matrix, wherein the matrix is formed with respect to its essential release characteristics by ethylcellulose and at least one fatty alcohol.

It has surprisingly been found that only formulations having a (substantially) non-swellable diffusion matrix based on ethylcellulose and at least one fatty alcohol ensure a sustained, invariant and, if several active compounds are present, independent release of the active compounds.

The inventive matrix formulation which is stable over long storage periods permanently ensures that the active compounds are always released in predetermined percentages and that the release rates do not influence each other. For combination preparations that e.g. comprise opioid analgesics and the respective antagonists, abuse of the medicaments, which presupposes that the agonist can be selectively extracted from the formulation, is prevented.

The formulation according to the invention disables selective extraction of the agonist from the preparation without the corresponding amount of the antagonist, regardless of the absolute and relative amount of agonist and antagonist chosen. Furthermore, such preparations reduce side-effects which usually occur during the application of opioids. Since the active compounds are released from the same matrix, a simplified and more efficient production process is made possible. This also applies for combination preparations comprising other compounds other than opioids analgesics or antagonists thereof.

Moreover, the inventive formulation of a medicament ensures that given identical relative amounts, the active compounds show the same release profiles regardless of the absolute amount present. Such independent release behaviour provides the physician with a wide range of usable absolute amounts of the active compounds, where the optimal compound ratio (e.g. for opioid agonist/antagonist ratios) is known. It is thus possible to comfortably adjust the dosage for each individual patient, either by increasing the dosage gradually or, if necessary, by reducing the dosage gradually. This ability to adjust the dosage for the individual patient is extremely useful from a medical point of view, as is the increased compliance.

The inventive formulations also allow for the production of pharmaceutical preparations that release active compounds of different structures with the same release profiles.

Since the pre-determinable release of active compounds from the inventive formulation does not change regardless of the amount and the number of compounds and takes place from the same matrix, once a combination of active compounds has been established preparations with different amounts of active compound can be produced without significant technical effort and corresponding preparations for different therapeutically relevant areas may be provided.

The characterizing features of the present invention are the sustained, invariant, and if several active compounds are present, independent release of the active compounds from a non-swellable (at least not to an extent which is relevant for the release) diffusion matrix with the matrix being determined with respect to its essential release characteristics by ethylcellulose and at least one fatty alcohol and the active compounds remaining stable over long storage periods.

According to the present invention "sustained" or "controlled sustained release" or "retardation" means that pharmaceutically active substances are released from a medicament over a longer period of time than is the case with known formulations for immediate release. Preferably, the release takes place over a time period of two to twenty-four hours, of two to twenty hours, especially preferably over a time period of two to sixteen hours or two to twelve hours, with the specifications satisfying legal requirements.

In the context of the present invention, "sustained release" does not mean that the active compounds are released from the formulation or the medicament in a pH-dependent manner. According to the invention, the term "sustained release" refers to the release of active compounds from a medicament over an extended period of time. It does not imply the controlled release at a defined place; it therefore does not mean that the active compounds are either released only in the stomach, or only in the intestine. Correspondingly, the release of the active compounds from the inventive formulations occurs preferably pH-independently.

(Of course, a pH dependent release at a defined place could individually be achieved by, e.g. enteric coating of the medicament, although this presently seems not to be advantageous).

According to the invention, "independent release" means that, given the presence of at least two active compounds, a change of the absolute amount of one compound does not influence the release profiles of the other compounds so that the release profiles of the other compounds are not changed. For formulations according to the invention such an independent release behaviour is independent of the pH value, for which the release is measured, or of the production process. The pH independency particularly applies to the acidic range, i.e. for pH values <7. The release profile (or release behaviour) is defined as the change of the release of the active compound from the formulation with time, with the amount of each active compound released provided in percents of the total amount of the active compound. The release profile is determined by known tests.

Specifically, this means that for example the release profile of oxycodone, as it is observed for an oxycodone/naloxone-combination with 12 milligrams oxycodone and 4 milligrams naloxone, does not change, if a corresponding preparation with the same formulation contains 12 milligrams oxycodone, but 6 milligrams naloxone.

The independent release feature preferably refers to the situation where preparations of substantially equal composition are compared for the release profile. Preparations of substantially equal composition have different amounts of the active compounds but are otherwise basically the same with respect the components of the composition which essentially influence the release behaviour.

If e.g. the above-mentioned preparations are compared (with the first preparation comprising 12 mg oxycodone and 4 mg naloxone and the second preparation comprising 12 mg oxycodone and 6 mg naloxone) both preparations, provided that they have the same total weight, will provide for the same release profile for oxycodone and naloxone if the difference in the naloxone amount is replaced by a component in the formulation that typically does not influence the release behaviour. As shown in the Example section, the difference in the amount of naloxone may be replaced by a typical pharmaceutically inert filler such as lactose without changing the release profiles.

The person skilled in the art is well aware that if the amount of the active compound in which two preparations differ is replaced by a substance that is essential for the release behaviour of the formulation, such as ethylcellulose or a fatty alcohol, differences in the release behaviour may occur. Thus, the independent release feature preferably applies to formulations that have different amounts of the active compounds but are otherwise identical or at least highly similar with respect to the components that essentially influence the release behaviour (given that formulations of the same total weight are compared).

According to the invention, "invariant release behaviour" or "invariant release profile" is defined so that the percentage of the absolute amount of each active compound released per time unit does not significantly change and remains sufficiently constant (and thus does not substantially change) if absolute amounts are changed. Sufficiently constant percentages mean that the percentage released per time unit deviates from a mean value by not more than 20%, preferably by not more than 15% and especially preferably by not more than 10%. The mean value is calculated from six measurements of the release profile. Of course, the amount released per time unit has to satisfy the legal and regulatory requirements.

Specifically, this means for example that given an oxycodone/naloxone combination of 12 mg oxycodone and 4 mg naloxone, during the first 4 hours 25% oxycodone and 20% naloxone are released. If the oxycodone/naloxone combination instead contains 24 mg oxycodone and 8 mg naloxone, during the first 4 hours also 25% oxycodone and 20% naloxone will be released. In both cases the deviation will not be more than 20% from the mean value (which in this case is 25% oxycodone and 20% naloxone).

As outlined for the independent release behaviour, the invariant release feature also preferably refers to a situation where preparations of substantially equal composition are compared. Such preparation differ with respect to the amount of the active compounds, but are of the same or at least highly similar composition with respect to the release-influencing components of the preparation. Typically, the difference in the amount of an active compound will be replaced by the amount of a pharmaceutical inert excipient which does not substantially influence the release behaviour of the preparation. Such a pharmaceutical excipient may be lactose, which is a typical filler in pharmaceutical preparations. The person skilled in the art is well aware that the invariant release feature may not apply to preparations where the difference in the amount of an active compound is replaced by substances that are known to essentially influence the release behaviour of the preparation, such as ethylcellulose or fatty alcohols.

In the Example section it is set out that if one preparation comprises 20 mg oxycodone and 1 mg naloxone or 20 mg oxycodone and 10 mg naloxone, with the difference in naloxone being replaced by lactose, that the two preparations of identical weight provide for the same release profiles, so that they exhibit a sustained, invariant and independent release behaviour.

According to the invention "storage stable" or "storage stability" means that upon storage under standard conditions (at least two years at room temperature and usual humidity) the amounts of the active compounds of a medicament formulation do not deviate from the initial amounts by more than the values given in the specification or the guidelines of the common Pharmacopoeias. According to the invention, storage stability also means that a preparation produced according to the invention can be stored under standard conditions (60% relative humidity, 25° C.) as it is required for admission to the market.

According to the invention, "storage stable" or "time stable" also means that after storage under standard conditions the active compounds show release profiles as they would upon immediate use without storage. According to the invention, the admissible fluctuations with respect to the release profile are characterized in that the amount released per time unit fluctuates by no more than 20%, preferably no more than 15% and especially preferably no more than 10%, with respect to a mean value. The mean value is calculated from six measurements of the release profile.

The term "storage stable" refers to the active compound as well as to the other components within the inventive formulation and therefore also to the formulation as a whole.

Preferably, the release of the active compounds from a sustained release formulation is determined by the Basket Method according to USP at pH 1.2 or pH 6.5 with HPLC.

Storage stability is preferably determined by the Basket Method according to USP at pH 1.2 with HPLC.

According to the invention, the term "formulation" refers to the preparation of a pharmaceutically active substance with additives (formulation aids) with the aim of enabling an optimal release, distribution and development of activity of the active compound for the respective applications.

According to the invention, a "non-swellable" or "substantially non-swellable" diffusion matrix is a matrix formulation for which the release of the active compounds is not influenced (or at least not to a relevant degree) by swelling of the matrix (particularly in the physiological fluids of the relevant target sites in the patient's body).

According to the invention, the term "substantially non-swellable" diffusion matrix also refers to a matrix whose volume will increase by approximately 300%, preferably by approximately 200%, more preferably by approximately 100%, by approximately 75% or by approximately 50%, even more preferably by approximately 30% or by approximately 20% and most preferably by approximately 15%, by approximately 10%, by approximately 5% or by approximately 1% in aqueous solutions (and particularly in the physiological fluids of the relevant target sites in the patient's body).

It has now surprisingly been found that formulations for medicaments with a substantially non-swellable diffusion matrix allow for a sustained, invariant and, where several compounds are present, independent release of the active compounds, when the diffusion matrix comprises ethylcellulose as the matrix-scaffold-forming substance and is moreover determined with respect to its essential release characteristics by ethylcellulose and/or at least one fatty alcohol. Additionally, such formulations are characterized by good storage stability. Given the present knowledge, mainly formulations with such a diffusion matrix allow to release the active compounds in the aforementioned inventive manner. Formulations with a (substantially) swellable diffusion matrix or an erosive matrix are currently not considered to be suitable for that.

Therefore, water-swellable substances and particularly water-soluble polymers may generally not be used as scaffold-forming substances for the production of matrices for formulations in accordance with the invention. Particularly, common matrix-forming polymers such as polyvinylpyrrolidone, hydroxypropylcellulose, hydroxypropylmethylcellulose, hydroxyethylcellulose, hydroxymethylcellulose, poly(vinylalcohols), alginates, hydrated hydroxyalkyl-cellulose and hydroxypropylmethylcelluloseether are currently not considered to be suitable for the production of formulations in according with the invention.

Scaffold-forming substances that can form non-swellable diffusion matrices may be used for the production of formulations in accordance with the invention if they provide for a release behaviour of the active compound in accordance with the invention, i.e. for a sustained, invariant and, where several components are present, independent release, as well as for storage stability of the formulation. Water-insoluble polymers, that are commonly used for the production of matrix-based sustained release pharmaceutical preparations may also not be used straightforwardly for the production of formulations in accordance with the invention. Common scaffold-forming substances such as acrylic acid and methacrylic acid copolymers, methylmethacrylate copolymers, ethoxyethylmethacrylate copolymers, cyanoethylmetha-crylate, aminoalkylmethacrylate copolymers, poly(acrylic acid), poly(methacrylic acid), polymethacrylates, poly(methylmethacrylate) copolymers, polyacrylamine or alginic acid are currently not considered to be suitable for the production of formulations in accordance with the invention.

Matrices which are based on polymethacrylates (as e.g. Eudragit® RS30D and

Eudragit® RL30D) or comprise relevant amounts of water-swellable material, particularly of hydroxyalkylcellulose such as HPMC will currently not be considered usable in accordance with the invention.

Currently, alkylcelluloses will generally also not be considered for the production of formulations in accordance with the invention. Propylcellulose e.g. is of too lipophilic character to produce matrices with release characteristics in accordance with the invention. Methylcellulose is also not suitable for the formulations in accordance with the invention.

In accordance with the invention, the matrix that ensures the sustained release of the active compound will be selected in such a way that the release of the active compounds takes place in a sustained, invariant and, if several compounds are present, independent manner, and that the formulation is storage stable. Preferably such matrices comprise polymers based on ethylcellulose, with ethylcellulose being an especially preferred polymer. Specifically preferred are matrices comprising polymers available on the market under the trademark Surelease®. Particularly preferred is the use of Surelease® E-7-7050.

Other retardation methods, such as e.g. film coatings that ensure a sustained release, are currently not considered to be suitable for production of formulations that provide for a release behaviour of the active compounds which is in accordance with the invention. Furthermore, they are not considered to be suitable for production of formulations that ensure that the formulation is storage stable.

For formulations in accordance with the invention which comprise a non-swellable diffusion matrix on an ethylcellulose basis, the amount of ethylcellulose (or Surelease® E-7-7050) in the matrix will vary between 1-15%, preferably between 3-12%, particularly preferably between 5-9% and even more preferably between 6-8%. The percentages indicating the amount of ethylcellulose (or Surelease®) with respect to the total weight of the preparation.

Formulations in accordance with the preparation preferably comprise a fatty alcohol as the second component which has a sustained release effect besides ethylcellulose. Fatty alcohols may comprise lauryl, myristyl, stearyl, cetylstearyl, ceryl and/or cetylalcohol. Preferably, stearyl and/or cetylalcohol will be used. The amount of fatty alcohol in the matrix will be between 5-30%, preferably between 10-25% and particularly preferably between 15-20%. Particularly preferred is an amount of fatty alcohol of substantially 20% (if the matrix is produced by spray granulation) or of substantially 18% (if the matrix is produced by extrusion). All percentages indicating the amount of fatty alcohol refer to the total weight of the preparation.

Formulations with release behaviour according to the invention comprise in particular matrices comprising ethylcellulose and at least one fatty alcohol as the components that essentially influence the release characteristics of the matrix. The amount of ethylcellulose and the at least one fatty alcohol may vary significantly, so that preparations with different release profiles may be achieved. Even though the inventive preparations will usually comprise both of the aforementioned components, in some cases it may be preferred that the preparations comprise only ethylcellulose or the fatty alcohol(s) as the release determining components.

Formulations in accordance with the invention may comprise further components which have a sustained release effect if required. However, it has to be ensured that the release of the active compounds from the formulation and the storage stability of the formulation are in accordance with the invention and are not negatively influenced. Such additional components with sustained release effect may comprise polyalkylene glycols and particularly preferably polyethylene glycols.

According to the invention, formulations that provide a release of the active compounds in accordance with the invention may comprise, besides the matrix forming polymers, fillers and additional substances, such as granulating aids, lubricants, dyes, flowing agents and plasticizers.

Lactose, glucose or saccharose, starches and their hydrolysates, microcrystalline cellulose, cellactose, sugar alcohols such as sorbitol or mannitol, poorly soluble calcium salts like calciumhydrogenphosphate, dicalcium- or tricalciumphosphate may be used as fillers.

Povidone may be used as granulating aid.

Highly-disperse silica (Aerosil®), talcum, corn starch, magnesium oxide and magnesium- and/or calcium stearate may preferably be used as flowing agents or lubricants.

Magnesium stearate and/or calcium stearate can preferably be used as lubricants. Fatty acids like stearic acid, or fats like hydrated castor oil can also preferably be used.

Polyethylene glycols and fatty alcohols like cetyl and/or stearyl alcohol and/or cetostearyl alcohol can also be used as additional substances that influence retardation.

Other pharmaceutically acceptable excipients which are known in the art, such as surfactants, conserving agents, diluents, granulating aids, colorants, aromatic compounds, detergents, buffers and/or anti-sticking agents may also be comprised in the sustained release matrix, if the formulation still provides for a release behaviour in accordance with the invention, i.e. a sustained, invariant and, if several compounds are present, independent release. Such formulations also have to provide good storage stability of the active compounds within the matrix.

If fillers and additional substances such as dyes and the mentioned lubricants, flowing agents and plasticizers are used, care has to be taken that according to the invention only such combinations together with the matrix forming substance and/or the matrix forming substances are used, which ensure release profiles of the active compounds in accordance with the invention.

All these additional components of the formulations will be chosen in such a way that the release matrix receives the character of a substantially non-water- or non-buffer-swellable and non-erosive diffusion matrix.

According to the invention, a formulation is especially preferred that comprises ethylcellulose or Surelease® E-7-7050 as a matrix-building substance, stearyl alcohol as fatty alcohol, magnesium stearate as lubricant, lactose as filler and povidone as a granulating aid.

Matrices that are in accordance with the invention can be used to produce preparations that release active compounds in a sustained, independent and invariant manner and that release equal amounts of the active compounds per time unit. Specifically, this means that in the case of a oxycodone/naloxone combination containing 12 mg oxycodone and 4 mg naloxone, 25% oxycodone and 25% naloxone are released within the first 4 hours. Correspondingly, in the case of a oxycodone/naloxone combination containing 24 mg oxycodone and 8 mg naloxone, 25% oxycodone and 25% naloxone are released during the first 4 hours, with the deviation in both cases being no more than 20% of the mean value (which in this case is 25% oxycodone or naloxone).

Such an equal release behaviour for both active compounds may be desirable for medical aspects.

A preferred embodiment of the invention relates to preparations that release 1% to 40%, preferably 5% to 35%, more preferably between 10% and 30% and even more preferably between 15% and 25% of oxycodone and/or naloxone after 15 minutes. In other preferred embodiments of the invention, 15% to 20%, 20% to 25%, approximately 15%, approximately 20% or approximately 25% of oxycodone and/or naloxone are released after 15 minutes.

Another preferred embodiment of the invention relates to preparations that release between 25% to 65%, preferably between 30% to 60%, more preferably between 35% to 55% and even more preferably between 40% to 50% of oxycodone and/or naloxone after one hour. Preferred embodiments of the invention also relate to preparations that release between 40% to 45%, 45% to 50%, approximately 40%, approximately 45% or approximately 50% of oxycodone and/or naloxone after one hour.

Yet another preferred embodiment of the invention relates to preparations that release between 40% to 85%, preferably between 45% to 80%, more preferably between 45% to 75% and even more preferably between 45% to 55%, 50% to 60%, 55% to 65%, 65% to 75% or 75% to 85% of oxycodone and/or naloxone after 2 hours. Preferred embodiments also comprise preparations that release approximately 45%, approximately 50%, approximately 55%, approximately 60%, approximately 65%, approximately 70%, approximately 75%, approximately 80% or approximately 85% of oxycodone and/or naloxone after 2 hours.

One preferred embodiment of the invention relates to preparations that release 60% to 100%, preferably between 75% to 95%, more preferably between 80% to 95%, and even more preferably between 80% to 90% of oxycodone and/or naloxone after 4 hours. Preferred embodiments of the invention also relate to preparations that release between 80% to 85%, 85% to 90%, approximately 80%, approximately 85% or approximately 90% of oxycodone and/or naloxone after 4 hours.

One preferred embodiment of the invention also relates to preparations that release between 65% to 100%, preferably between 75% to 100%, more preferably between 80% to 95% and even more preferably between 80% to 85%, between 85% to 90% or between 90% to 95% of oxycodone and/or naloxone after 7 hours. Preferred embodiments of the invention also relate to preparations that release approximately 80%, approximately 85%, approximately 90% or approximately 95% of oxycodone and/or naloxone after 7 hours.

Yet another preferred embodiment of the invention relates to preparations that release between 85% to 100%, preferably between 90% to 100%, more preferably between 95% to 100% and even more preferably approximately 95% or 100% of oxycodone and/or naloxone after 12 hours.

Preparations in accordance with the invention can be produced as all common application forms which, on principle, are suitable for retardation formulations and which ensure that the active compounds are released in a manner in accordance with the invention. Especially suitable are tablets, multi-layer tablets and capsules. Additional application forms like granules or powders can be used, with only those applications forms being admissible that provide a sufficient retardation and a release behaviour in accordance with the invention.

Pharmaceutical preparations may also comprise film coatings. However, it has to be ensured that the film coatings do not negatively influence the release properties of the active compounds from the matrix and the storage stability of the active compounds within the matrix. Such film coatings may be colored or may comprise a initial dosage of the active compounds If required. The active compounds of this initial dosage will be immediately released so that the therapeutically effective blood plasma level is reached very quickly. It has to be ensured that, by coating the preparations in accordance with the invention, the release behaviour of the active compounds is not negatively influenced.

The active compounds that are comprised within the formulation in accordance with the invention and which are released in a sustained, invariant and, if several compounds are present, independent manner from the inventive matrix and which are also storage stable within the matrix, are not limited to a special class of compounds.

Pharmaceutically active compounds according to the present invention thus comprise antipyretic, analgesic and anti-inflammatory agents such as indomethacin, aspirin, diclofenac, ibuprofen, antiulcer agents such as sulpiride, coronary vasodilaters such as nifedipine, peripheral vasodilators such as ifenprodil tartrate, antibiotics such as ampicillin, chloramphenicol or erythromycin, synthetic antimicrobial agents such as nalidixic acid, antispasmodic agents such as propantheline bromide, antitussive and antiasthmatic agents such as theophylline or aminophylline, bronchodilators such as diprophylline, diuretics such as furosemide, muscle relaxants such as chlorophenesin carbamate, cerebral metabolism improving agents such meclofenoxate hydrochloride, minor tranquilizers such as oxazolam, diazepam or clotiazepam, major tranquilizers such as sulpiride, beta-blockers such as pindolol, antiarrhythmic agents such as procainamide hydrochloride, anticoagulants such as ticlopidine hydrochloride, antiepileptics such as phenyloin, antihistaminics such as chlorpheniramine maleate, antiemetics such as difenidol hydrochloride, antihypertensive agents such dimethylaminoethyl reserpilinate hydrochloride, sympathomimetic agents such as dihydroergotamine mesilate, expectorants such as bromhexine hydrochloride, oral antidiabetic agents such as glibenclamide, cardio-vascular system drugs such as ubidecarenone, iron preparations such as ferrous sulfate, non stearoidal anti-inflammatory drugs or vitamins. Particularly preferred are analgesics comprising the group of opiates and opioids such as oxycodone, morphine, dihydrocodeine, oxymorphine, buprenorphine or tramadol. Also preferred are analgesic antagonists such as naltrexone or naloxone. Other opioid agonists and antagonists can be found, e.g. in WO 99/32119.

Particularly preferred are formulations in accordance with the invention that comprise opioid analgesics (opioid agonists) and/or opioid antagonists as pharmaceutically active compounds.

According to the invention, opioid analgesics or opioid agonists comprise all compounds that belong to class NO2A of opioid analgesics according to the ATC Classification of the WHO, and that display an analgesic effect upon application in accordance with the invention. Preferably, an opioid agonist is selected from the group of morphine, oxycodone, hydromorphone, propoxyphene, nicomorphine, dihydrocodeine, diamorphine, papavereturn, codeine, ethylmorphine, phenylpiperidine and derivates thereof, methadone, dextropropoxyphene, buprenorphine, pentazocine, tilidine, tramadol, hydrocodone. Further examples for useable analgesics according to the invention are meperidine, oxymorphone, alphaprodine, anileridine, dextromoramide, metopone, levorphanol, phenazocine, etoheptazine, propiram, profadol, phenampromide, thiambuten, pholcodeine, codeine, dihydrocodeinon, fentanyl, 3-trans-dimethylamino-4-phenyl-4-trans-carbethoxy-Λ'-cyclohexen, 3-dimethylamino-0-(4-methoxyphenyl-carbamoyl)-propiophenone oxime, (−)β-2'-hydroxy-2,9-dimethyl-5-phenyl-6,7-benzomorphane, (−)2'-hydroxy-2-(3-methyl-2-butenyl)-9-methyl-5-phenyl-6,7-benzomorphane, pirinitramide, (−)α-5,9-diethyl-2' hydroxy-2-methyl-6,7-benzomorphane, ethyl 1-(2-dimethylaminoethyl)-4,5,6,7-tetrahydro-3-methyl-4-oxo-6-phenyl-indol-2-carboxylate, 1-benzoylmethyl-2,3-dimethyl-3-(m-hydroxy-phenyl)-piperidine, N-allyl -7α (1-R-hydroxy-1-methylbutyl)-6,14-endo-ethanotetrahydronororipavine, (−) 2'-hydroxy-2-methyl-6,7-benzomorphane, noracylmethadol, phenoperidine, α-d1-methadol, α-1-methadol, β-d1-acetylmethadol, α-1-acetylmethadol and β-1-acetylmethadol. These lists are not to be understood as exclusive.

Especially preferred analgesically effective opiod agonists are oxycodone, hydrocodone, hydromorphone, morphine, codeine, dihydrocodeine, methadone, oxymorphone, fentanyl and sufentanyl. Specifically, the opioid agonist is oxycodone.

According to the invention, antagonists comprise such compounds that counteract opioid agonists (as defined earlier). Such compounds can also be found in the ATC Classification of the WHO. According to the invention, compounds are preferred that upon application in accordance with the invention decrease the side effects, the habituation effects and the addictive potential caused by the opioid agonists. Antagonists can comprise among others, naltrexone, naloxone, nalmefene, nalorphine, nalbuphine, naloxoneazinen, methylnaltrexone, ketylcyclazocine, norbinaltorphimine, naltrindol, 6-β-naloxol and 6-β-naltrexol.

Especially preferred antagonists comprise naltrexone, nalmefene and naloxone. Specifically preferred as an antagonist is naloxone.

According to the invention, formulations with a combination of oxycodone as agonist and naloxone as antagonist are particularly preferred. The agonist is preferably in excess compared to the antagonist. The excess of the agonist is defined based on the amount of the unit dosage of the antagonist present in the combination preparation. The extent of the excess of the opioid agonist is usually given in terms of the weight ratio of agonist to antagonist.

In the case of oxycodone and naloxone, preferred weight ratios of agonist to antagonist lie within a weight ratio range of 25:1 at maximum, especially preferred are the weight ratio ranges 15:1, 10:1, 5:1, 4:1, 3:1, 2:1 and 1:1.

The absolute amounts of agonist and antagonist to be used depend on the choice of the active compounds. According to the invention, care has to be taken that agonist and antagonist are released from the pharmaceutical preparation that has been formulated for sustained release, only in an independent and invariant manner.

If oxycodone and naloxone are used for a combination preparation, preferably between 10 and 150 mg, especially preferably between 10 and 80 mg of oxycodone (typical amounts for use) and preferably between 1 and 50 mg naloxone per unit dosage are used.

In other preferred embodiments of the invention, the preparations may comprise between 5 and 50 mg of oxycodone, between 10 and 40 mg of oxycodone, between 10 and 30 mg of oxycodone or approximately 20 mg of oxycodone. Preferred embodiments of the invention may also comprise preparations with between 1 and 40 mg naloxone, 1 and 30 mg naloxone, 1 and 20 mg naloxone or between 1 and 10 mg naloxone per unit dosage.

According to the invention, the ratio between oxycodone and naloxone has to be chosen in such a way that release profiles for both active substances in accordance with the invention are guaranteed and that the agonist can display its analgesic effect while the amount of the antagonist is chosen in such a way that habituation- or addiction-promoting effects and side effects of the agonist are reduced or abolished, without (substantially) affecting the analgesic effect of the agonist. According to the invention, development of habituation and addiction as well as obstipation and breath depression are to be considered as side effects of analgesically effective opioid agonists.

Even though this might not be expressly stated, the term "agonist" or "antagonist" always comprises pharmaceutical acceptable and equally acting derivatives, salts and the like. If, for example, oxycodone or naloxone is mentioned, this also comprises, besides the free base, their hydrochloride, sulfate, bisulfate, tatrate, nitrate, citrate, bitratrate, phosphate, malate, maleate, hydrobromide, hydrojodide, fumarate, succinate and the like.

According to the invention, agonists and antagonists are formulated in a way that they are released from the resulting pharmaceutical preparation in a sustained, independent and invariant manner. This does not mean that the antagonist is in excess compared to the agonist. On the contrary, it is preferred that in formulations comprising an agonist/antagonist combination, that show a release profile in accordance with the invention, the agonist is in excess compared to the antagonist.

Preparations produced according to the invention can be applied orally, nasally, rectally and/or by inhalation for use in pain therapy. According to the invention, parenteral application is not envisaged. Especially preferred is a formulation for oral application.

Formulations in accordance with the invention may be produced by embedding the active compound into the matrix by e.g. melting, spray-freezing, spray-drying, granulating, direct tabletting and/or extrusion.

Pharmaceutical preparations or preliminary stages thereof which are in accordance with the invention can be produced by build-up or break-down granulation. A preferred embodiment is the production by spray granulation with subsequent drying of the granules. Another preferred embodiment is the production of granules by build-up granulation in a drum or on a granulating disk. The granules may then be pressed into e.g. tablets using appropriate additional substances and procedures.

The person skilled in the art is familiar with granulating technology as applied to pharmaceutical technology. The embodiment examples (see below) disclose specific embodiments of the invention. However, it is well within the scope of the person skilled in the art to adapt the parameters of the process in order to achieve specific purposes.

The pharmaceutical formulations in accordance with the invention or precursors thereof may be advantageously produced by extrusion (instead of granulation), since several working steps (such as the drying of the granulates during spray-granulation) may be omitted, so that formulations in accordance with the invention may be produced efficiently and with less cost.

As production of formulations in accordance with the invention by extrusion is a continuous process, several working steps can be omitted (in comparison to other production methods, such as spray-granulation), leading to more efficient production of the formulations in accordance with the invention.

For production of formulations in accordance with the invention by extrusion Surelease®
E-7-7050, which comprises dibutylsebacat as plasticizer and additional other components may be omitted and ethylcellulose may be directly used, resulting in a cheaper and more efficient production process.

Production of pharmaceutical preparations or preliminary stages thereof, which are in accordance with the invention, by extrusion technology is especially advantageous. In one preferred embodiment, pharmaceutical preparations or preliminary stages thereof are produced by melt extrusion with co- or counter-rotating extruders comprising two screws. Another preferred embodiment is the production by means of extrusion, with extruders comprising one or more screws. These extruders may also comprise kneading elements.

Extrusion is also a well-established production process in pharmaceutical technology and is well known to the person skilled in the art. The person skilled in the art is well aware that during the extrusion process, various parameters, such as the feeding rate, the screw speed, the heating temperature of the different extruder zones (if available), the water content, etc. may be varied in order to produce products of the desired characteristics. The Example section provides for numerous examples of preparations according to the invention that have been produced by extrusion.

The aforementioned parameters will depend on the specific type of extruder used. For production of formulations in accordance with the invention, extrusion may be performed with one or multiple screw extruders which may be counter-rotating or co-rotating screws. The feeding rate of the components is dependent on the specific extruder type.

The aforementioned parameters will depend on the specific type of extruder used. During extrusion the temperature of the heating zones, in which the components of the inventive formulation melt, may be between 40 to 120° C., preferably between 50 to 100° C., more preferably between 50 to 90° C., even more preferably between 50 to 70° C. and most preferably between 50 to 65° C., particularly if counter-rotating twin screw extruders (such as a Leistritz Micro 18 GGL) are used. The person skilled in the art is well aware that not every heating zone has to be heated. Particularly behind the feeder where the components are mixed, cooling at around 25° C. may be necessary. The screw speed may vary between 100 to 500 revolutions per minute (rpm), preferably between 100 to 250 rpm, more preferably between 100 to 200 rpm and most preferably around 150 rpm, particularly if counter-rotating twin screw extruders (such as a Leistritz Micro 18 GGL) are used. The geometry and the diameter of the nozzle may be selected as required. The diameter of the nozzle of commonly used extruders typically is between 1 to 10 mm, preferably between 2 to 8 mm and most preferably between 3 to 5 mm. The different extruders may differ with respect to their set up and comprise e.g. kneading elements. The ratio of length versus diameter of the screw of extruders that may be used for production of inventive preparations is typically around 40:1.

Typical screw profiles which may be used in the production of formulations according to the invention by extrusion are shown in FIGS. 1A and 1B. Extrusion procedures for the production of pharmaceutical preparations which show a sustained release are well known to the person skilled in the art.

In a preferred embodiment, a counter-rotating twin-screw extruder is used for the production of formulations in accordance with the invention. This may be e.g. an extruder of the type Micro 18 GGL (Leistritz AG, Nürnberg, Germany). For this preferred embodiment the extruder has no kneading elements (see also FIG. 1A). The feeding rate of the components used for the production of the formulation in accordance with the invention is between 1-3 kg/h, preferably between 1-2 kg/h. Particularly preferred is a feeding rate of 1.5 kg/h. The temperature of the heating zones is between 40°-120° C., 50°-100° C., preferably 50°-90° C., more preferably 50°-70° C. Particularly preferred are 50°-65° C. The extruder provides for 10 heating zones. In the first heating zone the components are generally cooled around 25° C. The temperature in the other heating zones will then preferably be around 50°-65° C. and may vary for every heating zone. The screw speed will be between 1-500 rpm, preferably between 1-250 rpm, more preferably between 120-200 rpm and even more preferably around 150 rpm. The diameter of the nozzle will be between 1-10 mm, preferably between 2-8 mm, or between 3-5 mm. In a particularly preferred embodiment of the invention, the diameter of the nozzle is approximately 3 mm.

Generally, the temperatures of the heating zones have to be selected such that no temperatures develop that may destroy the pharmaceutically active compounds. The feeding rate and screw speed will be selected such that the pharmaceutically active compounds are released from the preparations produced by extrusion in a sustained, independent and invariant manner and are storage stable in the matrix. If e.g. the feeding rate is increased, the screw speed may have to be increased correspondingly to ensure the same retardation.

The person skilled in the art knows that all the aforementioned parameters depend on the specific production conditions (extruder type, screw geometry, number of components etc.) and may have to be adapted such that the preparations produced by extrusion provide for a sustained, independent and invariant release as well as for the afore-mentioned storage stability. The person skilled in the art knows how to properly adjust the aforementioned parameters The person skilled in the art can infer from the Examples (see below) that by changing the parameters during extrusion and by changing the composition with respect to the compounds that are substantially responsible for the release behaviour of the preparations, preparations with different release profiles may be obtained. Thus, the present invention allows to first produce a preparation with a desired release profile for oxycodone and naloxone or naloxone alone by e.g. varying the amount of fatty alcohols or the matrix-forming polymer ethylcellulose as well as production parameters such as temperature, screw speed (during extrusion) or pressure power during tablet production.

Once a preparation with the desired release profile has been obtained, the inventive preparations according to the invention allow the person skilled in the art to change the amounts of the preparations with respect to the active compounds as outlined above. Preparations comprising different amounts of the active compounds but of otherwise substantially equal composition, however, will then provide for the features of sustained, invariant and independent release.

The Example section therefore discloses numerous examples showing that preparations with different release profiles may be obtained by changing the amount of e.g. ethylcellulose. Other examples show that once a preparation has been established with desired release profiles, the change in the amount of naloxone will not influence the release behaviour of such preparations if the difference in the amount of the active compound is replaced by pharmaceutically inert excipients such as lactose.

The production of formulations in accordance with the invention by extrusion is preferred with the formulations comprising opioid analgesics and opioid antagonists as active compounds. Particularly preferred is the production of formulations in accordance with the invention that comprise oxycodone and naloxone, wherein the preferred weight ratios of agonist to antagonist are within a weight ratio ranging from maximal 25:1, preferably of 20:1, 15:1, 10:1, 5:1, 2:1 and 1:1.

A preferred embodiment of the invention refers to a preparation that comprises the inventive matrix and naloxone as the pharmaceutically active compound. Such preparations may be advantageously used for a variety of different indications.

Preparations according to the invention comprising an opioid antagonist such as naloxone as the pharmaceutically active compound may e.g. be used for complete or partial treatment of opioid-induced side effects. Such side effects may comprise dizziness, breath depression, opioid-abuse, development of tolerance and addiction and particularly obstipation.

Preparations according to the invention which comprise naloxone as a pharmaceutically active compound preferably are used for the treatment of opioid-induced obstipation. Almost 90% of patients under opioid treatment show signs of obstipation which may be responsible for other additional ailments such as discomfort, tension and pain in the abdomen, nausea and emesis, anorexia, haemorrhoids, anal fissures, fecal incontinence, paradoxic diarrhoea, urine retention, intestinal pseudo obstruction, and decubitus of the colon which may lead to perforation (Neuenschander et. al. (2002), Palliativmedizin auf einen Blick, Schweizerische Krebsliga).

So far opioid-induced obstipation has been treated by the application of laxatives. However, application of typical laxatives does not allow for the simultaneous treatment of other opioid-induced side effects.

The advantage of the use of inventive preparations comprising naloxone is that the inventive preparations allow for a sustained release of the antagonist naloxone. If e.g. patients in pain are treated simultaneously with opioid analgesics, application of such preparations comprising naloxone will allow for a long term treatment of opioid-induced side effects including obstipation. Particularly, the application of naloxone as a sustained release formulation should allow for an efficient treatment of opioid-induced obstipation. At the same time it is ensured that there is no tolerance development towards opioid analgesics if applied simultaneously. Moreover, the use of naloxone does not lead to any disturbances in the water and electrolyte metabolism and does not induce colon irritation.

The provision of a sustained release formulation comprising naloxone as the only pharmaceutical active agent compound also has the advantage that patients that are treated with opioid analgesics may receive a dosis of naloxone which is sufficient to counteract the opioid-induced side effects without leading to a significant reduce of analgesia. With inventive preparations being available which comprise different amounts of naloxone, one has the possibility to specifically treat patients in need of pain treatment that receive different amounts of opioid agonists or are treated with different opioid agonists Yet another preferred embodiment of the invention relates to the use of inventive preparations comprising naloxone for treatment of opioid-induced pruritus. Opioid-induced puritus is one of the side effects that is experienced by the patients as extremely unpleasant.

In another embodiment of the invention, preparations comprising naloxone may also be used for treatment of idiopathic syndromes such as idiopathic pruritus or pruritus due to cholestasia and/or renal dysfunction. These preparations may also be used for the treatment of chronic idiopathic obstipation or irritable bowel syndrome. Thus, preparations in accordance with the invention comprising naloxone as a pharmaceutically active compound may be used for a multitude of therapeutic indications and purposes which may be either opioid-induced or not. As the inventive preparations provide for a sustained and reproducibly invariant release behaviour, they allow for an efficient treatment of the aforementioned syndromes.

In a preferred embodiment preparations in accordance with the invention comprising naloxone as the active compound release 30% to 60%, preferably 35% to 55%, more preferably 40% to 50% and even more preferably 40% to 45% or 45% to 50% of naloxone after 90 minutes. In another preferred embodiment of the invention, preparations comprising naloxone release approximately 40%, approximately 45% or approximately 50% of the active compound after 90 minutes.

In another preferred embodiment preparations in accordance with the invention comprising naloxone release 30% to 70%, preferably 35% to 65% and more preferably between 40% to 60% of naloxone after 120 minutes. In yet another embodiment of the invention, preparations comprising naloxone release preferably between 35% to 40%, 40% to 45% and 45% to 50% of naloxone after 120 minutes. In another preferred embodiment of the invention the preparations comprising naloxone release approximately 35%, approximately 40%, approximately 45%, approximately 50% or approximately 55% of naloxone after 120 minutes.

In another preferred embodiment preparations in accordance with the invention comprising naloxone release 55%-90%, preferably 60% to 80%, more preferably 65% to 75% and even more preferably 65% to 70% or 70% to 75% of naloxone after 420 minutes. In yet another preferred embodiment of the invention, preparations comprising naloxone release approximately 65%, approximately 70% or approximately 75% of naloxone after 420 minutes.

In another preferred embodiment preparations in accordance with the invention comprising naloxone release 60% to 90%, preferably 65% to 85%, more preferably 70% to 80% and even more preferably 75% to 80% of naloxone after 600 minutes. In yet another preferred embodiment of the invention, preparations comprising naloxone release approximately 75%, approximately 80% or approximately 85% of naloxone after 600 minutes.

The invention can be illustrated by the following embodiments enumerated in the numbered paragraphs below:

1. Storage stable pharmaceutical formulation comprising at least one pharmaceutically active compound in a diffusion matrix, characterized in that the matrix is determined with respect to its essential release characteristics by ethylcellulose or an ethylcellulose-based polymer and at least one fatty alcohol and that the active compounds are released from the substantially non-swellable diffusion matrix in a sustained, invariant and, if several compounds are present, independent manner.

2. Pharmaceutical formulation according to embodiment 1, characterized in that the fatty alcohol comprises lauryl, myristyl, stearyl, cetylstearyl, ceryl and/or cetylalcohol, preferably stearyl alcohol.

3. Pharmaceutical formulation according to embodiment 1 or 2, characterized in that the formulation comprises ethylcellulose.

4. Pharmaceutical formulation according to one of the preceding embodiments, characterized in that the formulation does not comprise relevant amounts of alkaline and/or water-swellable substances, particularly derivatives of acrylic acid and/or hydroxyalkylcelluloses.

5. Pharmaceutical formulation according to one of the preceding embodiments, characterized in that the formulation comprises common pharmaceutical excipients, particularly fillers, lubricants, flowing agents and/or plasticizers.

6. Pharmaceutical formulation according to embodiment 5, characterized in that the fillers are selected from the group comprising sugars, preferably lactose, glucose and/or saccharose, starches and hydrolysates thereof, preferably micro-crystalline cellulose and/or cellactose, sugar alcohols, preferably sorbitol and/or mannitol, poorly soluble calcium salts, preferably calcium hydrogenphosphate, dicalciumphosphate or tricalciumphosphate and/or povidone.

7. Pharmaceutical formulation according to embodiment 5, characterized in that it comprises magnesium stearate, calcium stearate and/or calcium laureate and/or fatty acids, preferably stearic acid as lubricant.

8. Pharmaceutical formulation according to embodiment 5, characterized in that it comprises highly dispersed silica, preferably Aerosil®, talcum, corn starch, magnesium oxide, magnesium and/or calciumstearate as flowing agent.

9. Pharmaceutical formulation according to embodiment 5, characterized in that it comprises dibutyl sebacate as plasticizer.

10. Pharmaceutical preparation according to one of the preceding embodiments, characterized in that the formulation can be stored over a period of at least two years under standard conditions (60% relative humidity, 25° C.) in accordance with admission guidelines.

11. Pharmaceutical preparation according to one of the preceding embodiments, characterized in that it comprises opioid analgesics as the pharmaceutically active compounds, preferably morphine, oxycodone, hydromorphone, propoxyphene, nicomorphine, dihydrocodeine, diamorphine, papaveretum, codeine, ethylmorphine, phenylpiperidine and/or derivatives thereof, methadone, dextropropoxyphene, buprenorphine, pentazocin, tilidine, tramadol and hydrocodone and/or opioid antagonists, preferably naltrexone, naloxone, nalmefene, nalorphine, nalbuphin, naloxonazinene, methylnaltrexone, ketylcyclazocine, norbinaltorphimine, naltrindol, 6-β-naloxol and/or 6-β-naltrexol.

12. Pharmaceutical formulation according to embodiment 11, characterized in that the opioid analgesic and/or the antagonist are present in the form of their pharmaceutically acceptable and equally active derivatives, such as the free base, salts and the like, preferably as the hydrochloride, sulfate, bisulfate, tatrate, nitrate, citrate, bitatrate, phosphate, malate, maleate, hydrobromide, hydroiodide, fumarate or succinate.

13. Pharmaceutical formulation according to embodiment 11 or 12, characterized in that the formulation comprises at least two active compounds which are oxycodone and naloxone, and wherein oxycodone is present in an amount ranging from 10 to 150 mg, preferably from 10 to 80 mg and naloxone is present in an amount ranging from 1 to 50 mg per unit dosage.

14. Pharmaceutical formulation according to embodiment 13, characterized in that it comprises oxycodone and naloxone in a weight ratio ranging from maximal 25:1, preferably maximal 20:1, 15:1 and more preferably from 5:1, 4:1, 3:1, 2:1 and 1:1.

15. Pharmaceutical formulation according to embodiment 11 or 12, characterized in that it contains oxycodone and naloxone with oxycodone being present in an amount ranging from 10 to 150 mg, preferably from 10 to 80 mg and naloxone being present in an amount ranging from 1 to 50 mg.

16. Pharmaceutical preparation according to one of the preceding embodiments, characterized in that the formulation is a tablet, preferably a multi-layered tablet, a capsule, a dragée, a granulate and/or a powder.

17. Pharmaceutical formulation according to embodiment 16, characterized in that the pharmaceutical preparation is suitable or oral, nasal and/or rectal application.

18. Pharmaceutical formulation according to one of the preceding embodiments, characterized in that the formulation is produced by build-up and/or break-down granulation, preferably by spray granulation.

19. Pharmaceutical formulation according to one of embodiments 1 to 17, characterized in that the formulation is produced by extrusion.

20. Storage stable pharmaceutical formulation comprising at least one active compound in a sustained release matrix, characterized in that the matrix is a substantially non-swellable diffusion matrix whose release characteristics are determined by amounts of ethylcellulose or an ethylcellulose-based polymer and at least one fatty alcohol as matrix components, and by extrusion or granulation of the matrix materials together with the amount of the active compounds for formation of an active compound-containing matrix.

21. Storage stable pharmaceutical formulation according to embodiment 20, wherein the diffusion matrix is a substantially non-erosive matrix.

22. Storage stable pharmaceutical formulation according to embodiment 20 or 21, wherein the matrix material contains ethylcellulose.

23. Storage stable pharmaceutical formulation according to one of embodiments 20 to 22, wherein the matrix is formed by extrusion, particularly by melt extrusion.

24. Storage stable pharmaceutical formulation having an effective amount of an opioid agonist and/or an opioid antagonist in a substantially non-swellable and non-erosive diffusion matrix, whose release characteristics are determined by amounts of ethylcellulose or an ethylcellulose-based polymer and at least one fatty alcohol.

25. Storage stable pharmaceutical formulation according to embodiment 24 having an effective amount of oxycodone and/or naloxone, with oxycodone being present in an amount ranging from 10 to 150 mg, preferably from 10 to 80 mg and naloxone being present in an amount ranging from 1 to 50 mg per unit dosage.

26. Storage stable pharmaceutical formulation according to embodiment 24 or 25 having an effective amount of oxycodone and/or naloxone, wherein oxycodone and naloxone are present in a weight ratio ranging from maximal 25:1, preferably maximal 20:1, 15:1, particularly preferably 5:1, 4:1, 3:1, 2:1 and 1:1.

27. Method for producing a formulation according to one of embodiments 1 to 26,
characterized in that granulation, preferably build-up and/or break-down granulation, particularly preferably spray granulation is used.

28. Method of producing a formulation according to one of embodiments 1 to 26, being an extrusion method, wherein counter-rotating or co-rotating single or multiple screw extruders with/without kneading elements are used.

29. Method according to embodiment 28,
being an extrusion method wherein counter-rotating twin-screw extruders, preferably without kneading elements, are used.

30. Method according to embodiment 28 or 29,
characterized in that the temperature of the heating zones of the extruders is between 20°-120° C., preferably between 50°-100° C., more preferably between 50°-90° C. and even more preferably between 50°-70° C.

31. Method according to one of embodiments 28 to 30,
characterized in that the diameter of the nozzle on the extruder is between 1 to 10 mm, preferably between 2 to 8 mm and particularly preferably between 3 to 5 mm.

32. Method according to one of embodiments 28 to 31,
characterized in that the resulting temperature in the extruder does not influence the stability of the active compounds.

33. Method of producing a pharmaceutical dosage form for the treatment of opioid-induced side effects, characterized in that
the pharmaceutical dosage form comprises a pharmaceutical formulation according to one of embodiments 1 to 10.

34. Method according to embodiment 33, characterized in that
the preparation is used for treatment of opioid-induced obstipation and preferably for treatment of opioid-induced pruritus.

35. Method of producing a pharmaceutical dosage form for the treatment of idiopathic syndromes, characterized in that
the pharmaceutical dosage form comprises a pharmaceutical formulation according to one of embodiments 1 to 10.

36. Method according to embodiment 35, characterized in that
the preparation is used for treatment irritable bowel syndrome, preferably for treatment of idiopathic pruritus or pruritus due to cholestasia and/or renal dysfunction.

37. Method according to one of embodiments 33 to 36, characterized in that
the matrix is a substantially non-swellable diffusion matrix whose release characteristics are determined by amounts of ethylcellulose or an ethylcellulose-based polymer and of at least one fatty alcohol.

38. Method according to one of embodiments 33 to 37, characterized in that
the preparation comprises between approximately 1 to 50 mg naloxone, preferably between approximately 5 to 30 mg naloxone and even more preferably between approximately 5 to 20 mg naloxone.

39. Method according to one of embodiments 33 to 38, characterized in that
naloxone is present in the form of its pharmaceutically acceptable and equally active derivatives, such as the free base, salts and the like, preferably as the hydrochloride, sulfate, bisulfate, tatrate, nitrate, citrate, bitatrate, phosphate, malate, maleate, hydrobromide, hydroiodide, fumarate or succinate.

40. Method according to one of embodiments 33 to 39, characterized in that
the matrix is produced by extrusion.

Examples that display highly advantageous embodiments of the invention are set out below. Examples are also given showing that formulations which are in accordance with the invention differ mainly in their structure from formulations with a sustained release which has been produced by using commonly used scaffold-forming polymers. Only the formulations produced in accordance with the invention provide for a sustained, invariant and, if several compounds are present, independent release of the active compounds with the formulation being storage stable. The examples are not to be interpreted as limiting the possible embodiments of the invention.

4. EXAMPLES

Example 1

Production of Tablets with Different Oxycodone/Naloxone Amounts in a Non-Swellable Diffusion Matrix by Spray Granulation The following amounts of the listed components were used for the production of oxycodone/naloxone tablets according to the invention.

|  | Preparation (designation) | | |
|---|---|---|---|
|  | Oxy/Nal-0 | Oxy/Nal-5 | Oxy/Nal-10 |
| oxycodone HCl | 20.0 mg | 20.0 mg | 20.0 mg |
| naloxone HCl | — | 5.0 mg | 10.0 mg |
| Lactose Flow Lac 100 | 59.25 mg | 54.25 mg | 49.25 mg |
| Povidone 30 | 5.0 mg | 5.0 mg | 5.0 mg |
| Surelease ® | 10.0 mg solid material | 10.0 mg solid material | 10.0 mg solid material |
| Stearyl alcohol | 25.0 mg | 25.0 mg | 25.0 mg |
| Talcum | 2.5 mg | 2.5 mg | 2.5 mg |
| Mg-Stearate | 1.25 mg | 1.25 mg | 1.25 mg |

The Surelease® E-7-7050 polymer mixture used had the following composition.

| Surelease ® |
|---|
| Ethylcellulose 20 cps |
| Dibutylsebacate |
| Ammoniumhydroxide |
| Oleic acid |
| Siliciumdioxide |
| Water |

For the production of tablets oxycodone HCl, naloxone HCl, Povidone 30 and Lactose Flow Lac 100 were mixed in a tumbling mixer (Bohle) and subsequently spray-granulated with Surelease® E-7-7050 in a fluidized bath granulating device (GPCG3). The material was sieved over a Comill 1.4 mm sieve. An additional granulation step was carried out with melted fatty alcohol in a high-shear mixer (Collette). All tablet cores produced by this approach had a weight of 123 mg, based on dry substance.

Example 2

Production of Tablets with Oxycodone and Naloxone in a Non-Swellable Diffusion Matrix by Extrusion The following amounts of the listed components were used for the production of the oxycodone/naloxone tablets according to the invention.

| Preparation (designation) | Oxy/Nal-Extr |
|---|---|
| oxycodone HCl | 20 mg |
| naloxone HCl | 10 mg |
| Kollidon 30 | 6 mg |
| Lactose Flow Lac 100 | 49.25 mg |
| Ethylcellulose 45 cpi | 10 mg |
| Stearyl alcohol | 24 mg |
| Talcum | 2.5 mg |
| Mg-Stearate | 1.25 mg |

The listed amounts of oxycodone HCl, naloxone HCl, ethylcellulose 45 cpi, Povidone 30, stearyl alcohol and Lactose Flow Lac 100 were mixed in a tumbling mixer (Bohle). This mixture was subsequently extruded with a counter-rotating twin screw extruder of the type Micro 18 GGL (Leistritz AG, Nürnberg, Germany). The temperature of heating zone 1 was 25° C., of heating zone 2, 50° C., of heating zones 3 to 5, 60° C., of heating zones 6 to 8, 55° C., of heating zone 9, 60° C. and of heating zone 10, 65° C. The screw rotating speed was 150 revolutions per minute (rpm), the resulting melt temperature was 87° C., the feed rate was 1.5 kg/h and the diameter of the nozzle opening was 3 mm. The extruded material was sieved with a Frewitt 0.68×1.00 mm sieve. The grinded extrudate was then mixed with talcum and magnesium stearate that had been added over a 1 mm hand sieve and was subsequently pressed into tablets. The extruder has a screw geometry, as shown in FIG. 1A.

In comparison to the oxycodone/naloxone tablets which also have the Surelease®-based non-swellable diffusion matrix produced by spray granulation (see Example 1), extruded preparations comprise less components.

Example 3

Release Profile of the Oxycodone/Naloxone Tablets from Example 1

The release of the active compounds was measured over a time period of 12 hours, applying the Basket Method according to USP at pH 1.2 using HPLC. Tablets Ox/Nal-0, Ox/Nal-5 and Ox/Nal-10 were tested.

One recognizes from FIG. 2 and the values listed in the Table that in the case of a non-swellable diffusion matrix based on Surelease®, the release rates of different oxycodone amounts, independent of the naloxone amount, remain equal (invariant). Correspondingly, invariant release profiles are observed for naloxone at different oxycodone amounts.

| Time (min) | Ox/Nal-0 Oxy | Ox/Nal-5-O Oxy | Ox/Nal-5-N Nal | Ox/Nal-10-O Oxy | Ox/Nal-10-N Nal |
|---|---|---|---|---|---|
| 0 | 0 | 0 | 0 | 0 | 0 |
| 15 | 26.1 | 24.9 | 23.5 | 22.8 | 24.1 |
| 120 | 62.1 | 63 | 61 | 57.5 | 60.2 |
| 420 | 91.7 | 94.5 | 91.9 | 89.4 | 93.5 |
| 720 | 98.1 | 99.6 | 96.6 | 95.7 | 100.6 |

The release values refer to oxycodone or naloxone (line 2) and are given as percentages. The mean value for the release of naloxone at e.g. 420 min is 92.7%. The maximal deviation at 420 min is 1%. Oxy and Nal stand for oxycodone and naloxone and indicate the active compound which has been measured.

Example 4

Release Profile of Oxycodone/Naloxone Tablets from Example 2 at Different pH-Values The release of active compounds from the tablets was measured over a time period of 12 hours at pH 1.2 or for 1 hour at 1.2 and subsequently for 11 hours at pH 6.5. Release rates were determined by the basket method according to USP using HPLC.

The following release rates were measured for 12 hours at pH 1.2:

| Time (min) | Oxy/Nal-Extr-1,2-O Oxy | Oxy/Nal-Extr-1,2-N Nal |
|---|---|---|
| 0 | 0 | 0 |
| 15 | 24.1 | 24.0 |
| 120 | 62.9 | 63.5 |
| 420 | 92.9 | 93.9 |
| 720 | 96.9 | 98.1 |

The following release rates were measured for 1 hour at pH 1.2 and 11 hours at pH 6.5:

| Time (min) | Oxy/Nal-Extr-6,5-O Oxy | Oxy/Nal-Extr-6,5-N Nal |
|---|---|---|
| 0 | 0 | 0 |
| 60 | 48.1 | 49.2 |
| 120 | 65.0 | 64.7 |
| 240 | 83.3 | 81.8 |
| 420 | 94.1 | 92.3 |

The release rates refer to oxycodone and naloxone (line 2) and are given as percentages. Oxy and Nal stand for oxycodone and naloxone and indicate the active compound measured.

The comparison of the values given in the Tables of Example 4 and the Table of Example 3 make clear that independent of the production process, active compounds are released in equal amounts from the preparations. For example, 89.4% of oxycodone is released from spray-granulated tablets (Ox/Nal-10-tablets, see Example 3) at 420 minutes, while 92.9% is released from extruded tablets (Oxy/Nal-Extr-1.2-O, Example 4) at 420 minutes. The release of oxycodone from extruded tablets thus deviates by 1.1% from the mean value of the release of oxycodone from spray-granulated tablets (91.9% at 420 minutes). 93.5% of naloxone is released from spray-granulated tablets (Ox/Nal-10-tablets, see Example 3) at 420 minutes, while 93.9% is released from extruded tablets (Oxy/Nal-Extr.-1.2-O, Example 4) at 420 minutes. The release of naloxone from extruded tablets thus deviates by 1.3% from the mean value of the release of naloxone from spray-granulated tablets (92.7% at 420 minutes).

Moreover, one can infer from a comparison of the values of the Tables of Example 4 and from FIGS. 3A and 3B that independent of the pH value at which the release rates have been measured the release of oxycodone and naloxone remain equal and invariant.

Example 5

Comparative Example: Release Behaviour of Valoron® Tablets

The release of the active substances from tablets was monitored over a time period of 7 hours. Valoron® tablets with 50 mg tilidine and 4 mg naloxone (Ti/Nal-50/4) or 100 mg tilidine and 8 mg naloxone (Ti/Nal-100/8) or 150 mg tilidine and 12 mg naloxone (Ti/Nal-150/12) were tested by the Basket Method according to USP for 1 h at pH 1.2 and then for additional 6 h at pH 6.5 using HPLC.

One recognizes from FIGS. 4A and 4B and the values listed in the Table that in case of a swellable (and possibly erosive) diffusion matrix with relevant amounts of HPMC, the release of different amounts of tilidine varies significantly and is not invariant for different amounts of naloxone. This applies in turn to naloxone. This means that for this pH the release of the active compounds is not independent of each other.

| Time (min) | Ti/Nal-50/4-T Til | Ti/Nal-50/4-N Nal | Ti/Nal-100/8-T Til | Ti/Nal-100/8-N Nal | Ti/Nal-150/12-T Til | Ti/Nal-150/12-N Nal |
| --- | --- | --- | --- | --- | --- | --- |
| 0 | 0 | 0 | 0 | 0 | 0 | 0 |
| 60 | 37.2 | 27.6 | 33.9 | 27.3 | 29.9 | 23.3 |
| 120 | 47.6 | 31.7 | 46.5 | 33.4 | 41.5 | 28.5 |
| 180 | 54.7 | 37.4 | 55 | 41.2 | 48.2 | 35 |
| 240 | 59.7 | 44 | 68.2 | 59.5 | 54.5 | 40.1 |
| 300 | 65.2 | 50.6 | 82.6 | 72.9 | 60.5 | 47.5 |
| 360 | 70.3 | 58 | 85.7 | 82.7 | 67.2 | 56.4 |
| 420 | 74.2 | 60.8 | 93.1 | 90.9 | 84.9 | 78.9 |

The release values refer to tilidine or naloxone (line 2) and are given as percentages. The mean value for the release of naloxone at e.g. 420 min is 78,87%. The maximal deviation at 420 min is 20.4%. Til and Nal stand for tilidine and naloxone and indicate the active compound tested.

Example 6

Structure Comparison of Tablets of Examples 1 and 2 with Valoron® N Tablets by Electron Microscopy For electron microscopy tablets were used that comprised 20 mg oxycodone and 10 mg naloxone and were produced either by spray granulation according to Example 1 (Ox/Nal-10) or by extrusion according to Example 2 (Oxy/Nal-Extr). Additionally, a Valoron® N tablet with 100 mg Tilidin and 8 mg Naloxone was used. FIGS. 5A and 5B show different magnifications of scanning electron microscopy pictures of a Ox/Nal-10-tablet with a formulation according to the invention which was produced by spray granulation. FIGS. 6A and 6B show different magnifications of scanning electron microscopy pictures of a Oxy/Nal-Extr-tablets with a formulation according to the invention, which was produced by extrusion. FIGS. 7A and 7B show scanning electron microscopy pictures of the Valoron® N-tablet.

From a comparison of the figures one can clearly see that tablets with a formulation according to the invention have a surface which is substantially finer and more homogeneously structured and which shows fewer cracks than the Valoron® tablet, regardless of whether the tablets have been produced by spray granulation or extrusion. The structural difference is possibly the reason for the different release behaviours of the different preparations.

Example 7

Production of Tablets Comprising Different Amounts of Naloxone and Different Matrices by Spray Granulation The following amounts of the listed components were used for the production of naloxone tablets:

| | Preparation (designation) | | |
| --- | --- | --- | --- |
| | Nal-5-Eud | Nal-5-Sure | Nal-10-Sure |
| naloxone HCl | 5.0 mg | 5.0 mg | 10.0 mg |
| Lactose Flow Lac 100 | 74.25 mg | 74.25 mg | 69.25 mg |
| Povidone 30 | 5.0 mg | 5.0 mg | 5.0 mg |
| EUDRAGIT ® RS 30D | 10 mg solid material | — | — |
| Surelease ® | — | 10 mg solid material | 10 mg solid material |
| Triacetin | 2.0 mg | — | — |
| Stearyl alcohol | 25.0 mg | 25.0 mg | 25.0 mg |
| Talcum | 2.5 mg | 2.5 mg | 2.5 mg |
| Mg-Stearate | 1.25 mg | 1.25 mg | 1.25 mg |

EUDRAGIT®RS 30 D can be purchased from Röhm GmbH, Darmstadt. Surelease® can be purchased from Colorcon Ltd., Idstein.

EUDRAGIT® RS 30 D or. Surelease®-Polymer mixtures of the following compositions were used:

| EUDRAGIT ® RS 30 D | Surelease ® |
| --- | --- |
| Ammoniomethacrylate copolymer B | Ethylcellulose 20 cps |
| Sorbic acid | Dibutylsebacate |
| Natriumhydroxide | Ammoniumhydroxide |
| Water | Oleic acid |
| | Siliciumdioxide |
| | Water |

For the production of tablets, naloxone HCl, Povidone 30 and Lactose Flow Lac 100 were mixed in a tumbling mixer (Bohle) and subsequently spray-granulated with EUDRAGIT®RS 30 D or Surelease® in a fluidized bath granulating device (GPCG3). An additional granulation step was carried out with melted fat alcohol in a high-shear mixer (Collette). All tablet cores produced by this approach had a weight of 125 mg, referred to the dry substance.

Example 8

Production of Tablets with Naloxone in a Non-Swellable Diffusion Matrix by Extrusion The following amounts of the listed components were used for the production of naloxone tablets according to the invention.

| Preparation (designation) | Nal-Extr |
|---|---|
| naloxone HCl | 10 mg |
| Lactose Flow Lac 100 | 70.25 mg |
| Kollidone 30 | 5 mg |
| Ethylcellulose 45 cpi | 8 mg |
| Stearyl alcohol | 26.0 mg |
| Talcum | 2.5 mg |
| Mg-Stearate | 1.25 mg |

The listed amounts of naloxone HCl, ethylcellulose 45 cpi, Kollidone 30, stearyl alcohol and Lactose Flow Lac 100 were mixed in a tumbling mixer (Bohle). This mixture was subsequently extruded with a counter-rotating twin screw extruder of the type Micro 18 GGL (Leistritz AG, Nürnberg, Germany). The temperature of heating zone 1 was 25° C., of heating zone 2, 50° C., of heating zones 3 to 10, 55° C. The screw rotating speed was 140 rpm, the resulting melt temperature was 65° C., the feed rate was 1.25 kg/h and the diameter of the nozzle opening was 3 mm. The extruded material was sieved with a Frewitt 0.68×1.00 mm sieve. The grinded extrudate was then mixed with talcum and magnesium stearate that had been added over a 1 mm hand sieve and was subsequently pressed into tablets. The extruder has a screw geometry, as shown in FIG. 1B.

In comparison to the oxycodone/naloxone tablets which also have the Surelease®-based non-swellable diffusion matrix produced by spray granulation (see Example 7), extruded preparations comprise less components.

Example 9

Release Behaviour of Naloxone Tablets from Example 7

The release of the active compound was measured over a time period of 16 hours, applying the Basket Method according to USP at pH 1.2 using HPLC. Two tablets (designated A and B) of Nal-5-Eud, Nal-5-Sure and Nal-10-Sure were tested.

One recognizes from FIGS. 8A and 8B and the values listed in the Table that in the case of a non-swellable diffusion matrix based on Surelease®, the release rates of naloxone independent of the absolute amount reproducibly do not change and remain substantially equal (invariant). This does not apply for the release of naloxone from matrix based on Eudragit®.

| Time (min) | Nal-5-Eud-A | Nal-5-Eud-B | Nal-5-Sure-A | Nal-5-Sure-B | Nal-10-Sure-A | Nal-10-Sure-B |
|---|---|---|---|---|---|---|
| 0 | 0 | 0 | 0 | 0 | 0 | 0 |
| 15 | 18.48 | 18.23 | 23.86 | 21.97 | 20.65 | 22.25 |
| 90 | 40.46 | 26.15 | 46.74 | 47.33 | 45.18 | 45.98 |
| 240 | 62.43 | 53.47 | 70.48 | 69.49 | 69.13 | 68.76 |
| 420 | 82.9 | 72.27 | 91.04 | 88.69 | 88.06 | 87.5 |
| 720 | 97.46 | 85.74 | 100.62 | 99.1 | 96.05 | 95.74 |
| 960 | 107.6 | 96.26 | 102.26 | 102.33 | 97.91 | 97.43 |

The release values refer to naloxone and are given as percentages. The mean value for the release of naloxone in the case of e.g. Nal-Sure tablets at 90 min is 46.3%. The maximal deviation at 90 min is 2.2%. The mean value at this time point for Nal-Eud tablets is 33.3% and the deviation is 21.5%.

Example 10

Release Behaviour of Naloxone Tablets from Example 8

The release of the active compound was measured for different tablets over a time period of 12 hours, applying the Basket Method according to USP at pH 1.2 using HPLC.

One recognizes from FIG. 9 and the values listed in the Table that the release of naloxone independent of the production process reproducibly does not change when tablets have been produced by extrusion.

| Zeit (min) | Nal-Extr-A | Nal-Extr-B | Nal-Extr-C |
|---|---|---|---|
| 0 | 0 | 0 | 0 |
| 15 | 15 | 15 | 14.3 |
| 120 | 40.7 | 41.9 | 40.1 |
| 420 | 72 | 75.2 | 73.6 |
| 720 | 90.1 | 92.4 | 91.2 |

The release values refer to naloxone and are given as percentages. The mean value for the release of naloxone in the case of Nal-Extr tablets at 120 min is 40.9%. The maximal deviation at 120 min is 2.4%.

Example 11

Structure Comparison of Naloxone Tablets of Examples 7 and 8

For electron microscopy, Nal-Eud tablets according to Example 7 with 5 mg (Nal-5-Eud) as well as a Nal-Extr tablets according to Example 8.

FIGS. 10A and 10B show different magnifications of scanning electron microscopy pictures of a Nal-5-Eud tablet. FIGS. 11A and 11B show different magnifications of scanning electron microscopy pictures of a Nal-Extr tablets with a formulation in accordance with the invention.

From a comparison of the figures, one can clearly see that the formulation in accordance with the invention has a surface which is substantially finer and more homogeneously structured. Particularly, in FIGS. 10A and 10B naloxone blooms can be seen, but not in FIGS. 11A and 11B. This structural difference is possibly the reason for the different release behaviour of the different preparations.

Example 12

Structure Comparison of Naloxone Granulates of Examples 7 and 8

For electron microscopy, granulates as they were used for production of Nal-Sure tablets according to Example 7 with 10 mg naloxone (Nal-10-Sure) and Nal-Extr tablets according to Example 8 were used.

FIGS. 12A and 12B show different magnifications of scanning electron microscopy pictures of Nal-10-Sure granulates. FIGS. 13A and 13B show different magnifications of scanning electron microscopy pictures of a Nal-Extr granulates with a formulation in accordance with the invention.

One can clearly see that independent of the production process granulates with a formulation in accordance have homogeneously structured surfaces without major cracks or blooms. Without wanting to be bound to a scientific theory it is assumed that the surface characteristics are responsible for the release behaviour of the formulations in accordance with the invention.

Example 13

Storage Stability of Naloxone Tablets Depending on the Matrix Used

Multiple tablets comprising either EUDRAGIT®RS 30 D or Surelease® and 5 mg naloxone were produced as described in Example 1. The tablets were stored at 25° C. and 60% relative humidity. At different time points, the release behaviour was tested as described in Example 4.

As can be recognized from FIGS. 14A and 14B and the Tables, the release profiles of naloxone tablets having been formulated with EUDRAGIT®RS 30 D, differ already after a short time of storage. In contrast, the release profile of tablets which have been formulated with Surelease® are almost invariant, even after 15 months of storage.

|  | Storage time (Months) | | |
|---|---|---|---|
|  | 0 | 1 | 3,5 |
| Time | Preparation (designation) | | |
| (min) | Nal-5-Eud-0 | Nal-5-Eud-1 | Nal-5-Eud-3,5 |
| 15 | 16.46 | 12.66 | 15.06 |
| 90 | 30.29 | 28.78 | 30.6 |
| 240 | 52.94 | 43.85 | 47.5 |
| 480 | 71.07 | 57.37 | 62.86 |
| 720 | 83.29 | 66.68 | 73.58 |
| 1020 | 91.61 | 73.03 | 80.97 |

|  | Storage time (Months) | | | |
|---|---|---|---|---|
|  | 0 | 3 | 6 | 15 |
| Time | Preparation (designation) | | | |
| (min) | Nal-5-Sure-0 | Nal-5-Sure-3 | Nal-5-Sure-6 | Nal-5-Sure-15 |
| 15 | 21.58 | 22.52 | 16.04 | 24.36 |
| 120 | 49.94 | 49.05 | 51.93 | 55.59 |
| 420 | 79.83 | 86.32 | 87.99 | 88.49 |
| 720 | 91.74 | 97.55 | 100.27 | 97.09 |

In the Table, the release rates are given in percentages. In each case, the release of naloxone was tested.

Example 14

Production of Tablets with Different Oxycodone/Naloxone Amounts in a Non-Swellable Diffusion Matrix by Extrusion The following amounts of the listed components were used for the production of oxycodone/naloxone tablets according to the invention.

|  | Preparation (designation) | | | |
|---|---|---|---|---|
|  | OxN20/1-Extr-A | OxN20/1-Extr-B | OxN20/1-Extr-C | OxN20/10-Extr-A |
| Oxycodone HCl | 20 mg | 20 mg | 20 mg | 20 mg |
| Naloxone HCl | 1 mg | 1 mg | 1 mg | 10 mg |
| Lactose Flow Lac 100 | 58.25 mg | 58.25 mg | 58.25 mg | 49.25 mg |
| Kollidon ® 30 | 6 mg | 6 mg | 6 mg | 6 mg |
| Ethylcellulose | 10 mg | 10 mg | 10 mg | 10 mg |
| Stearly alcohol | 24 mg | 24 mg | 24 mg | 24 mg |
| Talcum | 1.25 mg | 1.25 mg | 1.25 mg | 1.25 mg |
| Mg-Stearate | 2.5 mg | 2.5 mg | 2.5 mg | 2.5 mg |

Extrusion was performed as described above (Example 2) with the following parameters:

| OxN20/1-Extr-A: | temperature: | 55-63° C. |
|---|---|---|
|  | rpm (screw): | 150 rpm |
|  | feeding rate: | 1.5 kg/h |
| OxN20/1-Extr-B: | temperature: | 55-63° C. |
|  | rpm (screw): | 155 rpm |
|  | feeding rate: | 1.5 kg/h |
| OxN20/1-Extr-C: | temperature: | 55-63° C. |
|  | rpm (screw): | 1505 rpm |
|  | feeding rate: | 1.5 kg/h |
| OxN20/10-Extr-A: | temperature: | 55-63° C. |
|  | rpm (screw): | 160 rpm |
|  | feeding rate: | 1.75 kg/h |

Tablet production was performed with a common tabletting device with the following parameters:

| OxN20/1-Extr-A: | rpm: | 40 rpm |
|---|---|---|
|  | Pressure power: | 9 kN |
| OxN20/1-Extr-B: | rpm: | 42 rpm |
|  | Pressure power: | 8.9 kN |
| OxN20/1-Extr-C: | rpm: | 36 rpm |
|  | Pressure power: | 9 kN |
| OxN20/10-Extr-A: | rpm: | 36 rpm |
|  | Pressure power: | 7.5 kN |

The release of the active compounds was measured over a time period of 12 hours, applying the Basket Method according to USP at pH 1.2 using HPLC. Tablets OxN20/1-Extr-A, OxN20/1-Extr-B, OxN20/1-Extr-C and OxN20/10-Extr-A were tested.

One recognizes from the values listed in the Table that in the case of a non-swellable diffusion matrix based on ethylcellulose, the release rates of different naloxone amounts, independent of the oxycodone amount, remain substantially equal. Correspondingly, the preparations provide for an independent and invariant release of the active compounds.

| Time | OxN20/1-Extr-A | | OxN20/1-Extr-B | | OxN20/1-Extr-C | | OxN20/10-Extr-A | |
|---|---|---|---|---|---|---|---|---|
| (min) | Oxy | Nal | Oxy | Nal | Oxy | Nal | Oxy | Nal |
| 0 | 0 | 0 | 0 | 0 | 0 | 0 | 0 | 0 |
| 15 | 21.2 | 25.8 | 21.7 | 21.1 | 19.7 | 19.3 | 23.3 | 24.3 |
| 120 | 56.6 | 53.8 | 58.8 | 57.3 | 57.7 | 56.2 | 64.5 | 66.9 |
| 420 | 87.2 | 84.5 | 94.2 | 92.6 | 93.7 | 91.5 | 92.7 | 96.3 |
| 720 | 99.7 | 96.8 | 100.1 | 98 | 100.6 | 97.5 | 93.6 | 97.4 |

The release values refer to oxycodone or naloxone (line 2) and are given as percentages. The mean value for the release of naloxone at e.g. 420 min is 92.3%. The maximal deviation at 420 min is 7.4%. Oxy and Nal stand for oxycodone and naloxone and indicate the active compound which has been measured.

Thus, once a preparation with the desired release profile has been developed, one can change the amount of the active compounds without significantly changing the release profiles of the active compounds. The preparations comprising different amounts of the active compounds still provide for a sustained, independent an invariant release of the active compounds.

Example 15

Production of Tablets with Oxycodone/Naloxone in a Non-Swellable Diffusion Matrix by Extrusion In the following example it is set out that using formulations according to the present invention, preparations comprising oxycodone and naloxone with particular release behaviours may be obtained.

The following amounts of the listed components were used for the production of oxycodone/naloxone tablets according to the invention.

| | Preparation (designation) | | | | | |
|---|---|---|---|---|---|---|
| | OxN20/1-Extr-D | OxN20/1-Extr-E | OxN20/10-Extr-B | OxN20/10-Extr-C | OxN20/10-Extr-D | OxN20/10-Extr-E |
| oxycodone HCl | 20 mg | 20 mg | 20 mg | 20 mg | 20 mg | 20 mg |
| naloxone HCl | 1 mg | 1 mg | 10 mg | 10 mg | 10 mg | 10 mg |
| Lactose Flow Lac 100 | 56.25 mg | 56.25 mg | 54.25 mg | 65.25 mg | 60.25 mg | 55.25 |
| Kollidon ® 30 | 7 mg | 6 mg | 6 mg | 7.25 mg | 7.25 mg | 7.25 mg |
| Ethylcellulose | 11 mg | 12 mg | 10 mg | 12 mg | 12 mg | 12 mg |
| Stearyl alcohol | 24 mg | 24 mg | 24 mg | 28.75 mg | 28.75 mg | 28.75 mg |
| Talcum | 1.25 mg | 1.25 mg | 1.25 mg | 1.25 mg | 1.25 mg | 1.25 mg |
| Mg-Stearate | 2.5 mg | 2.5 mg | 2.5 mg | 2.5 mg | 2.5 mg | 2.5 mg |

Extrusion was performed as described above (Example 2) with the following parameters:

| OxN20/1-Extr-D: | temperature: | 55-63° C. |
|---|---|---|
| | rpm (screw): | 150 rpm |
| | feeding rate: | 1.5 kg/h |
| OxN20/1-Extr-E: | temperature: | 55-63° C. |
| | rpm (screw): | 150 rpm |
| | feeding rate: | 1.5 kg/h |
| OxN20/10-Extr-B: | temperature: | 55-63° C. |
| | rpm (screw): | 160 rpm |
| | feeding rate: | 1.75 kg/h |

-continued

| OxN20/10-Extr-C: | temperature: | 55-63° C. |
|---|---|---|
| | rpm (screw): | 160 rpm |
| | feeding rate: | 1.75 kg/h |
| OxN20/10-Extr-D: | temperature: | 55-63° C. |
| | rpm (screw): | 150 rpm |
| | feeding rate: | 1.5 kg/h |
| OxN20/10-Extr-E: | temperature: | 55-63° C. |
| | rpm (screw): | 150 rpm |
| | feeding rate: | 1.5 kg/h |

Tablet production was performed with a common tabletting device with the following parameters:

| OxN20/1-Extr-D: | rpm: | 39 rpm |
|---|---|---|
| | Pressure power: | 11 kN |
| OxN20/1-Extr-E: | rpm: | 39 rpm |
| | Pressure power: | 10.5 kN |
| OxN20/10-Extr-B: | rpm: | 36 rpm |
| | Pressure power: | 9.5 kN |
| OxN20/10-Extr-C: | rpm: | 36 rpm |
| | Pressure power: | 7.8 kN |
| OxN20/10-Extr-D: | rpm: | 39 rpm |
| | Pressure power: | 9 kN |

-continued

| OxN20/10-Extr-E: | rpm: | 39 rpm |
|---|---|---|
| | Pressure power: | 7.5 kN |

The release of the active compounds was measured over a time period of 12 hours, applying the Basket Method according to USP at pH 1.2 using HPLC. Tablets OxN20/1-Extr-D, OxN20/1-Extr-E, OxN20/10-Extr-B, OxN20/10-Extr-C, OxN20/10-Extr-D and OxN20/10-Extr-E were tested.

| Time | OxN20/1-Extr-D | | OxN20/1-Extr-E | | OxN20/10-Extr-B | | OxN20/10-Extr-C | | OxN20/10-Extr-D | | OxN20/10-Extr-E | |
|---|---|---|---|---|---|---|---|---|---|---|---|---|
| (min) | Oxy | Nal | Oxy | Nal | Oxy | Nal | Oxy | Nal | Oxy | Nal | Oxy | Nal |
| 0 | 0 | 0 | 0 | 0 | 0 | 0 | 0 | 0 | 0 | 0 | 0 | 0 |
| 15 | 16.6 | 16.2 | 17.4 | 17.2 | 26.1 | 26.8 | 21.8 | 21.9 | 18.5 | 18.2 | 18.4 | 18.2 |
| 120 | 47.6 | 46.9 | 49.6 | 49.7 | 71.1 | 73.0 | 61.2 | 61.8 | 52.8 | 52.8 | 53.3 | 53.3 |
| 420 | 82.7 | 84.5 | 84.6 | 85.7 | 94.3 | 96.6 | 93.2 | 94.7 | 86.3 | 86.3 | 87.2 | 88.2 |
| 720 | 95 | 97 | 95.2 | 95.8 | 94.9 | 97.9 | 96.4 | 97.9 | 94.8 | 94.8 | 95.7 | 96.5 |

The release values refer to oxycodone or naloxone (line 2) and are given as percentages. Oxy and Nal stand for oxycodone and naloxone and indicate the active compound which has been measured.

The example shows that preparations with particular release profiles may be produced if ethylcellulose and fatty alcohols are used as the matrix-components that essentially influence the release characteristics of the preparations. Once a preparation with desired release characteristics has been obtained the amount of the active compounds may be changed. The preparations will still provide for a sustained, independent and invariant release behaviour (see example 14).

Example 16

Production of Tablets with Naloxone in a Non-Swellable Diffusion Matrix by Extrusion The following amounts of the listed components were used for the production of naloxone tablets according to the invention.

|  | Preparation (designation) | | | | | |
| --- | --- | --- | --- | --- | --- | --- |
|  | N10-Extr-1 | N10-Extr-2 | N10-Extr-3 | N10-Extr-4 | N10-Extr-5 | N10-Extr-6 |
| Naloxone HCl | 10 mg | 10 mg | 10 mg | 10 mg | 10 mg | 10 mg |
| Lactose Flow Lac 100 | 69.25 mg | 69.25 mg | 69.25 mg | 69.25 mg | 69.25 mg | 69.25 mg |
| Povidone 30 | 5.0 mg | 5.0 mg | 5.0 mg | 5.0 mg | 5.0 mg | 5.0 mg |
| Ethylcellulose | 10 mg | 10 mg | 10 mg | 10 mg | 10 mg | 10 mg |
| Stearyl alcohol | 25 mg | 25 mg | 25 mg | 25 mg | 25 mg | 25 mg |
| Talcum | 1.25 mg | 1.25 mg | 1.25 mg | 1.25 mg | 1.25 mg | 1.25 mg |
| Mg-Stearate | 2.5 mg | 2.5 mg | 2.5 mg | 2.5 mg | 2.5 mg | 2.5 mg |

Extrusion was performed as described above with the following parameters:

| N10-Extr-1: | temperature: | 55-63° C. |
| --- | --- | --- |
|  | rpm (screw): | 120 rpm |
|  | feeding rate: | 1.5 kg/h |
| N10-Extr-2: | temperature: | 55-63° C. |
|  | rpm (screw): | 140 rpm |
|  | feeding rate: | 1.5 kg/h |
| N10-Extr-3: | temperature: | 55-63° C. |
|  | rpm (screw): | 160 rpm |
|  | feeding rate: | 1.75 kg/h |
| N10-Extr-4: | temperature: | 55° C. |
|  | rpm (screw): | 120 rpm |
|  | feeding rate: | 1.75 kg/h |
| N10-Extr-5: | temperature: | 55-55° C. |
|  | rpm (screw): | 140 rpm |
|  | feeding rate: | 1.5 kg/h |
| N10-Extr-6: | temperature: | 55° C. |
|  | rpm (screw): | 160 rpm |
|  | feeding rate: | 1.5 kg/h |

Tablet production was performed with a common tabletting device with the following parameters:

| N10-Extr-1: | rpm: | 39 rpm |
| --- | --- | --- |
|  | Pressure power: | 11.6 kN |
| N10-Extr-2: | rpm: | 39 rpm |
|  | Pressure power: | 12.5 kN |
| N10-Extr-3: | rpm: | 39 rpm |
|  | Pressure power: | 11.6 kN |
| N10-Extr-4: | rpm: | 36 rpm |
| N10-Extr-5: | Pressure power: | 14.5 kN |
|  | rpm: | 36 rpm |
|  | Pressure power: | 15.0 kN |
| N10-Extr-6: | rpm: | 36 rpm |
|  | Pressure power: | 15.0 kN |

The release of the active compound was measured over a time period of 12 hours, applying the Basket Method according to USP at pH 1.2 using HPLC. Tablets N10-Extr-A, N10-Extr-B, N10-Extr-C, N10-Extr-D, N10-Extr-E and N10-Extr-F were tested.

One recognizes the values listed in the Table that, in the case of a non-swellable diffusion matrix based on ethylcellulose and a fatty alcohol, the release rates of naloxone remain substantially equal (invariant).

| Time (min) | N10-Extr-1 | N10-Extr-2 | N10-Extr-3 | N10-Extr-4 | N10-Extr-5 | N10-Extr-6 |
| --- | --- | --- | --- | --- | --- | --- |
| 0 | 0 | 0 | 0 | 0 | 0 | 0 |
| 15 | 13.0 | 12.9 | 13.0 | 13.2 | 13.3 | 13.5 |
| 120 | 37.4 | 37.6 | 37.9 | 37.6 | 37.9 | 38.7 |
| 420 | 67 | 67.3 | 67.9 | 67.5 | 67.4 | 69.5 |
| 600 | 78.1 | 78.5 | 78.7 | 78.4 | 78.3 | 80.5 |

The release values refer to naloxone and are given as percentages. The mean value for the release of naloxone at e.g. 420 min is 67.8%. The maximal deviation at 420 min is 2.5%.

What is claimed is:

1. An oral pharmaceutical formulation comprising:
   at least one opioid agonist selected from oxycodone and pharmaceutically acceptable salts thereof;
   at least one opioid antagonist selected from naloxone and pharmaceutically acceptable salts thereof; and
   a diffusion matrix containing the at least one opioid agonist and the at least one opioid antagonist and comprising ethylcellulose and at least one fatty alcohol; wherein the matrix is configured to provide sustained, invariant, and independent release of the opioid agonist and the opioid antagonist; and wherein the fatty alcohol is present in 5-30% by weight of the total formulation.

2. The pharmaceutical formulation of claim 1, wherein the fatty alcohol is selected from lauryl alcohol, myristyl alcohol, stearyl alcohol, cetylstearyl alcohol, ceryl alcohol, and cetyl alcohol.

3. The pharmaceutical formulation of claim 1, wherein the fatty alcohol is stearyl alcohol.

4. The pharmaceutical formulation of claim 1, wherein the opioid agonist is oxycodone hydrochloride.

5. The pharmaceutical formulation of claim 1, wherein the oxycodone or pharmaceutically acceptable salt thereof is present in an amount ranging from 5 to 50 mg.

6. The pharmaceutical formulation of claim 1, wherein the opioid antagonist is naloxone hydrochloride.

7. The pharmaceutical formulation of claim 1, wherein the naloxone or pharmaceutically acceptable salt thereof is present in an amount ranging from 1 to 40 mg.

8. The pharmaceutical formulation of claim 1, wherein:
the opioid agonist is oxycodone hydrochloride; and
the opioid antagonist is naloxone hydrochloride.

9. The pharmaceutical formulation of claim 1, wherein:
the oxycodone or pharmaceutically acceptable salt thereof is present in an amount ranging from 10 to 150 mg; and
the naloxone or pharmaceutically acceptable salt thereof is present in an amount ranging from 1 to 50 mg.

10. The pharmaceutical formulation of claim 9, wherein the oxycodone or pharmaceutically acceptable salt thereof is present in an amount ranging from 10 to 80 mg.

11. The pharmaceutical formulation of claim 1, wherein the oxycodone or pharmaceutically acceptable salt thereof is present in an amount ranging from 5 to 50 mg.

12. The pharmaceutical formulation of claim 1, wherein the oxycodone or pharmaceutically acceptable salt thereof and the naloxone or pharmaceutically acceptable salt thereof are present in a weight ratio ranging from 25:1 to 1:1.

13. The pharmaceutical formulation of claim 1, wherein the oxycodone or pharmaceutically acceptable salt thereof and the naloxone or pharmaceutically acceptable salt thereof are present in a weight ratio ranging from 5:1 to 1:1.

14. The pharmaceutical formulation of claim 1, wherein the oxycodone or pharmaceutically acceptable salt thereof and the naloxone or pharmaceutically acceptable salt thereof are present in a weight ratio of 5:1, 4:1, 3:1, 2:1, or 1:1.

15. The pharmaceutical formulation of claim 1, wherein the oxycodone or pharmaceutically acceptable salt thereof and the naloxone or pharmaceutically acceptable salt thereof are present in a weight ratio of 2:1.

16. The pharmaceutical formulation of claim 1, wherein the ethylcellulose is present in 1-15% by weight of the total formulation.

17. The pharmaceutical formulation of claim 1, wherein the ethylcellulose is present in 5-9% by weight of the total formulation.

18. The pharmaceutical formulation of claim 1, wherein the fatty alcohol is present in 15-20% by weight of the total formulation.

19. The pharmaceutical formulation of claim 1, wherein the fatty alcohol is present in 10-25% by weight of the total formulation.

20. The pharmaceutical formulation of claim 1, wherein
the ethylcellulose is present in 1-15% by weight of the total formulation;
the fatty alcohol is stearyl alcohol and is present in 10-25% by weight of the total formulation; and
the oxycodone or pharmaceutically acceptable salt thereof and is present in an amount ranging from 10 to 80 mg;
wherein the oxycodone or pharmaceutically acceptable salt thereof and the naloxone or pharmaceutically acceptable salt thereof are present in a weight ratio of 2:1.

21. The pharmaceutical formulation of claim 20, wherein:
the opioid agonist is oxycodone hydrochloride; and
the opioid antagonist is naloxone hydrochloride.

22. The pharmaceutical formulation of claim 1, wherein the formulation is in the form of a tablet.

23. The pharmaceutical formulation of claim 1, wherein the matrix is not based on a polymethacrylate.

24. The pharmaceutical formulation of claim 1, wherein the matrix does not comprise a relevant amount of a hydroxyalkylcellulose.

25. The pharmaceutical formulation of claim 1, wherein the sustained, invariant, and independent release characteristics of the matrix are determined by the ethylcellulose and the at least one fatty alcohol.

26. An oral pharmaceutical formulation comprising:
at least one opioid agonist selected from oxycodone and pharmaceutically acceptable salts thereof;
at least one opioid antagonist selected from naloxone and pharmaceutically acceptable salts thereof; and
a diffusion matrix containing the at least one opioid agonist and the at least one opioid antagonist and comprising ethylcellulose and at least one fatty alcohol;
wherein the matrix is configured to provide sustained, invariant, and independent release of the opioid agonist and the opioid antagonist; and wherein ethylcellulose is present in 1-15% by weight of the total formulation.

27. The pharmaceutical formulation of claim 26, wherein the fatty alcohol is selected from lauryl alcohol, myristyl alcohol, stearyl alcohol, cetylstearyl alcohol, ceryl alcohol, and cetyl alcohol.

28. The pharmaceutical formulation of claim 26, wherein the fatty alcohol is stearyl alcohol.

29. The pharmaceutical formulation of claim 26, wherein the opioid agonist is oxycodone hydrochloride.

30. The pharmaceutical formulation of claim 26, wherein the oxycodone or pharmaceutically acceptable salt thereof is present in an amount ranging from 5 to 50 mg.

31. The pharmaceutical formulation of claim 26, wherein the opioid antagonist is naloxone hydrochloride.

32. The pharmaceutical formulation of claim 26, wherein the naloxone or pharmaceutically acceptable salt thereof is present in an amount ranging from 1 to 40 mg.

33. The pharmaceutical formulation of claim 26, wherein: the opioid agonist is oxycodone hydrochloride; and the opioid antagonist is naloxone hydrochloride.

34. The pharmaceutical formulation of claim 26, wherein:
the oxycodone or pharmaceutically acceptable salt thereof is present in an amount
ranging from 10 to 150 mg; and
the naloxone or pharmaceutically acceptable salt thereof is present in an amount ranging from 1 to 50 mg.

35. The pharmaceutical formulation of claim 34, wherein the oxycodone or pharmaceutically acceptable salt thereof is present in an amount ranging from 10 to 80 mg.

36. The pharmaceutical formulation of claim 26, wherein the oxycodone or pharmaceutically acceptable salt thereof is present in an amount ranging from 5 to 50 mg.

37. The pharmaceutical formulation of claim 26, wherein the oxycodone or pharmaceutically acceptable salt thereof and the naloxone or pharmaceutically acceptable salt thereof are present in a weight ratio ranging from 25:1 to 1:1.

38. The pharmaceutical formulation of claim 26, wherein the oxycodone or pharmaceutically acceptable salt thereof and the naloxone or pharmaceutically acceptable salt thereof are present in a weight ratio ranging from 5:1 to 1:1.

39. The pharmaceutical formulation of claim 26, wherein the oxycodone or pharmaceutically acceptable salt thereof and the naloxone or pharmaceutically acceptable salt thereof are present in a weight ratio of 5:1, 4:1, 3:1, 2:1, or 1:1.

40. The pharmaceutical formulation of claim 26, wherein the oxycodone or pharmaceutically acceptable salt thereof and the naloxone or pharmaceutically acceptable salt thereof are present in a weight ratio of 2:1.

41. The pharmaceutical formulation of claim 26, wherein the ethylcellulose is present in 3-12% by weight of the total formulation.

42. The pharmaceutical formulation of claim 26, wherein the ethylcellulose is present in 5-9% by weight of the total formulation.

43. The pharmaceutical formulation of claim 26, wherein the fatty alcohol is present in 15-20% by weight of the total formulation.

44. The pharmaceutical formulation of claim 26, wherein the fatty alcohol is present in 10-25% by weight of the total formulation.

45. The pharmaceutical formulation of claim 26, wherein the fatty alcohol is stearyl alcohol and is present in 10-25% by weight of the total formulation; and
the oxycodone or pharmaceutically acceptable salt thereof and is present in an amount ranging from 10 to 80 mg; and
wherein the oxycodone or pharmaceutically acceptable salt thereof and the naloxone or pharmaceutically acceptable salt thereof are present in a weight ratio of 2:1.

46. The pharmaceutical formulation of claim 45, wherein:
the opioid agonist is oxycodone hydrochloride; and
the opioid antagonist is naloxone hydrochloride.

47. The pharmaceutical formulation of claim 26, wherein the formulation is in the form of a tablet.

48. The pharmaceutical formulation of claim 26, wherein the matrix is not based on a polymethacrylate.

49. The pharmaceutical formulation of claim 26, wherein the matrix does not comprise a relevant amount of a hydroxyalkylcellulose.

50. The pharmaceutical formulation of claim 26, wherein the sustained, invariant, and independent release characteristics of the matrix are determined by the ethylcellulose and the at least one fatty alcohol.

* * * * *